(12) United States Patent
Arya et al.

(10) Patent No.: US 10,722,292 B2
(45) Date of Patent: Jul. 28, 2020

(54) SURGICAL DEVICE WITH AN END-EFFECTOR ASSEMBLY AND SYSTEM FOR MONITORING OF TISSUE DURING A SURGICAL PROCEDURE

(71) Applicant: COVIDIEN LP, Mansfield, MA (US)

(72) Inventors: Shobhit Arya, Berkshire (GB); Lei Su, London (GB); Vadzim Chalau, Whitefield (GB); Kristy Lee Cloyd, San Jose, CA (US); Martin A. B. Hedegaard, Odense C (DK); Molly Stevens, London (GB); Daniel S. Elson, London (GB); George B. Hanna, Middlesex (GB)

(73) Assignee: Covidien LP, Mansfield, MA (US)

( * ) Notice: Subject to any disclaimer, the term of this patent is extended or adjusted under 35 U.S.C. 154(b) by 827 days.

(21) Appl. No.: 14/892,359

(22) PCT Filed: Jun. 2, 2014

(86) PCT No.: PCT/US2014/040505
§ 371 (c)(1),
(2) Date: Nov. 19, 2015

(87) PCT Pub. No.: WO2014/194317
PCT Pub. Date: Dec. 4, 2014

(65) Prior Publication Data
US 2016/0089198 A1    Mar. 31, 2016

Related U.S. Application Data

(60) Provisional application No. 61/839,606, filed on Jun. 26, 2013, provisional application No. 61/829,420, filed on May 31, 2013.

(51) Int. Cl.
*A61B 18/00* (2006.01)
*A61B 18/14* (2006.01)
(Continued)

(52) U.S. Cl.
CPC ........ *A61B 18/1445* (2013.01); *A61B 5/0071* (2013.01); *A61B 5/0075* (2013.01);
(Continued)

(58) Field of Classification Search
CPC ....... A61B 18/14; A61B 8/12; A61B 18/1445; A61B 5/0066; A61B 5/0071;
(Continued)

(56) References Cited

U.S. PATENT DOCUMENTS

D249,549 S    9/1978    Pike
D263,020 S    2/1982    Rau, III
(Continued)

FOREIGN PATENT DOCUMENTS

CN    201299462          9/2009
DE    2415263 A1    10/1975
(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003. (4 pages).
(Continued)

*Primary Examiner* — Jaymi E Della
*Assistant Examiner* — Rachel A. Vierra
(74) *Attorney, Agent, or Firm* — Carter, DeLuca & Farrell LLP

(57) ABSTRACT

A medical instrument is provided and includes a housing and a shaft coupled to the housing. The shaft has a proximal end and a distal end. An end-effector assembly is disposed at the distal end of the shaft. The end-effector assembly includes first and second jaw members. At least one of the first and second jaw members is movable from a first position wherein the first and second jaw members are disposed in spaced relation relative to one another to at least a second
(Continued)

position closer to one another wherein the first and second jaw members cooperate to grasp tissue therebetween. The medical instrument also includes one or more light-emitting elements and one or more light-detecting elements configured to generate one or more signals indicative of tissue florescence. The one or more light-emitting elements are adapted to deliver light energy to tissue grasped between the first and second jaw members.

17 Claims, 27 Drawing Sheets

(51) Int. Cl.
*A61B 5/00* (2006.01)
*A61B 90/30* (2016.01)
*A61B 5/01* (2006.01)
*A61B 17/00* (2006.01)
*A61B 17/29* (2006.01)

(52) U.S. Cl.
CPC ........ *A61B 18/1482* (2013.01); *A61B 5/0066* (2013.01); *A61B 5/01* (2013.01); *A61B 5/4836* (2013.01); *A61B 5/4848* (2013.01); *A61B 5/6884* (2013.01); *A61B 2017/0003* (2013.01); *A61B 2017/00057* (2013.01); *A61B 2017/2926* (2013.01); *A61B 2018/0063* (2013.01); *A61B 2018/00648* (2013.01); *A61B 2018/00702* (2013.01); *A61B 2018/00773* (2013.01); *A61B 2018/00994* (2013.01); *A61B 2090/306* (2016.02)

(58) Field of Classification Search
CPC ... A61B 5/0059; A61B 5/0261; A61B 5/0075; A61B 18/1482; A61B 2017/0003; A61B 2017/00057; A61B 2017/2926; A61B 2018/0063; A61B 2018/00648; A61B 2018/00702; A61B 2018/00773; A61B 2018/00994
See application file for complete search history.

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,562,100 A * | 10/1996 | Kittrell ............... A61B 5/0071 600/476 |
| D384,413 S | 9/1997 | Zlock et al. |
| 5,697,373 A | 12/1997 | Richards-Kortum et al. |
| 5,762,609 A | 6/1998 | Benaron et al. |
| 5,769,791 A | 6/1998 | Benaron et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| 5,991,653 A | 11/1999 | Richards-Kortum et al. |
| D424,694 S | 5/2000 | Tetzlaff et al. |
| D425,201 S | 5/2000 | Tetzlaff et al. |
| 6,095,982 A | 8/2000 | Richards-Kortum et al. |
| H1904 H | 10/2000 | Yates et al. |
| 6,134,003 A | 10/2000 | Tearney et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,507,747 B1 | 1/2003 | Gowda et al. |
| 6,522,407 B2 | 2/2003 | Everett et al. |
| 6,527,708 B1 | 3/2003 | Nakamura et al. |
| 6,725,073 B1 | 4/2004 | Motamedi et al. |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| 6,868,285 B2 | 3/2005 | Muller-Dethlefs |
| 6,889,075 B2 | 5/2005 | Marchitto et al. |
| D509,297 S | 9/2005 | Wells |
| 6,975,898 B2 | 12/2005 | Seibel |
| 7,039,446 B2 | 5/2006 | Ruchti et al. |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| 7,236,815 B2 | 6/2007 | Richards-Kortum et al. |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,474,407 B2 | 1/2009 | Gutin |
| 7,499,153 B2 | 3/2009 | Puppels et al. |
| 7,508,524 B2 | 3/2009 | Mahadevan-Jansen et al. |
| 7,510,849 B2 | 3/2009 | Schurman et al. |
| 7,593,763 B2 | 9/2009 | Lambert et al. |
| 7,679,754 B2 | 3/2010 | Zuluaga |
| 7,708,408 B1 | 5/2010 | Bor |
| 7,725,144 B2 | 5/2010 | Ediger et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,749,168 B2 | 7/2010 | Maschke et al. |
| D621,503 S | 8/2010 | Otten et al. |
| 7,796,243 B2 | 9/2010 | Choo-Smith et al. |
| 7,801,343 B2 | 9/2010 | Unal et al. |
| 7,801,590 B2 | 9/2010 | Feldman et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,952,719 B2 | 5/2011 | Brennan, III |
| 7,983,736 B2 | 7/2011 | Villard et al. |
| 8,023,119 B2 | 9/2011 | Tsai et al. |
| 8,036,727 B2 | 10/2011 | Schurman et al. |
| 8,036,732 B2 | 10/2011 | Milner |
| 8,043,227 B2 | 10/2011 | Van Gogh et al. |
| D649,249 S | 11/2011 | Guerra |
| D649,643 S | 11/2011 | Allen, IV et al. |
| 8,049,886 B1 | 11/2011 | Raksi |
| 8,078,244 B2 | 12/2011 | Melman et al. |
| 8,095,193 B2 | 1/2012 | Ridder et al. |
| 8,150,496 B2 | 4/2012 | Tearney et al. |
| 8,162,834 B2 | 4/2012 | Feldman et al. |
| D661,394 S | 6/2012 | Romero et al. |
| 8,230,866 B2 | 7/2012 | Hauger et al. |
| 8,260,390 B2 | 9/2012 | Tang |
| D670,808 S | 11/2012 | Moua et al. |
| 8,326,404 B2 | 12/2012 | Zeng et al. |
| 8,330,962 B2 | 12/2012 | Nebosis et al. |
| 8,355,767 B2 | 1/2013 | Hunter et al. |
| D680,220 S | 4/2013 | Rachlin |

(56) References Cited

U.S. PATENT DOCUMENTS

| | | | |
|---|---|---|---|
| 8,423,104 B2 | 4/2013 | Wiseman et al. | |
| 8,457,440 B1 | 6/2013 | Johnson | |
| 8,474,978 B2 | 7/2013 | Huang et al. | |
| 8,478,384 B2 | 7/2013 | Schmitt et al. | |
| 8,526,004 B2 | 9/2013 | Barbato | |
| 8,548,549 B2 | 10/2013 | Schurman et al. | |
| 8,553,219 B2 | 10/2013 | Patil et al. | |
| 8,571,617 B2 | 10/2013 | Reichgott et al. | |
| 8,581,697 B2 | 11/2013 | Ridder et al. | |
| 8,622,548 B2 | 1/2014 | Guo et al. | |
| 8,647,835 B2 | 2/2014 | Walsh et al. | |
| 8,665,450 B2 | 3/2014 | Johnson et al. | |
| 8,676,299 B2 | 3/2014 | Schmitt et al. | |
| 8,768,423 B2 | 7/2014 | Shakespeare et al. | |
| 8,774,904 B2 | 7/2014 | Birngruber et al. | |
| 8,788,003 B2 | 7/2014 | Schurman et al. | |
| 8,794,763 B2 | 8/2014 | Stetson et al. | |
| 8,801,180 B2 | 8/2014 | Hayashi et al. | |
| 8,812,080 B2 | 8/2014 | Nachabe et al. | |
| 8,820,931 B2 | 9/2014 | Walsh et al. | |
| 8,827,453 B2 | 9/2014 | Nakajima et al. | |
| 8,868,155 B2 | 10/2014 | Debuc | |
| 8,868,356 B2 | 10/2014 | Liu | |
| 8,892,191 B2 | 11/2014 | Brennan et al. | |
| 8,913,248 B2 | 12/2014 | Sharma et al. | |
| 8,914,098 B2 | 12/2014 | Brennan et al. | |
| 8,934,104 B2 | 1/2015 | Koerner et al. | |
| 8,965,487 B2 | 2/2015 | Bouma et al. | |
| 8,970,838 B2 | 3/2015 | Messerschmidt | |
| 8,994,954 B2 | 3/2015 | Atia et al. | |
| 9,060,711 B2 | 6/2015 | Narasimha-Iyer | |
| 9,066,784 B2 | 6/2015 | Goldshleger et al. | |
| 9,089,331 B2 | 7/2015 | Rollins et al. | |
| 9,107,610 B2 | 8/2015 | Reisman et al. | |
| 9,134,300 B2 | 9/2015 | Danias et al. | |
| 2003/0171741 A1* | 9/2003 | Ziebol | A61B 18/245 606/7 |
| 2004/0092830 A1 | 5/2004 | Scott et al. | |
| 2004/0098070 A1 | 5/2004 | Mohr et al. | |
| 2004/0162487 A1 | 8/2004 | Klingenbeck-Regn et al. | |
| 2004/0162489 A1 | 8/2004 | Richards-Kortum et al. | |
| 2004/0260183 A1 | 12/2004 | Lambert et al. | |
| 2005/0131390 A1 | 6/2005 | Heinrich et al. | |
| 2006/0241342 A1 | 10/2006 | Macaulay et al. | |
| 2006/0276696 A1 | 12/2006 | Schurman et al. | |
| 2007/0060806 A1 | 3/2007 | Hunter et al. | |
| 2007/0078500 A1 | 4/2007 | Ryan et al. | |
| 2007/0232872 A1 | 10/2007 | Prough et al. | |
| 2007/0232873 A1 | 10/2007 | Esenaliev et al. | |
| 2007/0268456 A1 | 11/2007 | Ohbayshi et al. | |
| 2008/0125634 A1 | 5/2008 | Ryan et al. | |
| 2008/0200781 A1 | 8/2008 | Van Herpen et al. | |
| 2008/0221457 A1 | 9/2008 | Zeng et al. | |
| 2008/0269580 A1 | 10/2008 | Balistreri et al. | |
| 2009/0054908 A1 | 2/2009 | Zand et al. | |
| 2009/0069673 A1 | 3/2009 | Tapalian et al. | |
| 2009/0234204 A1 | 9/2009 | Ridder et al. | |
| 2009/0234236 A1 | 9/2009 | Lomnes et al. | |
| 2009/0261804 A1* | 10/2009 | McKenna | A61B 18/1442 324/71.1 |
| 2009/0270702 A1* | 10/2009 | Zeng | A61B 5/0075 600/323 |
| 2009/0306520 A1 | 12/2009 | Schmitt et al. | |
| 2010/0041986 A1 | 2/2010 | Nguyen et al. | |
| 2010/0069760 A1 | 3/2010 | Tang | |
| 2010/0174196 A1 | 7/2010 | Ryan et al. | |
| 2010/0241058 A1 | 9/2010 | Ahmed et al. | |
| 2010/0255440 A1 | 10/2010 | Nakaji | |
| 2011/0150293 A1 | 6/2011 | Bower et al. | |
| 2011/0251605 A1* | 10/2011 | Hoarau | A61B 18/1233 606/34 |
| 2011/0319731 A1 | 12/2011 | Schurman et al. | |
| 2012/0022360 A1 | 1/2012 | Kemp | |
| 2012/0101372 A1 | 4/2012 | Teramura et al. | |
| 2012/0101374 A1 | 4/2012 | Tearney et al. | |
| 2012/0133887 A1 | 5/2012 | Huang | |
| 2012/0150001 A1 | 6/2012 | Shakespeare et al. | |
| 2012/0203114 A1 | 8/2012 | Bechtel et al. | |
| 2012/0209094 A1 | 8/2012 | Schurman et al. | |
| 2012/0296205 A1 | 11/2012 | Chernov et al. | |
| 2012/0316558 A1 | 12/2012 | Hendriks et al. | |
| 2012/0330305 A1* | 12/2012 | Zoran | A61B 18/1233 606/41 |
| 2013/0095519 A1 | 4/2013 | Backman et al. | |
| 2013/0103015 A1 | 4/2013 | Grant et al. | |
| 2013/0208245 A1 | 8/2013 | Campbell | |
| 2013/0219969 A1 | 8/2013 | Bhagavatula et al. | |
| 2013/0231573 A1 | 9/2013 | Zeng et al. | |
| 2013/0303889 A1 | 11/2013 | Jang et al. | |
| 2013/0317328 A1 | 11/2013 | Ridder et al. | |
| 2013/0342811 A1 | 12/2013 | Warm et al. | |
| 2014/0018669 A1 | 1/2014 | Xu | |
| 2014/0073917 A1 | 3/2014 | Huang et al. | |
| 2014/0121507 A1 | 5/2014 | Nau, Jr. | |
| 2014/0121508 A1 | 5/2014 | Latimer et al. | |
| 2014/0125987 A1 | 5/2014 | Flanders | |
| 2014/0180034 A1 | 6/2014 | Hoseit et al. | |
| 2014/0185054 A1 | 7/2014 | Atia et al. | |
| 2014/0200446 A1 | 7/2014 | Haider | |
| 2014/0257087 A1 | 9/2014 | Elbasiony et al. | |
| 2014/0296693 A1 | 10/2014 | Binder et al. | |
| 2014/0356876 A1 | 12/2014 | Ragan | |
| 2014/0368827 A1 | 12/2014 | Fujii | |
| 2015/0011895 A1 | 1/2015 | Johnstone et al. | |
| 2015/0077760 A1 | 3/2015 | Koerner et al. | |
| 2015/0099979 A1* | 4/2015 | Caves | A61B 5/0044 600/475 |
| 2015/0099984 A1 | 4/2015 | Kankaria | |
| 2015/0109623 A1 | 4/2015 | Abdulhalm et al. | |
| 2015/0133778 A1 | 5/2015 | Barriga Rivera et al. | |
| 2015/0141847 A1* | 5/2015 | Sarvazyan | A61B 5/0084 600/478 |
| 2015/0160124 A1 | 6/2015 | Ho et al. | |
| 2015/0216407 A1 | 8/2015 | Huang et al. | |

FOREIGN PATENT DOCUMENTS

| | | |
|---|---|---|
| DE | 02514501 A | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61501068 | 9/1984 |
| JP | 10-24051 A | 1/1989 |
| JP | 11-47150 A | 6/1989 |
| JP | 65502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |

(56) References Cited

FOREIGN PATENT DOCUMENTS

| | | |
|---|---|---|
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/045589 | 6/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |

OTHER PUBLICATIONS

Chung et al., "Clinical Experience of Sutureless Closed Hemontoidectomy with LigaSure" Diseases of the Colon & Rectum vol. 46, No. Jan. 1, 2003, pp. 87-92.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003. (1 page).
Peterson et al. "Comparison of Healing Process Following Ligation with Sutures and Bipolar Vessel Sealing" Surgical Technology International (2001). (8 pages).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
E. David Crawford "Evaluation of a New Vessel Sealing Device in Urologic Cancer Surgery" Sales/Product Literature 2000. (1 page).
Johnson et al. "Evaluation of the LigaSure Vessel Sealing System in Hemorrhoidectormy" American College of Surgeons (ACS) Clinicla Congress Poster (2000). (1 page).
Muller et al., "Extended Left Hemicolectomy Using the LigaSure Vessel Sealing System" Innovations That Work, Sep. 1999. (4 pages).
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002. (4 pages).
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002. (4 pages).
Koyle et al., "Laparoscopic Palomo Varicocele Ligation in Children and Adolescents" Pediatric Endosurgery & Innovative Techniques, vol. 6, No. 1, 2002, pp. 15-19.
W. Scott Helton, "LigaSure Vessel Sealing System: Revolutionary Hemostasis Product for General Surgery"; Sales/Product Literature 1999. (1 page).
LigaSure Vessel Sealing System, the Seal of Confidence in General, Gynecologic, Urologic, and Laparaoscopic Surgery; Sales/Product Literature; Apr. 2002. (8 pages).
Joseph Ortenberg "LigaSure System Used in Laparoscopic 1st and 2nd Stage Orchiopexy" Innovations That Work, Nov. 2002. (4 pages).
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466 .
Olsson et al. "Radical Cystectomy in Females" Current Surgical Techniques in Urology, vol. 14, Issue 3, 2001. (8 pages).
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003, pp. 147-151.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001. (1 page).
Seyfan et al. "Sutureless Closed Hemorrhoidectomy: A New Technique" Annals of Surgery vol. 234 No. 1, Jul. 2001 pp. 21-24.
Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004. (1 page).

(56) References Cited

OTHER PUBLICATIONS

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000. (1 page).
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000. (4 pages).
Levy et al. " Use of a New Energy-based Vessel Ligation Device During Vaginal Hysterectomy" Int'l Federation of Gynecology and Obstetrics (FIGO) World Congress 1999. (1 page).
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000. (1 page).
Jarrett et al., "Use of the LigaSure Vessel Sealing System for Peri-Hilar Vessels in Laparoscopic Nephrectomy" Sales/Product Literature 2000. (1 page).
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.. (1 page).
McLellan et al. "Vessel Sealing for Hemostasis During Gynecologic Surgery" Sales/Product Literature 1999. (1 page).
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed Dec. 17, 2008; inventor: Paul R. Sremeich.
Heniford et al. "Initial Research and Clinical Results with an Electrothermal Bipolar Vessel Sealer" Oct. 1999. (1 page).
European Search Report dated Jan. 13, 2017, issued in EP Application No. 14804636.

* cited by examiner

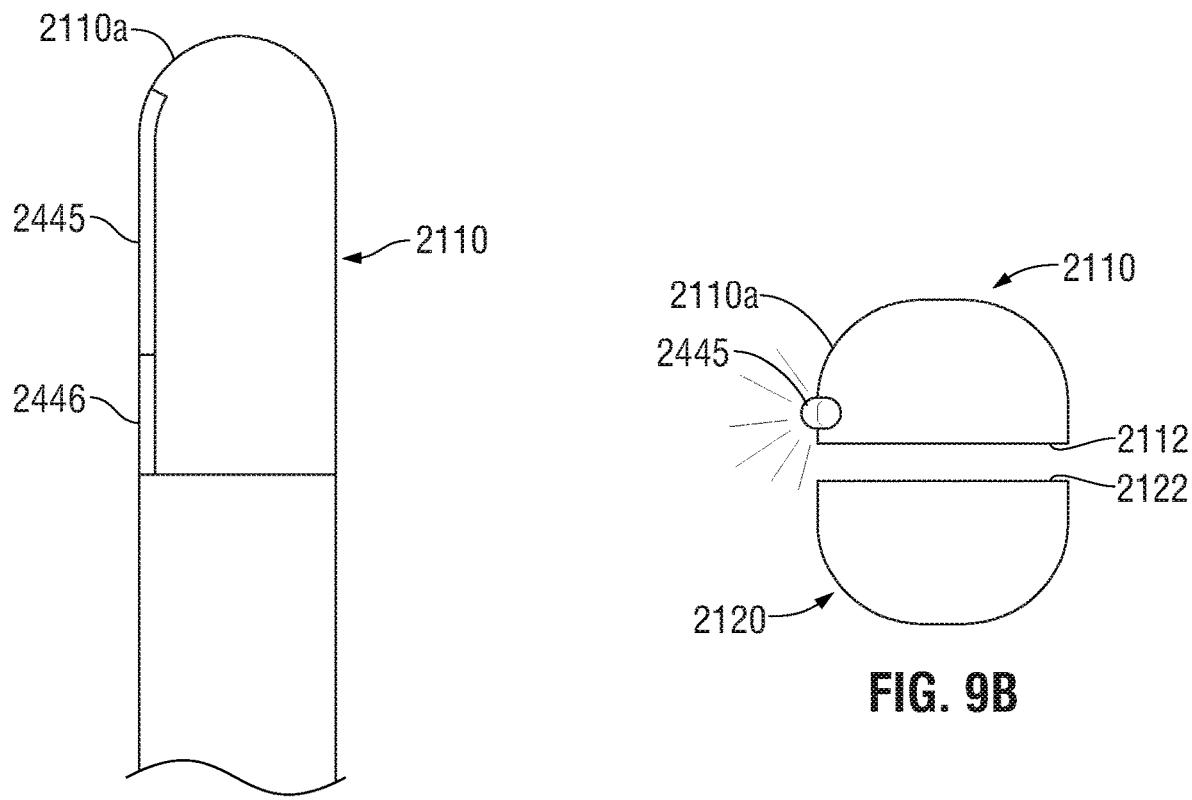
FIG. 9A
FIG. 9B
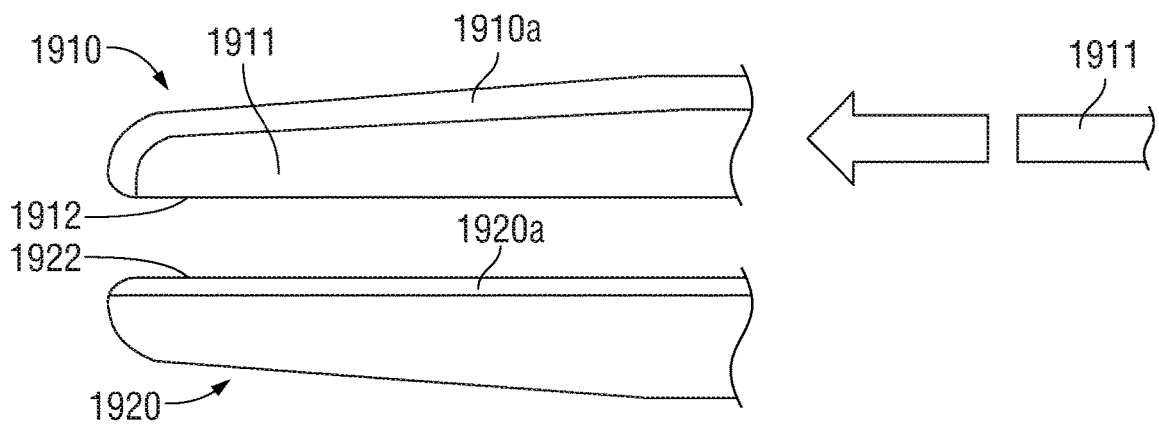
FIG. 10

2 mm

SURGICAL DEVICE WITH AN END-EFFECTOR ASSEMBLY AND SYSTEM FOR MONITORING OF TISSUE DURING A SURGICAL PROCEDURE

CROSS-REFERENCE TO RELATED APPLICATIONS

The present application is a 371 of International PCT/US2014/040505 filed on Jun. 2, 2014, which claims priority to, and the benefit of, U.S. Provisional Application Ser. No. 61/829,420, filed on May 31, 2013, and U.S. Provisional Application Ser. No. 61/839,606, filed on Jun. 26, 2013, the disclosures of which are herein incorporated by reference in their entireties.

BACKGROUND

Technical Field

The present disclosure relates to surgical forceps having components to treat tissue and/or monitor tissue treatment. More particularly, the present disclosure relates to open or endoscopic surgical forceps adapted to treat tissue and/or to sense tissue properties, and methods and systems for monitoring (e.g., optical, thermal, and/or electrical) of tissue during a surgical procedure.

Description of Related Art

In many surgical procedures, body vessels, e.g., blood vessels, ducts, adhesions, fallopian tubes, or the like are sealed to defunctionalize or close the vessels. Traditionally, staples, clips or sutures have been used to close a body vessel. However, these traditional procedures often leave foreign body material inside a patient. In an effort to reduce foreign body material left within the patient and to more effectively seal the body vessel, energy techniques that seal or fuse tissue by heating the tissue have been employed.

The process of radio-frequency (RF) tissue fusion involves clamping the tissue between two electrodes while holding opposing tissue faces under pressure. A controlled RF voltage is then applied so that the RF current generates heat, and tissue transformations such as denaturation and dehydration are induced by the combined heat and pressure.

Endoscopic or open forceps are particularly useful for sealing since forceps utilize mechanical action to constrict, grasp, dissect and/or clamp tissue. Current vessel-sealing procedures utilize RF treatment to heat and desiccate tissue causing closure and sealing of vessels or tissue. Other treatment methods are known in the art; however, very few surgical instruments have the capability to treat tissue and monitor tissue treatment without the use of additional surgical instruments.

SUMMARY

Tissue variability is a key challenge in energy-based therapies and surgical procedures with energy-based devices. Improved treatment methods may depend on a better understanding of the tissue modifications that occur, not only allowing the development of effective energy-delivery strategies but also enabling real-time feedback control to control the tissue fusion procedure.

In accordance with an aspect of the present disclosure, a medical instrument is provided. The medical instrument includes a housing and a shaft coupled to the housing. The shaft has a proximal end and a distal end. An end-effector assembly is disposed at the distal end of the shaft. The end-effector assembly includes first and second jaw members. At least one of the first and second jaw members is movable from a first position wherein the first and second jaw members are disposed in spaced relation relative to one another to at least a second position closer to one another wherein the first and second jaw members cooperate to grasp tissue therebetween. The medical instrument also includes one or more light-emitting elements coupled to either one or both of the first and second jaw members. The one or more light-emitting elements are adapted to deliver light energy to tissue grasped between the first and second jaw members. The medical instrument also includes one or more light-detecting elements configured to generate one or more signals indicative of tissue florescence.

In accordance with another aspect of the present disclosure, a medical instrument is provided and includes a housing, a shaft coupled to the housing, and an end-effector assembly disposed at the distal end of the shaft. The end-effector assembly includes first and second jaw members. At least one of the first and second jaw members is movable from a first position wherein the first and second jaw members are disposed in spaced relation relative to one another to at least a second position closer to one another wherein the first and second jaw members cooperate to grasp tissue therebetween. The medical instrument also includes one or more light-emitting elements coupled to either one or both of the first and second jaw members. The one or more light-emitting elements are adapted to deliver light energy to tissue grasped between the first and second jaw members. The medical instrument also includes a controller configured to control energy delivered to tissue based on the one or more signals indicative of tissue florescence.

In accordance with another aspect of the present disclosure, a system for treating tissue is provided and includes a medical instrument. The medical instrument includes a housing and a shaft coupled to the housing. The shaft has a proximal end and a distal end. An end-effector assembly is disposed at the distal end of the shaft. The end-effector assembly includes first and second jaw members. At least one of the first and second jaw members is movable from a first position wherein the first and second jaw members are disposed in spaced relation relative to one another to at least a second position closer to one another wherein the first and second jaw members cooperate to grasp tissue therebetween. A first tissue-contacting surface is associated with the first jaw member. A second tissue-contacting surface is associated with the second jaw member. One or more light-emitting elements are coupled to one or both of the first and second jaw members. The one or more light-emitting elements are adapted to deliver light energy to tissue grasped between the first and second jaw members. The medical instrument includes one or more light-detecting elements configured to sense one or more properties of the light energy passing through the tissue, and a controller coupled to the one or more light-detecting elements and the one or more light-emitting elements. The controller is configured to control energy delivered to tissue disposed between the first and second tissue-contacting surfaces during activation based on the one or more properties of the light energy sensed by the one or more light-detecting elements.

In accordance with another aspect of the present disclosure, a method of treating tissue is provided and includes positioning an end-effector assembly including first and second jaw members at a first position within tissue. Each of the first and second jaw members includes a tissue-contacting surface. At least one of the first and second jaw members is movable from a spaced relation relative to the other jaw member to at least one subsequent position wherein the tissue-contacting surfaces cooperate to grasp tissue therebetween. The method also includes activating a light-emitting element associated with one or both of the first and second jaw members to emit light into tissue and evaluating one or more characteristics of the tissue based on a response to light entering the tissue.

As used herein, the term "treat" refers to performing a surgical treatment to tissue including, but not limited to heating, sealing, cutting, sensing and/or monitoring. As used herein, the term "light energy source" refers broadly to include all types of devices that produce light for medical use (e.g., tissue treatment). These devices include lasers, light-emitting diodes (LEDs), lamps, and other devices that produce light anywhere along an appropriate part of the electromagnetic spectrum (e.g., from infrared to ultraviolet). It is also to be understood that the light sources disposed herein may be used interchangeably, such that, if an LED light source is disclosed, a laser light source may also be used, unless stated otherwise.

Various embodiments of the present disclosure provide systems and methods for treating tissue (and/or monitoring of tissue) by delivering light thereto. This may be accomplished by placing a light source in intimate contact with the target tissue. In some embodiments, it may be accomplished by connecting a light source to the target tissue with an optical system designed to transmit the light from the light source to the tissue. Either system may include elements that shape the distribution of optical energy as it impinges on and interacts with the target tissue. As herein, the term "light-emitting elements" denotes any device from which light exits prior to interacting with the target tissue including but not limited to: light sources; the end of a light transmission system terminating at the target tissue; and/or refracting, diffracting, transmitting or reflecting optical elements such as lenses, diffraction gratings, windows and mirrors, and combinations thereof.

In general, the term "laser light source" is interchangeable, in this disclosure, with the terms "laser source," "excitation light source" and "excitation source." Laser light sources may produce light having a wavelength from about 200 nanometers (nm) to about 15,000 nm and include but are not limited to ruby lasers, tunable titanium-sapphire lasers, copper vapor lasers, carbon dioxide lasers, alexandrite lasers, argon lasers such as argon fluoride (ArF) excimer lasers, argon-dye lasers, potassium titanyl phosphate (KTP) lasers, krypton lasers such as krypton fluoride (KrF) excimer lasers, neodymium:yttrium-aluminum-garnet (Nd:YAG) lasers, holmium:yttrium-aluminum-garnet (Ho:YAG) lasers, erbium:yttrium-aluminum-garnet (Er:YAG) lasers, diode lasers, fiber lasers, xenon chloride (XeCl) excimer lasers, tunable thalium lasers, and combinations thereof. Additional light source types also include fiber optic light sources and deuterium light sources.

In some aspects of the present disclosure, light may be generated at multiple wavelengths. For example, Nd:YAG and KTP lasers may be part of a single light source. Nd:YAG with a greater optical depth in tissue may be used for sealing, and KTP with a shorter optical depth may be used for sealing smaller vessels, thinner tissue, or for cutting. As used herein, the term "receiving module" refers to a component or apparatus having the capability of receiving and/or sensing a signal (e.g., light energy and heat energy) and generating an output signal (e.g., indication to a user, control information, parameter setting instruction, etc.). This may occur by analyzing the received signal to generate one or more control signals. In some embodiments, based on the one or more control signals, a controller may adjust operating parameters of an energy source (e.g., laser source, RF generator, etc.) and/or perform other control functions, alarming functions, or other functions in association therewith. The receiving module may also transmit the received signal to some other suitable component (e.g., processor, signal analyzing unit, and/or generator) for signal processing, analysis, etc.

As described in more detail below with reference to the accompanying figures, the present disclosure generally relates to surgical energy-based devices that include an end-effector assembly configured to fuse (e.g., seal) and/or separate (e.g., cut) tissue. The present disclosure also provides one or more devices configured to sense and/or monitor tissue and/or energy properties (e.g., tissue impedance, tissue temperature, and tissue fluorescence) at various stages of treatment to determine when the treatment is complete, efficacy of a tissue seal, and/or to measure jaw pressure. Optical sensing provides a better indication of seal quality than existing methods such as electrical impedance measurements. In some embodiments, tissue separation may be accomplished with the same light energy device used for tissue sealing, which eliminates the need for a separate mechanical blade that is traditionally used for tissue separation in jaw members. The present disclosure also provides methods for providing feedback to the user, generator, controller and/or control algorithm with regard to temperature of tissue, electrical impedance of tissue, temporal profile of tissue fluorescence features, jaw closure pressure, jaw positioning, and/or other various feedback information, e.g., using Raman spectroscopy, Raman maps, fluorescence spectroscopy, and/or laser-induced tissue fluorescence. In some embodiments, fluorescence data may be used for optimization of the RF energy delivery protocol to avoid excessive tissue thermal damage and/or incomplete tissue fusions.

Any of the following aspects and components thereof of the present disclosure may be interchangeably combined with one or more other embodiments. For example, various disclosed methods and systems for monitoring of tissue and control processes may be utilized with various jaw member embodiments.

BRIEF DESCRIPTION OF THE DRAWINGS

Objects and features of the presently-disclosed surgical device with an end-effector assembly and the method and system for monitoring of tissue during a surgical procedure will become apparent to those of ordinary skill in the art when descriptions of various embodiments thereof are read with reference to the accompanying drawings, of which:

FIG. 9A is a top view of a jaw member including a light dissection element disposed on an outer periphery thereof in accordance with an embodiment of the present disclosure;

FIG. 9B is a front, cross-sectional of a jaw member including a light dissection element disposed on an outer periphery thereof in accordance with an embodiment of the present disclosure;

FIG. 10 is a side, cross-sectional view of an end-effector assembly in accordance with another embodiment of the present disclosure;

DETAILED DESCRIPTION

Figure 1A:
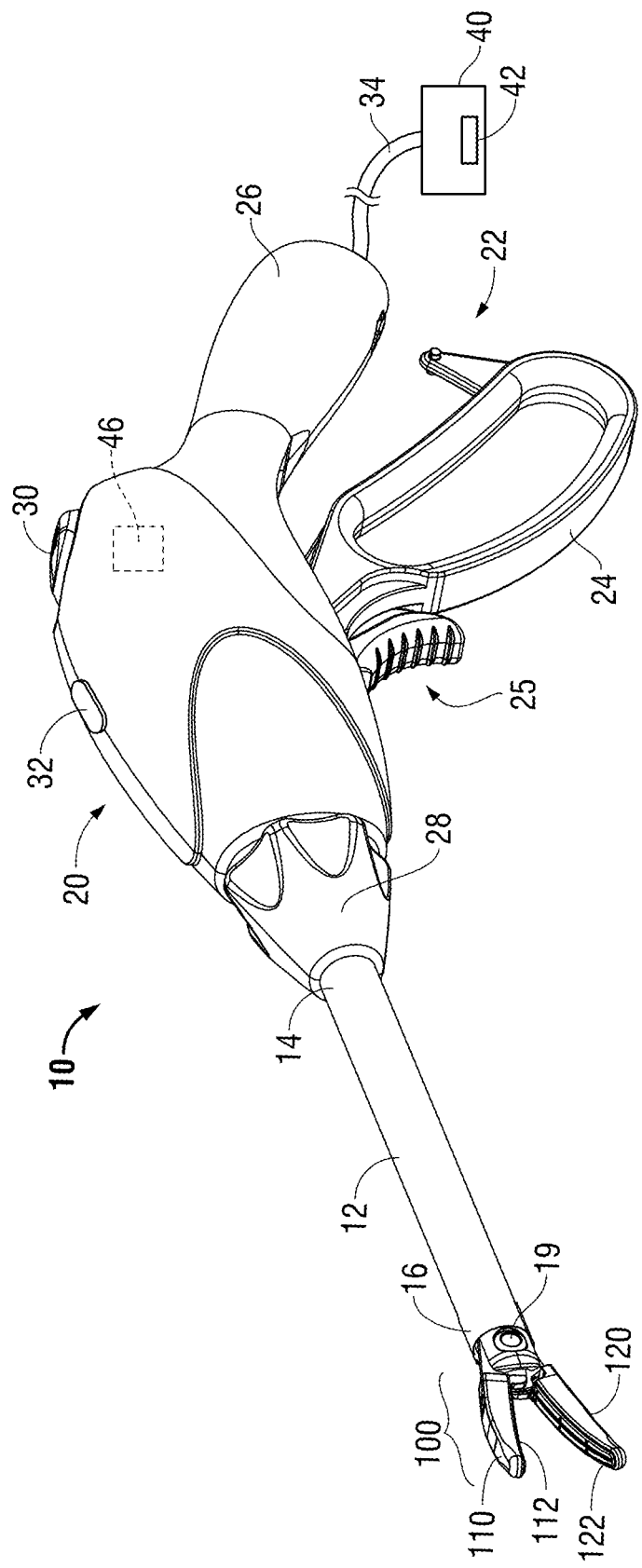
FIG. 1A is a perspective view of an endoscopic forceps having an end-effector assembly coupled to the distal end of the forceps in accordance with an embodiment of the present disclosure.

Hereinafter, embodiments of surgical devices with an end-effector assembly and methods and systems for monitoring of tissue during a surgical procedure of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure.

As it is used in this description, "transmission line" generally refers to any transmission medium that can be used for the propagation of signals from one point to another. A transmission line may be, for example, a wire, a two-wire line, a coaxial wire, a waveguide, a fiber optic line and/or fiber optic bundles.

As it is used herein, "computer" generally refers to anything that transforms information in a purposeful way. Examples of a computer may include: a computer; a personal computer (PC); a portable computer; a laptop computer; a computer having a single processor, multiple processors, or multi-core processors, which may operate in parallel and/or not in parallel; a general purpose computer; a supercomputer; a mainframe; a super mini-computer; a mini-computer; a workstation; a micro-computer; a server; a web appliance; a hybrid combination of a computer and an interactive television; a tablet personal computer; a personal digital assistant (PDA); application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, or a chip set; a system on a chip (SoC), or a multiprocessor system-on-chip (MPSoC); an optical computer; a quantum computer; a biological computer; and an apparatus that may accept data, may process data in accordance with one or more stored software programs, and may generate results. For the purposes of this description, the terms "software" and "code" should be interpreted as being applicable to software, firmware, or a combination of software and firmware.

Various embodiments of the present disclosure provide surgical instruments suitable for sealing, cauterizing, coagulating, desiccating, and/or cutting tissue, e.g., vessels and vascular tissue, during a surgical procedure. Embodiments of the presently-disclosed surgical instruments may be configured to provide light energy, which may be suitable for sealing, cauterizing, coagulating, desiccating, and/or cutting tissue. The light energy may be provided in different forms, including but not limited to lasers, light-emitting diode, and any other suitable type of light energy. Embodiments of the presently-disclosed surgical instruments may be configured to provide monopolar electrosurgical energy and/or bipolar electrosurgical energy, which may be suitable for sealing, cauterizing, coagulating, desiccating, and/or cutting tissue, e.g., vessels and vascular tissue. Embodiments of the presently-disclosed surgical instruments may be suitable for utilization in endoscopic surgical procedures and/or suitable for utilization in open surgical applications.

Embodiments of the presently-disclosed surgical instruments may be implemented using a variety of types of energy, e.g., surgical energy at radio frequencies (RF) and/or at other frequencies, optical, and/or thermal energy. Embodiments of the presently-disclosed surgical instruments may be configured to be connectable to one or more energy sources, e.g., laser sources, RF generators, and/or self-contained power sources. Embodiments of the presently-disclosed surgical instruments may be connected through a suitable bipolar cable and/or other transmission line to an electrosurgical generator and/or other suitable energy source, e.g., laser light source.

The Raman spectroscopy method described herein provides direct insights into tissue constituent and structure changes on the molecular level, exposing spectroscopic evidences of the migration of collagen fibers between tissue layers as well as the denaturing of collagen and restructuring of collagen crosslinks post fusion. Various embodiments described herein utilize these insights to provide a better understanding of the intrinsic mechanisms for tissue fusion and to provide optical feedback-control methods for heat-induced tissue fusion and improved control methods for tissue fusion procedures in accordance with the present disclosure.

Figure 1B:
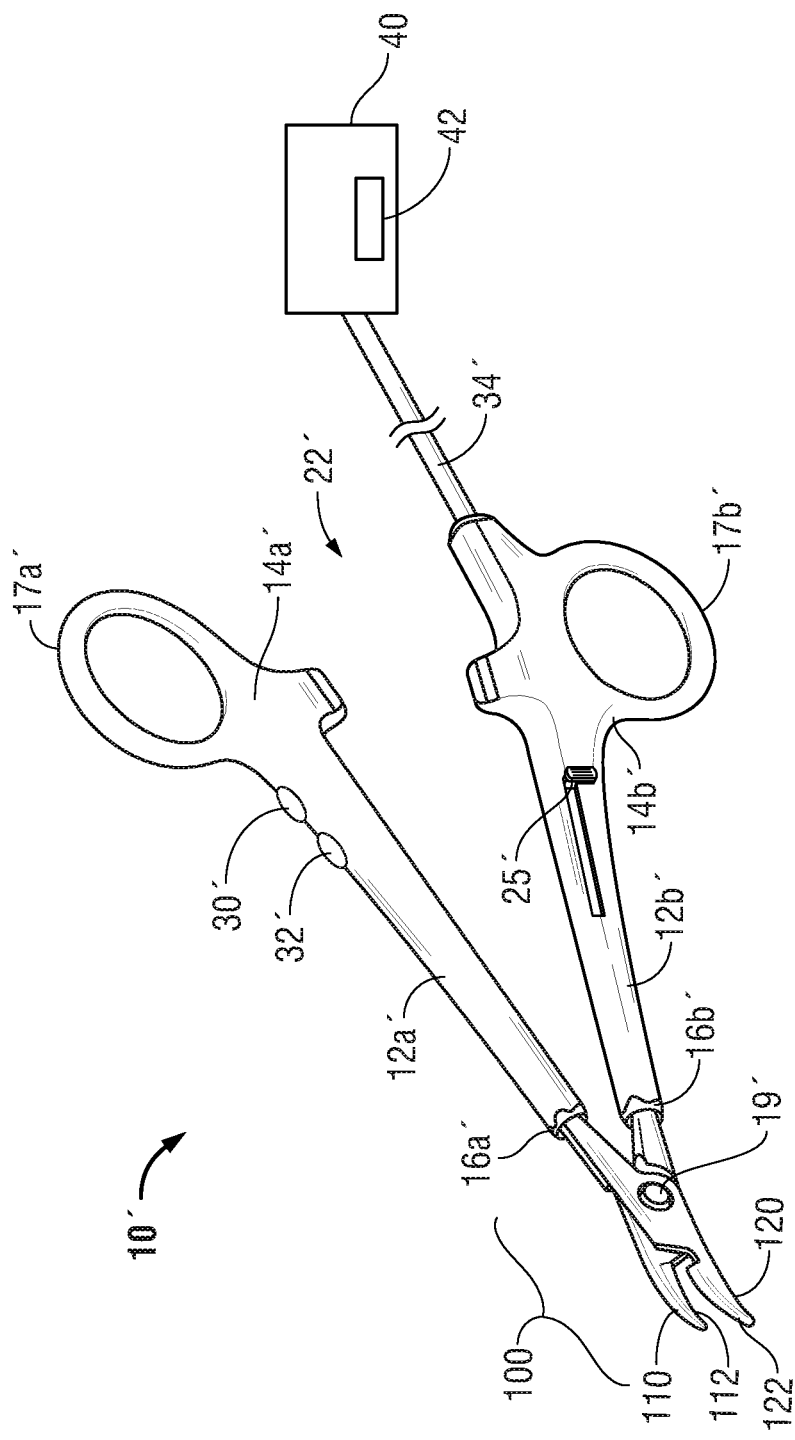
FIG. 1B is a perspective view of an open forceps having a handle assembly and an end-effector assembly coupled to the distal end of the handle assembly in accordance with an embodiment of the present disclosure.

The real-time multi-wavelength laser-induced fluorescence spectroscopy system described herein FIG. 1A depicts an embodiment of a forceps for use in connection with endoscopic surgical procedures, and an embodiment of an open version of a forceps is shown in FIG. 1B.

For the purposes herein, either an endoscopic instrument or an open surgery instrument may be utilized with any of the embodiments of end-effector assemblies described herein. It should be noted that different electrical, optical and mechanical connections and other considerations may apply to each particular type of instrument. However, aspects with respect to the end-effector assembly and the operating characteristics thereof remain generally consistent with respect to both the endoscopic or open surgery designs.

Various embodiments of the present disclosure provide an apparatus, system and method for sealing tissue using light energy. Light (e.g., with a wavelength range of from about 200 nm to about 11,000 nm) is used to heat tissue due to the absorption of light into the tissue. Absorption, transmittance, and scattering of light energy depends on the tissue, the state of the tissue (e.g., hydration, disease state, treatment stage, etc.), and the wavelength of the light. In accordance with some embodiments of the present disclosure, these factors are utilized to control the distribution of the energy within the tissue based on an appropriate choice of the wavelength. More specifically, wavelengths that are strongly absorbed by the tissue deposit energy closer to the surface of the tissue, and wavelengths that are weakly absorbed by the tissue are used to deposit a larger fraction of the incident energy deeper in the tissue. In particular, since tissue is relatively transparent to light at certain infrared wavelengths, light energy at infrared frequencies may be used for deeper energy deposition.

In FIGS. 1A and 1B, surgical instruments (generally referred to herein as forceps 10 and open forceps 10') are shown for use with various surgical procedures. Forceps 10 and open forceps 10' may include additional, fewer, or different components than shown in FIGS. 1A and 1B, depending upon a particular purpose or to achieve a desired result.

Forceps 10 includes a transmission line 34, which may connect directly to a light energy source (e.g., energy source 40) for generating light energy adapted to treat tissue. Transmission line 34 (also referred to herein as "cable 34") may be formed from a suitable flexible, semi-rigid, or rigid cable. Cable 34 may be internally divided into one or more cable leads (not shown) each of which transmits energy through their respective feed paths to the end-effector assembly 100. Cable 34 may additionally, or alternatively, include an optical fiber configured to transmit light energy and/or control signals to the end-effector assembly 100.

Energy source 40 may be any generator suitable for use with surgical devices, and may be configured to output various types of energy, e.g., light energy having a wavelength from about 200 nm to about 11,000 nm. Energy source 40 may additionally, or alternatively, be configured to provide RF energy and/or various frequencies of electromagnetic energy.

Energy source 40 may include any laser light source suitable for use with surgical devices. In some embodiments, more than one laser source may be included in the energy source 40, and more than one laser may be used during a surgical procedure. Examples of laser light sources include Thorlabs' diode lasers modules (Thorlabs Inc., Newton, N.J.). Energy source 40 shown in FIG. 1 includes a controller 42, e.g., logic circuit, computer, processor, field programmable gate array, and the like. Controller 42 may include a microprocessor having a memory (not explicitly shown), which may be volatile type memory (e.g., RAM) and/or non-volatile type memory (e.g., flash media, disk media, etc.).

In some embodiments, the controller 42 is configured to provide timing, wavelength, and/or power control of the one or more lasers. Energy source 40 may include one or more mechanisms for laser selection, filtering, temperature compensation, and/or Q-switching operations. In some embodiments, the energy source 40 may include a function generator and optical shutter used to modulate a continuous-wave laser to generate pulsed output. Various embodiments of the forceps 10 utilizing the aforementioned light energy are discussed in more detail below.

In some embodiments, wherein the energy source 40 is configured to provide RF energy, the controller 42 may additionally, or alternatively, utilize one or more signals indicative of conditions and/or operational parameters (e.g., tissue impedance, temperature, jaw member opening angle, force applied to tissue, thickness of tissue, and/or and tissue fluorescence) to adjust one or more operating parameters associated with the energy source 40 (e.g., duration of application of RF energy, mode of operation, power, current, and voltage) and/or instruct the energy source 40 to perform other control functions, alarming functions, or other functions in association therewith. Examples of generators that may be suitable for use as a source of RF energy are commercially available under the trademarks FORCE EZ™ FORCE FX™, and FORCE TRIAD™ offered by Covidien Surgical Solutions of Boulder, Colo.

Forceps 10 is configured to support an end-effector assembly (e.g., end-effector assembly 100). Forceps 10 includes a housing 20, a handle assembly 22, a trigger assembly 25, a rotatable assembly 28, and end-effector assembly 100. End-effector assembly 100 may include any feature or combination of features of the jaw member embodiments disclosed herein. One or more components of the forceps 10, e.g., housing 20, rotatable assembly 28, and/or end-effector assembly 100, may be adapted to mutually cooperate to grasp, seal, divide and/or sense tissue, e.g., tubular vessels and vascular tissue. In some embodiments, trigger assembly 25 may be configured to actuate a cutting function of the forceps 10 or to actuate another component, as described in more detail below.

End-effector assembly 100, which is described in more detail later in this disclosure, generally includes two jaw members 110 and 120 disposed in opposing relation relative to one another. One or both of the jaw members 110 and 120 are movable from a first position wherein the jaw members 110 and 120 are disposed in spaced relation relative to one another to a second position wherein the jaw members 110 and 120 cooperate to grasp tissue therebetween.

Forceps 10 includes an elongated shaft 12 having a distal portion 16 configured to mechanically engage end-effector assembly 100. The proximal end 14 of shaft 12 is received within housing 20, and connections relating thereto are shown and described in commonly-assigned U.S. Pat. No. 7,150,097 entitled "Method Of Manufacturing Jaw Assembly For Vessel Sealer And Divider," commonly-assigned U.S. Pat. No. 7,156,846 entitled "Vessel Sealer And Divider For Use With Small Trocars And Cannulas," commonly-assigned U.S. Pat. No. 7,597,693 entitled "Vessel Sealer And Divider For Use With Small Trocars And Cannulas," and commonly-assigned U.S. Pat. No. 7,771,425 entitled "Vessel Sealer And Divider Having A Variable Jaw Clamping Mechanism," the disclosures of which are herein incorporated by reference in their entireties. Rotatable assembly 28 is mechanically associated with shaft 12 such that rotational movement of rotatable assembly 28 imparts similar rotational movement to shaft 12 that, in turn, rotates end-effector assembly 100.

Handle assembly 22 includes a fixed handle 26 and a movable handle 24. In some embodiments, the fixed handle 26 is integrally associated with the housing 20, and the movable handle 24 is selectively movable relative to the fixed handle 26. Movable handle 24 of the handle assembly 22 is ultimately connected to the drive assembly (not shown). As can be appreciated, applying force to move the movable handle 24 toward the fixed handle 26 pulls a drive sleeve (not shown) proximally to impart movement to the jaw members 110 and 120 from an open position, wherein the jaw members 110 and 120 are disposed in spaced relation relative to one another, to a clamping or closed position, wherein the jaw members 110 and 120 cooperate to grasp tissue therebetween. Examples of handle assembly embodiments of the forceps 10 are described in the above-mentioned, commonly-assigned U.S. Pat. Nos. 7,150,097, 7,156, 846, 7,597,693 and 7,771,425.

In some embodiments, the end-effector assembly 100 is configured as a unilateral assembly that includes a stationary jaw member (e.g., jaw member 120) mounted in fixed relation to the shaft 12 and a pivoting jaw member (e.g., jaw member 110) movably mounted about a pin 19. Jaw members 110 and 120 may be curved at various angles to facilitate manipulation of tissue and/or to provide enhanced line-of-sight for accessing targeted tissues. Alternatively, the forceps 10 may include a bilateral assembly, i.e., both jaw members 110 and 120 move relative to one another.

Figure 2A:
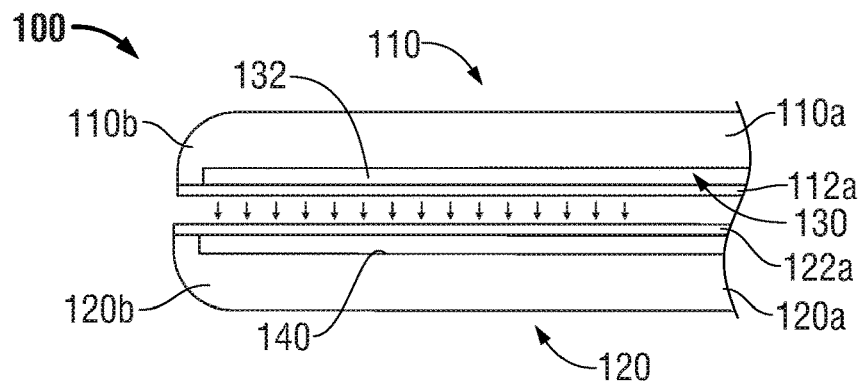
FIG. 2A is a side, cross-sectional view of an end-effector assembly in accordance with an embodiment of the present disclosure.
Figure 2B:
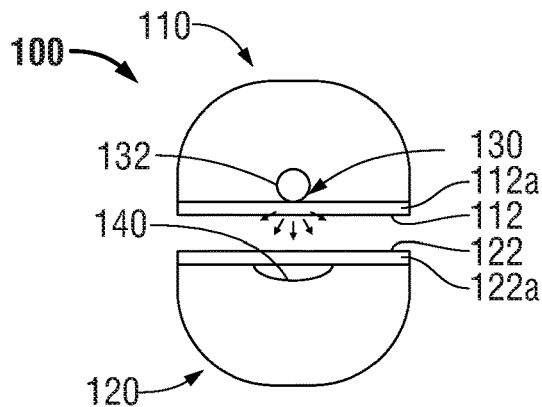
FIG. 2B is a front, cross-sectional view of the end-effector assembly of FIG. 2A.

Jaw members 110 and 120, as shown for example in FIG. 2B, include a tissue-contacting surface 112 and 122, respectively, arranged in opposed relation relative to one another. Tissue-contacting surfaces 112 and 122 cooperate to grasp and seal tissue held therebetween upon application of energy from energy source 40. In some embodiments, tissue-contacting surfaces 112 and 122 are connected to the energy source 40 such that light energy can be transmitted to and/or through the tissue held therebetween.

First and second switch assemblies 30 and 32 are configured to selectively provide light energy to end-effector assembly 100. More particularly, the first switch assembly 30 may be configured to perform a first type of surgical procedure (e.g., seal, cut, and/or sense) and a second switch assembly 32 may be configured to perform a second type of surgical procedure (e.g., seal, cut, and/or sense). It should be noted that the presently-disclosed embodiments may include any number of suitable switch assemblies and are not limited to only switch assemblies 30 and 32. It should further be noted that the presently-disclosed embodiments may be configured to perform any suitable surgical procedure and are not limited to only sealing, cutting and sensing.

Forceps 10 generally includes a controller 46. In some embodiments, as shown in FIG. 1, the controller 46 is formed integrally with the forceps 10. In other embodiments, the controller 46 may be provided as a separate component coupled to the forceps 10. Controller 46 may include any type of computing device, computational circuit, or any type of processor or processing circuit capable of executing a series of instructions that are stored in a memory. Controller 46 may be configured to control one or more operating parameters associated with the energy source 40 based on one or more signals indicative of user input, such as generated by the first and second switch assemblies 30 and 32 and/or one or more separate, user-actuatable buttons or switches. Examples of switch configurations that may be suitable for use with the forceps 10 include, but are not limited to, pushbutton, toggle, rocker, tactile, snap, rotary, slide and thumbwheel. In some embodiments, the forceps 10 may be selectively used in either a monopolar mode or a bipolar mode by engagement of the appropriate switch.

First and second switch assemblies 30 and 32 may also cooperate with the controller 42, which may be configured to automatically trigger one of the switches to change between a first mode (e.g., sealing mode) and a second mode (e.g., cutting mode) upon the detection of one or more parameters or thresholds. In some embodiments, the controller 42 (and/or the controller 46) is configured to receive feedback information, including various sensor feedback with regard to temperature of tissue, electrical impedance of tissue, jaw closure pressure, jaw positioning, and/or other various feedback information, e.g., using Raman spectroscopy, Raman maps, fluorescence spectroscopy, and/or laser-induced tissue fluorescence, and to control the energy source 40 based on the feedback information.

Embodiments of the present disclosure allow the jaw members 110 and 120 to seal and/or cut tissue using light energy. In some embodiments, the controller 42 may include a feedback loop that indicates when a tissue seal is complete based upon one or more of the following parameters: tissue temperature, optical sensing, change in impedance of the tissue over time and/or changes in the optical or electrical power or current applied to the tissue over time, rate of change of these properties and combinations thereof. An audible or visual feedback monitor may be employed to convey information to the surgeon regarding the overall seal quality and/or the completion of an effective tissue seal.

Referring now to FIG. 1B, an open forceps 10' is depicted and includes end-effector assembly 100 (similar to forceps 10) that is attached to a handle assembly 22' that includes a pair of elongated shaft portions 12a' and 12b'. Each elongated shaft portion, 12a' and 12b', respectively, has a proximal end 14a' and 14b', respectively, and a distal end 16a' and 16b', respectively. The end-effector assembly 100 includes jaw members 110 and 120 coupled to distal ends 16a' and 16b' of shafts 12a' and 12b', respectively. The jaw members 110 and 120 are connected about pivot pin 19' that allows jaw members 110 and 120 to pivot relative to one another from the first to second positions for treating tissue (as described above). Tissue-contacting surfaces 112 and 122 are connected to opposing jaw members 110 and 120.

Each shaft 12a' and 12b' includes a handle 17a' and 17b', respectively, disposed at the proximal end 14a' and 14b' thereof. Handles 17a' and 17b' facilitate movement of the shafts 12a' and 12b' relative to one another which, in turn, pivot the jaw members 110 and 120 from the open position wherein the jaw members 110 and 120 are disposed in spaced relation relative to one another to the clamping or closed position wherein the jaw members 110 and 120 cooperate to grasp tissue therebetween.

In some embodiments, one or both of the shafts, e.g., shaft 12a', includes a first switch assembly 30' and a second switch assembly 32'. First and second switch assemblies 30' and 32' may be configured to selectively provide energy to the end-effector assembly 100. More particularly, the first switch assembly 30' may be configured to perform a first type of surgical procedure (e.g., seal, cut, or sense) and second switch assembly 32' may be configured to perform a second type of surgical procedure (e.g., seal, cut, or sense). In some embodiments, both or one of the shafts, e.g., shaft 12b', may include a trigger assembly 25' for actuation of an additional laser fiber (e.g., laser fiber 230a and/or 230b shown in FIG. 3).

With continued reference to FIG. 1B, forceps 10' is depicted having a cable 34' that connects the forceps 10' to energy source 40. In some embodiments, cable 34' is internally divided within the shaft 12b' to transmit light energy through various transmission paths to one or more components of end-effector assembly 100.

FIGS. 2A and 2B illustrate an end-effector assembly 100 according to an embodiment of the present disclosure, which is configured for use with either instrument 10 or instrument 10', discussed above or any other suitable surgical instrument. However, for purposes of simplicity and consistency, end-effector assembly 100 is described hereinbelow with reference to instrument 10.

In some embodiments, as shown for example in FIGS. 2A and 2B, jaw members 110 and 120 include proximal ends 110a and 120a, respectively, distal ends 110b and 120b, respectively, and a groove or channel 130 and 140, respectively, defined therebetween. Jaw member 110 includes a light-diffusing element 132 that is disposed on or along tissue-contacting surface 112. The light-diffusing element 132 may be made from any suitable light diffusing material, such as frosted sapphire crystal. The light-diffusing element 132 is disposed within channel 130. Tissue-contacting surfaces 112 and 122 may include a reflective surface disposed thereon. In some embodiments, the surface includes, but is not limited to polished metal, coating or any other material that is adapted to reflect light.

In other embodiments, tissue-contacting surfaces 112 and 122 may also include a coating or cover 112a and 122a. In some embodiments, the coatings 112a and 122a may be formed from a light absorbing material (e.g., a light absorbent coating), a transparent material, a scattering material, or a reflective material. In some embodiments, the coating 112a may be formed from one material (e.g., a transparent material) while the coating 122a may be formed from a different material (e.g., a light absorbent or reflective material). In some embodiments, the coatings 112a and 122a may both be formed from the same material, such as a reflective material. Providing both tissue-contacting surfaces 112 and 122 with reflective surfaces increases absorption of the light being supplied to the tissue since the light passes multiple times therethrough, which may shorten the treatment time.

In some embodiments, the coatings 112a and 122a may include a gel or another biocompatible film disposed thereon. The gel or the film may include a dye of a specific color designed to absorb light energy at a specific wavelength. In some embodiments, the gel may be applied to the tissue prior to treatment.

In other embodiments, the coatings 112a and 122a are absorbent coatings formed from a thermochromic material configured to increase absorption properties as temperature increases. As used herein, the term "thermochromic" generally refers to any material that changes color in response to a change in temperature. As the temperature of the jaw members 110 and 120 increases during application of energy, the absorbent coatings 112a and 122a become progressively more absorbing and provide more heat to the tissue.

The light-diffusing element 132 may be coupled to energy source 40 via cable 34, which may include one or more a light transporting or light generating fibers therewithin. In some embodiments, the energy source 40 is adapted to generate a light of a desired wavelength from about 200 nm to about 11,000 nm and transmit the light energy along cable 34 to the forceps 10, 10' and, more specifically, to the light-diffusing element 132.

Light-diffusing element 132 may have a substantially cylindrical or conical shape and may be formed from a suitable light conducting material (e.g., sapphire crystal, crystal glass, plastic fiber, and the like). More specifically, the light-diffusing element 132 may be manufactured from any suitable laser or light conducting medium to obtain desired diffusion properties.

Groove 140 may be configured to fit around or about light-diffusing element 132 when the jaw members 110 and 120 are disposed in a closed position. Groove 140 may also have a reflective surface such that light emitted from light-diffusing element 132 may pass through tissue and subsequently be reflected back into tissue to form a desired illumination pattern. In some embodiments, groove 140 may have light absorbing properties and/or include a material having light absorbing properties (e.g., a light absorbent coating). In this manner, when light is absorbed, groove 140 and/or the absorbent material may heat to a suitable temperature to operably treat tissue held between jaw members 110 and 120.

During operation, once tissue is grasped between the tissue-contacting surfaces 112 and 122, laser light is transmitted from the energy source 40 to the light-diffusing element 132, which then emits light energy into the tissue. Since the tissue-contacting surfaces 112 and 122 are adapted to reflect light, the light energy emitted by the light-diffusing element 132 is concentrated in the volume between the jaw members 110 and 120 which in turn, heats up the tissue grasped therebetween without compromising the surrounding tissue. After a preset duration or upon a signal from one or more sensors (described in further detail below), the energy is terminated indicating that the tissue treatment (e.g., seal or cutting) is complete.

Figure 3:
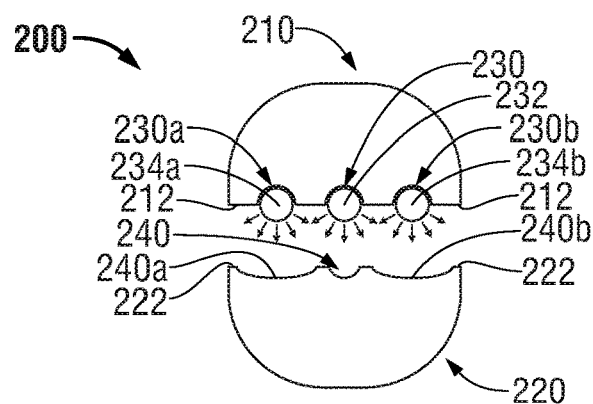
FIG. 3 is a front, cross-sectional view of an end-effector assembly in accordance with another embodiment of the present disclosure.

Referring now to FIG. 3, another embodiment of the presently-disclosed end-effector assembly is shown as end-effector assembly 200. End-effector assembly 200 includes jaw members 210 and 220 having tissue-contacting surfaces 212 and 222. Similar to the above discussed jaw members 110 and 120, jaw members 210 and 220 cooperate to grasp tissue therebetween. Each jaw member 210 and 220 defines channels or grooves disposed therealong. More specifically, jaw member 210 includes grooves 230, 230a, and 230b, and jaw member 220 includes grooves 240, 240a, and 240b. In some embodiments, jaw member 210 includes a plurality of laser light fibers (e.g., laser fiber 232, 234a, and 234b) that span along the length of the jaw member 210 and within respective grooves 230, 230a, and 230b. The laser fibers are configured to emit a laser light between and along the length of jaw members 210 and 220.

Jaw member 210 includes a centrally-positioned laser fiber 232 that is disposed within channel 230. Alongside of channel 230, jaw member 210 also defines channel or grooves 230a and 230b that are laterally positioned from channel 230 and include peripheral laser fibers 234a and 234b. The laser fibers 234a and 234b may be configured for sealing tissue, based on the type of light energy supplied thereto, pressure applied to the jaw members 210 and 220, as well the reflective or absorbing properties of the grooves disposed about the fibers as described in more detail below.

In some embodiments, the tissue-contacting surfaces 212 and 222 may include a transparent coating or cover disposed on the surface thereof, similar to the tissue-contacting surfaces 112 and 122 of FIGS. 2A and 2B. The laser fiber 232 may be configured to cut tissue after an effective seal has been achieved by laser sealing fibers 234a and 234b. In some embodiments, cutting may be performed independent of the sealing. In addition, a reflective groove 240 may be disposed on the jaw member 220 such that when laser light is emitted from laser fiber 232, the laser light is reflected from reflective groove 240 back through tissue forming a desired illumination pattern. Additionally or alternatively, laser fibers 234a and 234b may also have respective reflective or absorbing grooves 240a and 240b within opposing jaw member 220, as described above.

It should be noted that any number of laser fibers may be used in any of the embodiments discussed in the present disclosure to achieve tissue sealing or cutting based on the light energy transmitted through the laser fibers. Similarly, any number of laser cutting fibers (e.g., laser fiber 232) may be used in any of the embodiments discussed in the present disclosure. In some embodiments, a single laser fiber may also be configured to include sealing and cutting capabilities in any of the embodiments of the present disclosure. It should be noted that any one of the laser fibers may be configured to transmit energy at different wavelengths depending on the surgical treatment (e.g., sealing, cutting and/or sensing). In other embodiments, a particular laser or light fiber may be configured to perform a particular surgical treatment (e.g., sealing, cutting and/or sensing). One or more sensors may be employed and/or a feedback circuit may be integrated with respect to end-effector assembly 200 to signal the user after an effective seal and/or effective separation. An automated seal and cut algorithm may also be employed for this purpose that uses a single activation of a switch, e.g., switch 32, to initiate the process.

Figure 4A:
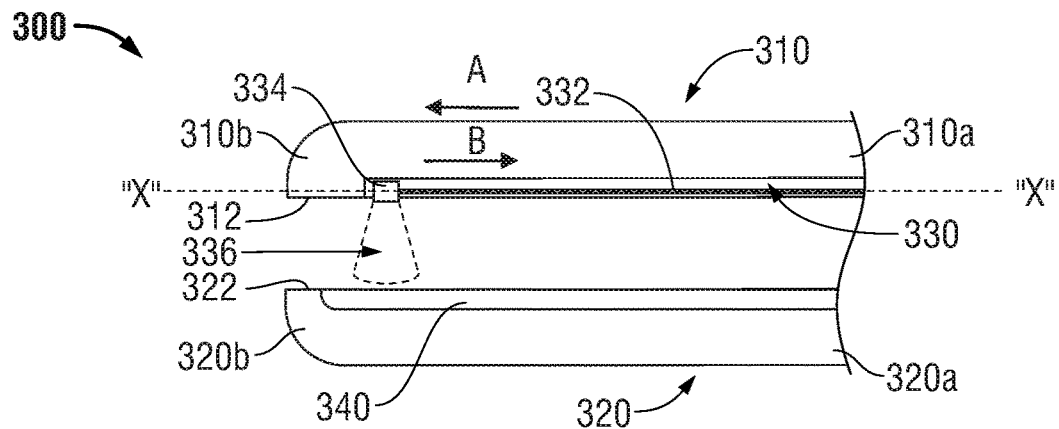
FIG. 4A is a side, cross-sectional view of an end-effector assembly in accordance with another embodiment of the present disclosure.
Figure 4B:
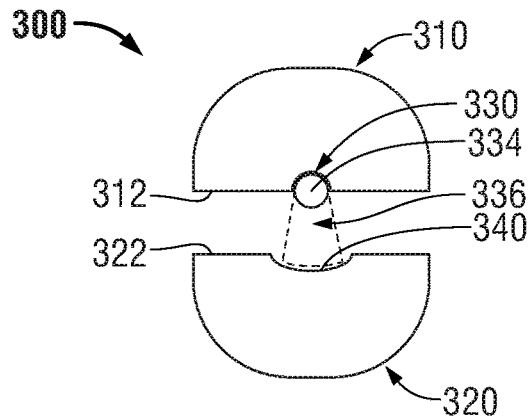
FIG. 4B is a front, cross-sectional view of the end-effector assembly of FIG. 4A.
Figure 4C:
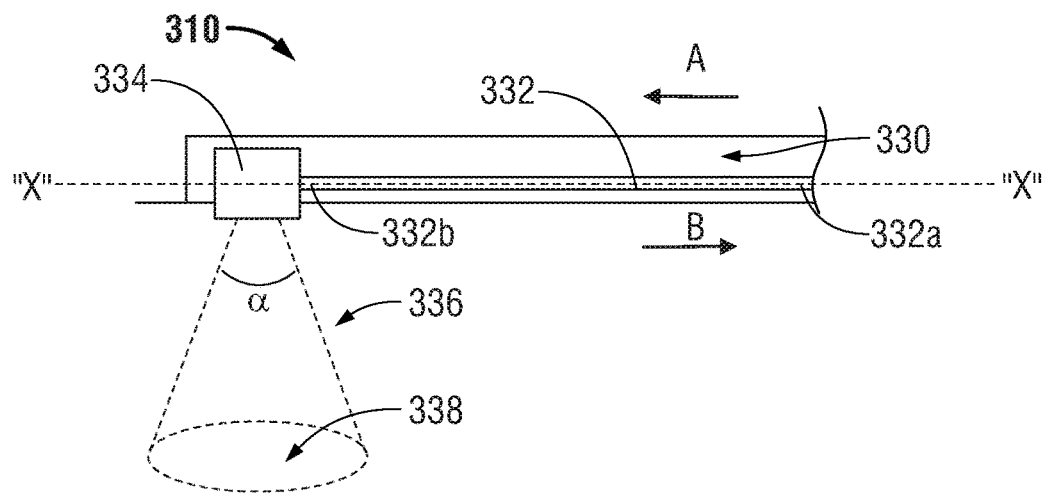
FIG. 4C is a side, schematic view of a laser fiber of the end-effector assembly of FIG. 4A.

FIGS. 4A through 4C illustrate an embodiment of an end-effector assembly 300 that includes jaw members 310 and 320 having proximal ends 310a, 320a, respectively, and distal ends 310b, 320b, respectively. Each jaw member 310 and 320 has a tissue-contacting surface 312 and 322, respectively. In some embodiments, the tissue-contacting surfaces 312 and 322 may include a transparent coating or cover disposed on the surface thereof, similar to the tissue-contacting surfaces 112 and 122 of FIGS. 2A and 2B. Additionally, jaw member 310 includes a channel or groove 330 defined therealong that is configured to include a surgical treatment laser fiber 332 (e.g., sealing, cutting and/or sensing) having proximal and distal ends 332a and 332b. Surgical treatment laser fiber 332 is configured to translate along a longitudinal axis "X-X", defined within jaw member 310, and within channel 330. For example, surgical treatment laser fiber 332 may be translated from proximal end 310a to distal end 310b of jaw member 310 (e.g., in a distal direction "A") to cut, seal and/or sense tissue being grasped between jaw members 310 and 320. Additionally or alternatively, surgical treatment laser fiber 332 may be translated from distal end 310b to proximal end 310a of jaw member 310 (e.g., in a proximal direction "B") to cut, seal and/or sense tissue being grasped therebetween. Surgical treatment laser fiber may be stationary within either one or both of the jaw members 310 and 320. In other embodiments, any other suitable type of light energy, including but not limited to laser light energy, may be transmitted by the aforementioned fibers (and/or other fiber pathways).

Referring to FIGS. 4A through 4C, the distal end of laser fiber 332b includes a laser emitter 334 that is configured to emit a laser beam into a defined solid angle 336 forming a desired illumination pattern. Laser fiber 332 may be a so-called "end-firing" or "side-firing" laser fiber. The term "end-firing" as used herein denotes a laser fiber that has the capability to emit a light along a longitudinal axis "X-X" defined by jaw member 310. The term "side-firing" as used herein denotes a laser fiber that has the capability to emit light (or any other suitable light energy) that is non-parallel to the longitudinal axis "X-X" of jaw member 310. Laser emitter 334 may include various components, such as one or more reflective surfaces (e.g., mirrors), one or more optical fibers, one or more lenses, or any other suitable components for emitting and/or dispersing a laser beam. More particularly, laser emitter 334 is configured to emit light into the solid angle 336 that has an outer boundary that may be variable or predetermined. By varying or adjusting the solid angle 336, a laser target area 338 may be adjusted to vary the intensity of the laser light energy illuminating the tissue and the area of the tissue being treated, dissected or cut. Laser target area 338 may define any suitable target shape, for example, but not limited to an ellipse, rectangle, square and triangle. In some embodiments, laser emitter 334 may also be configured to seal and/or cut tissue grasped between the jaw members.

In addition to longitudinal movement of the laser emitter 334 along the longitudinal axis "X-X," the laser emitter 334 may also be rotated about the axis "X-X" and/or moved laterally (e.g., transverse) with respect thereto. Longitudinal, lateral, and rotational motion of the laser emitter 334 allows for directing light energy in any desired direction to accomplish desired tissue treatment effects.

Reflective groove(s) 340 may be made from a polished metal or a coating may be applied to the jaw member 320 if the jaw member 320 is formed from a non-metal and/or non-reflective material (e.g., plastic). The reflective groove 340 reflects laser light back through the tissue. Laser emitter 334 may receive the reflected laser light and transmit the signal back to energy source 40 for processing. Various types of data may be integrated and calculated to render various outcomes or control tissue treatment based on the transmitted or reflected light.

Figure 5:
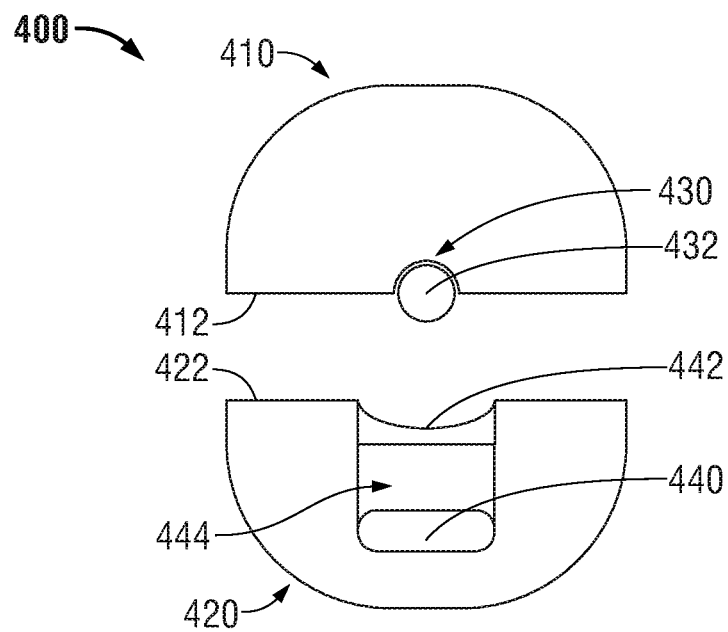
FIG. 5 is a front, cross-sectional view of an end-effector assembly in accordance with another embodiment of the present disclosure.

FIG. 5 illustrates an embodiment of an end-effector assembly 400 for forming a desired illumination pattern. End-effector assembly 400 includes jaw members 410 and 420 having tissue-contacting surfaces 412 and 422. Similar to the above-described jaw members, jaw members 410 and 420 cooperate to grasp tissue therebetween. Jaw member 410 defines a channel or groove 430 therealong that is configured to include a laser fiber 432 that spans along jaw member 410 and is configured to emit a laser light within and along the length of jaw member 410. In some embodiments, the fiber 432 may be substituted by any laser source such as a fiber laser (e.g., tunable thalium fiber laser) described in this disclosure. In further embodiments, the tissue-contacting surfaces 412 and 422 may include a transparent coating or cover disposed on the surface thereof, similar to the tissue-contacting surfaces 112 and 122 of FIGS. 2A and 2B.

Jaw member 420 includes a receiving fiber 440 disposed within a cavity 444 defined therein that is configured to receive the laser light emitted from laser fiber 432. In some embodiments, the fiber 440 may be substituted by any optical detectors described in this disclosure or other suitable optical detectors. An optical window 442 is disposed along the surface of jaw member 420 between laser fiber 432 and receiving fiber 440. Optical window 442 may be any suitable type of optical lens configured to direct the laser light being emitted from laser fiber 432 to receiving fiber 440. Cavity 444 may be configured to contain a gas or any other medium to facilitate reception of laser light emitted by laser fiber 432 by receiving fiber 440.

Optical properties of tissue are known to change during heating. Properties such as the absorption coefficient ($\mu_a$), scattering coefficient ($\mu_s$), and anisotropy coefficient (g) have been shown to change as a function of temperature and time. These properties affect the transmission and reflection of light as it interacts with tissue. The present disclosure incorporates a receiving fiber 440 that may be used to detect and/or monitor changes in the transmission of laser light from laser fiber 432 through the tissue during a sealing cycle to determine when a desired tissue effect has been achieved. In this configuration, cut completion, e.g., when the tissue is separated, may also be detected and/or monitored using the receiving fiber 440.

Figure 6:
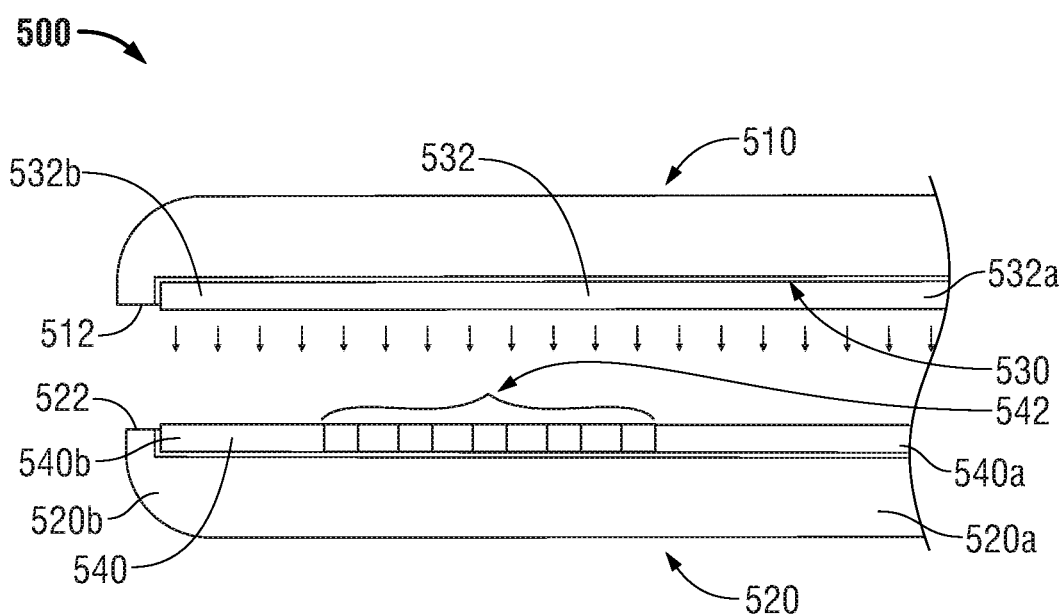
FIG. 6 is a side, cross-sectional view of an end-effector assembly in accordance with another embodiment of the present disclosure.

FIG. 6 illustrates an embodiment of an end-effector assembly (generally depicted as end-effector assembly 500) for forming a desired illumination pattern. End-effector assembly 500 includes jaw members 510 and 520 having tissue-contacting surfaces 512 and 522. Similar to the above-described jaw members, jaw members 510 and 520 cooperate to grasp tissue therebetween. Additionally, jaw member 510 defines a channel or groove 530 therealong that is configured to include a laser cutting fiber 532 that spans between proximal and distal ends 532a and 532b of jaw member 510. Laser fiber 532 is configured to emit a laser light within and along the length of jaw members 510 and 520. On an opposing side, a receiving fiber 540 is disposed within jaw members 520 and extends along a length thereof and is configured to receive the laser light emitted from laser fiber 532.

Receiving fiber 540 includes proximal and distal ends 540a and 540b and also includes one or more sensors 542 therebetween. Sensor(s) 542 is configured to monitor a temperature during a seal cycle and provide feedback as to when a seal cycle is complete. Since pressure is a factor in the quality of a seal following a sealing treatment, sensor 542 may also determine jaw pressure by measuring the strain in the jaw members 510 and 520 resulting from applied mechanical loads when tissue is grasped between jaw members 510, 520. In this configuration, feedback may be provided to an operator (and/or to the controller 42) as to whether the appropriate jaw pressure has been attained prior to energy activation to achieve a proper tissue seal.

Figure 7A:
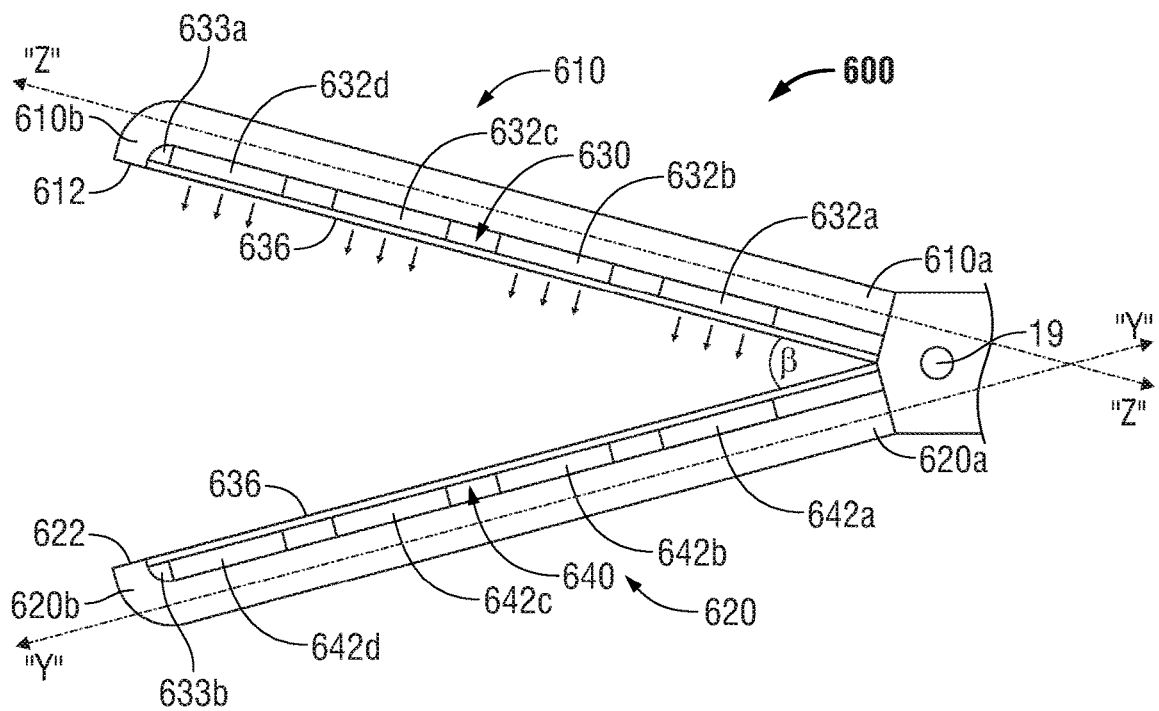
FIGS. 7A and 7B are side, cross-sectional views of an end-effector assembly in accordance with another embodiment of the present disclosure.
Figure 7B:
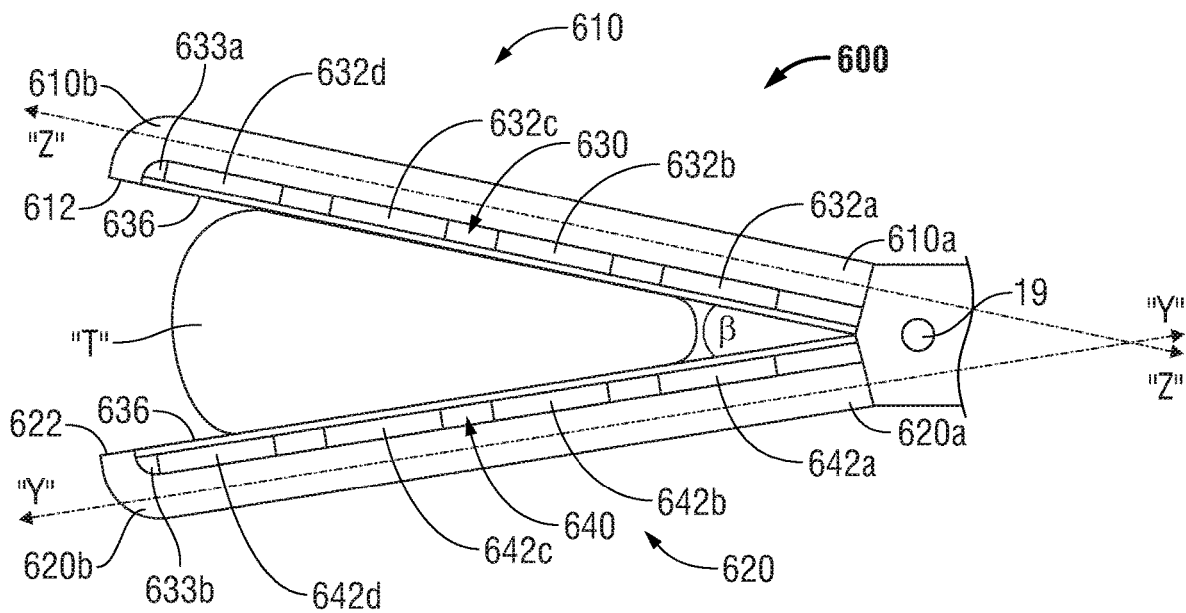

FIGS. 7A and 7B illustrate another embodiment of an end-effector assembly 600 for forming a desired illumination pattern. End-effector assembly 600 includes jaw members 610 and 620 having tissue-contacting surfaces 612 and 622. Similar to the above-described jaw members, jaw members 610 and 620 cooperate to grasp tissue therebetween. Jaw members 610 and 620 each define longitudinal axes "Z-Z" and "Y-Y," respectively, that span from their respective proximal ends 610a, 620b to their respective distal ends 610b, 620b. Longitudinal axes "Z-Z" and "Y-Y" define an angle "β" that increases as jaw members 610 and 620 are separated from each other, when pivoted from a closed configuration to an open configuration.

End-effector assembly 600 includes one or more light-emitting elements 632a, 632b, 632c, and 632d that are disposed within a channel 630 defined along the length of jaw member 610. Each light-emitting element 632a, 632b, 632c, and 632d is configured to emit a light energy within and along the length of jaw members 610 and 620. Light-emitting elements 632a, 632b, 632c, and 632d may be any suitable type of light-emitting element, for example, but not limited to high-intensity LEDs configured for medical use and/or tissue treatment, optical fibers or other optical elements configured to emit light into the tissue. Light-emitting elements 632a, 632b, 632c, and 632d may be selectively activatable (e.g., one or a few at a time) and may emit light at different wavelengths. One or more light-receiving elements 642a, 642b, 642c, and 642d are disposed within a channel 640 defined along the length of jaw member 620. Each light-receiving element 642a, 642b, 642c, and 642d is configured to detect the light energy emitted from the light-emitting elements 632a, 632b, 632c, and 632d. The light-emitting elements 632a, 632b, 632c, and 632d and the light-receiving elements 642a, 642b, 642c, and 642d may be disposed behind a protective substrate 636 configured to transmit light.

The light-receiving elements 642a, 642b, 642c, and 642d may be any suitable light-receiving element, such as a lens, an optical fiber, or photodetector, and may be configured to measure optical properties of the tissue. In some embodiments, the light-receiving elements may collect and transmit light to optical systems configured to provide a variety of spectroscopic measurements including Raman spectroscopy, which is suitable for determining seal competition and identification of specific tissue types and its constituents (e.g., collagen, protein, water, etc.). Raman spectroscopy is described in more detail later in this description.

In some embodiments the light-receiving element 642a, 642b, 642c, and 642d and the light-emitting elements 632a, 632b, 632c, and 632d may be interspersed between the jaw members 610 and 620, such that each of the jaw members 610 and 620 includes one or more receiving modules and one or more light-emitting elements. This configuration provides for measuring optical properties (e.g., reflection and transmission data) at each jaw member 610 and 620 and allows for use of optical coherence tomography to obtain images of the tissue grasped between the jaw members 610 and 620. Other techniques for determining optical tissue properties are disclosed in a commonly-owned U.S. patent application Ser. No. 12/665,081 entitled "Method and System for Monitoring Tissue During an Electrosurgical Procedure," the entire contents of which is incorporated by reference herein.

Each light-emitting element 632a, 632b, 632c, and 632d may be configured to independently adjust its emittance of light energy along the jaw member 610 depending on angle "β." For example, when angle "β" is about 45 degrees (e.g., when jaw members 610 and 620 are moved towards an open configuration) the distal-most light-emitting element 632d may emit light energy with a greater intensity than the proximal-most light-emitting element 632a. As angle "β" decreases to about 2 degrees (e.g., when jaw members 610 and 620 are moved towards a closed configuration) light-emitting elements 632a, 632b, 632c, 632d are configured to emit light energy with substantially the same intensity.

Intensity of the light energy, including individual intensity as described above, transmitted through the light-emitting elements 632a, 632b, 632c, and 632d may be adjusted by the controller 42 based on the measured angle "β" and/or the gap distance between the jaw members 610 and 620. As used herein, the term "gap distance" as used herein denotes the distance between the tissue-contacting surfaces 612 and 622. Since the jaw members 610 and 620 are pivotable relative to each other, the angle "β" therebetween is directly related to the gap distance and the two concepts are used interchangeably. Angle "13" may be measured using any suitable proximity sensors 633a, 633b disposed within the jaw members 610 and 620, respectively. The sensors 633a, 633b may be coupled to the controller 42 and include, but are not limited to, Hall Effect sensors, RF based sensors, and the like. In some embodiments, the sensors 633a, 633b may be a pair of corresponding light transmitter/receiver elements. In particular, a sensor may be a light-emitting element (e.g., LED) paired with a photodetector (e.g., PIN diode).

In some embodiments, the angle "β" may be controlled to achieve a desired gap distance between the jaw members 610 and 620 to match the thickness of the tissue to the optical depth of the light energy. If the thickness of the tissue is not greater than the optical depth of the light being passed through the tissue, then the light energy is not going to be fully absorbed. This occurs if the tissue is compressed such that it is thinner than the optical depth of the light energy being used. In addition, if the tissue is not sufficiently compressed, light energy does not fully penetrate the compressed tissue resulting in non-uniform heating of the tissue. Controlling of the gap distance to substantially match the optical depth of the light energy with the thickness of the tissue ensures that light energy is optimally absorbed.

In some embodiments where the jaw members 610 and 620 include reflective surfaces, such as the jaw members 110 and 120, the angle "β" may also be controlled while taking into consideration the reflection of the light from the tissue-contacting surfaces 612 and 622.

The controller 42 obtains the angle "β" from the sensors 633a, 633b and determines the gap distance based on the measurement. The controller 42 also obtains the wavelength of the light energy being delivered by the energy source 40. This may be accomplished by storing a value of the wavelength in memory or any other computer-readable storage device which may be either transient (e.g., random access memory) or non-transient (e.g., flash memory). The controller 42 then calculates the desired gap distance based on the stored wavelength value and stored tissue properties. The controller 42 also compares the actual gap distance and/or angle "β" to desired gap distance and/or angle "β" as calculated based on the wavelength. Based on the comparison, the controller 42 may adjust the gap distance and/or angle "β" between the jaw members 610 and 620 automatically and/or output the difference for the user. Automatic adjustment may be accomplished by providing the jaw members 610 and 620 with automatic closure mechanisms such as those disclosed in commonly owned U.S. Pat. No. 7,491,202, entitled "Electrosurgical Forceps With Slow Closure Sealing Plates and Method of Sealing Tissue," which discloses automatic gap control for electrosurgical forceps, the entire contents of which is incorporated by reference herein.

For manual gap adjustment, the controller 42 may output the difference between actual and desired gap distance and/or angle "β" in an audio/visual manner. In some embodiments, the actual and desired gap distance and/or angle "β" or the difference therebetween may be represented numerically and/or graphically (e.g., color-coded). The difference may also be represented by audio alarms (e.g., adjusting frequency or amplitude of sound pulses).

As discussed in the previous embodiments, light-emitting elements 632a, 632b, 632c, and 632d and receiving modules 642a, 642b, 642c, and 642d may be configured to have optical sensing properties such that each pair of light-emitting element and receiving module (e.g., light-emitting element 632a and receiving module 642a) may be used to monitor the sealing process at a particular position. Light-emitting elements 632a, 632b, 632c, and 632d and receiving modules 642a, 642b, 642c, and 642d may also be configured to monitor the presence and state of other material in and around the sealing device and may also modify a sealing algorithm based upon the information collected.

In other embodiments, light-emitting elements 632a, 632b, 632c, and 632d and receiving modules 642a, 642b, 642c, and 642d may also be configured to inject a heat pulse and measure the response of tissue "T", measure spectral characteristics in transmission and/or reflection, measure spectral characteristics at different positions, measure spectral characteristics at different light frequencies. Light-emitting elements 632a, 632b, 632c, and 632d and receiving modules 642a, 642b, 642c, and 642d may also be configured to measure temperature at one or more locations between proximal and distal ends of jaw members 610 and 620.

Figure 8A:
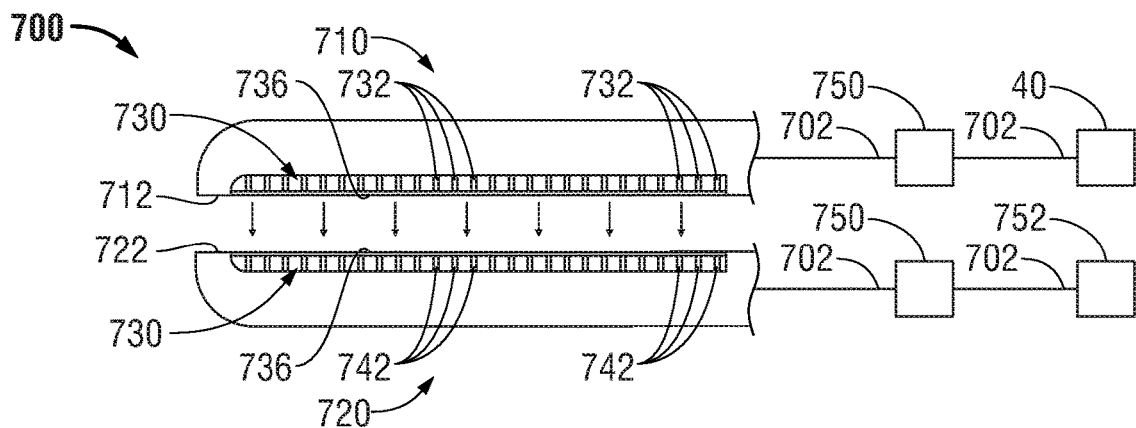
FIG. 8A is a side, cross-sectional view of an end-effector assembly according to another embodiment of the present disclosure.
Figure 8B:
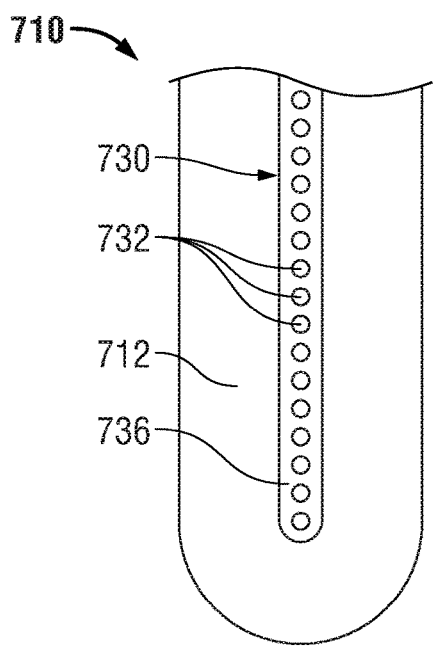
FIGS. 8B and 8C are top views of the end-effector assembly shown in FIG. 8A.
Figure 8C:
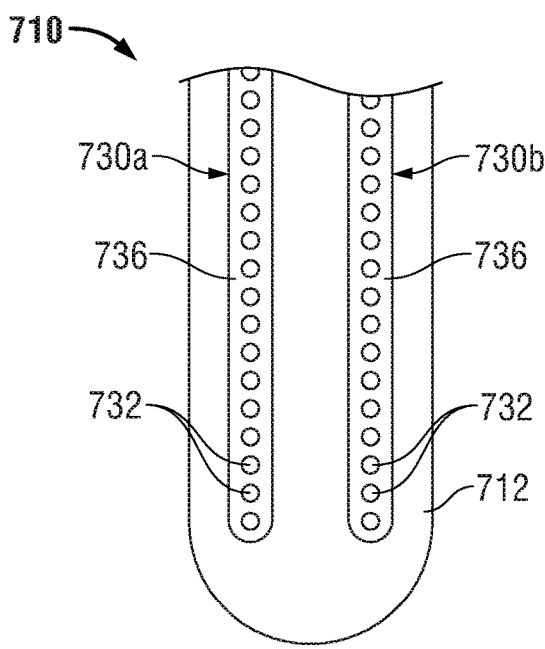

In FIGS. 8A through 8C, an embodiment of an end-effector assembly 700 is shown for forming a desired illumination pattern. End-effector assembly 700 includes jaw members 710 and 720 having tissue-contacting surfaces 712 and 722. Similar to the above-described jaw members, jaw members 710 and 720 cooperate to grasp tissue therebetween. Jaw members 710, 720 are operably connected to energy source 40 via an optical fiber 702 that provides light energy for treating tissue grasped between jaw members 710, 720. The optical fiber 702 may have any suitable shape, for example, but not limited to, rectangular, oval, and polygonal. In addition, distal end 1032a may also take the form of various suitable configurations (e.g., sharp or blunt).

Each jaw member 710, 720 includes one or more channels 730 having one or more vertically-aligned optical fibers 732 that are configured to emit and receive light energy from energy source 40 via optical fiber 702. In some embodiments, optical fibers 732 of jaw member 710 are vertically-aligned with optical fibers 742 of jaw member 720 such that optical communication is established. That is, one of the optical fibers is a transmitting optical fiber (e.g., optical fiber 732) and the opposing fiber is a receiving optical fiber (e.g., optical fiber 742). Any number of transmitting optical fibers 732 may be disposed about jaw member 710. Additionally or alternatively, any number of transmitting optical fibers 742 may be disposed about jaw member 720. Thus, in other embodiments, vertical alignment of optical fibers 732 and 742 is not particularly necessary.

In some embodiments, end-effector assembly 700 may also include one or more optical switches 750 that provide selective activation and detection of light energy to and from jaw members 710 and 720 by an operator and/or energy source 40. Detection of light energy may be provided by an optical detector 752 or the like. In some embodiments, each channel 730 may be covered by a transparent cover 736 to allow optical communication between jaw members 710 and 720. It should be noted that any type of detecting device may be utilized with any of the embodiments presently disclose, for example, but not limited to photo diodes and charged coupled device (CCD) arrays.

FIG. 8B illustrates jaw member 710 having a single channel 730 defined therethrough that includes a plurality of optical fibers 732, as described above, that are covered by cover 736. Cover 736 may be any suitable material configured to allow optical communication between optical fibers 732 and 742. In another embodiment, FIG. 8C illustrates jaw member 710 defining a plurality of channels 730a and 730b therethrough and also includes a plurality of optical fibers 732 that are covered by cover 736.

As shown in FIGS. 9A and 9B, in further embodiments, a light dissection element 2445 may be disposed on an outer periphery of one of the jaw members 2110 and 2120. For sake of simplicity only a single jaw member, namely, the jaw member 2110 is discussed herein.

The dissection member 2445 may be a light-diffusing element, such as the light diffuser 132 described above with respect to FIGS. 2A and 2B. The dissection member 2445 is coupled via an optical fiber 2446 to the generator 40 and is disposed on or along at least a portion of an outer periphery 2110a of the jaw member 2110. As it is used herein, the term "outer periphery" denotes any surface of the jaw member 2110, such as the jaw housing 2116, that is not a tissue sealing contact surface 2112 or 2122. The dissection member 2445 may be selectively activated via the switch 2200 similar to the dissection member 2145 and may incorporate similar features, e.g., preventing light energy from being transmitted to the sealing surfaces 2112 and 2122 as described above with respect to the dissection member 2145.

Referring now to FIG. 10, an embodiment of an end-effector assembly 1900 for forming a desired illumination pattern. End-effector assembly 1900 includes jaw members 1910 and 1920 having tissue-contacting surfaces 1912 and 1922. Similar to the above-described jaw members, jaw members 1910 and 1920 cooperate to grasp tissue therebetween. Jaw members 1910, 1920 are operably connected via an optical fiber 1911 to a light energy source (e.g., generator 40). In particular, the optical fiber 1911 is coupled to the jaw member 1910. The light may be provided in different forms, including, but not limited to lasers, light-emitting diode, and any other suitable type of light energy.

The jaw member 1910 is formed from an optically transmissive material having an outer reflective coating 1910a. The transmissive material may be an optically diffusing material, such as, frosted sapphire crystal or an optically scattering material, such as polyoxymethylene, which is sold under a trademark DELRIN®, available from DuPont, Wilmington, Del. The light from the optical fiber 1911 is transmitted to the jaw member 1910 and is contained therein by the reflective coating 1910a. This prevents the light from escaping outside the jaw member 1910 other than through the tissue-contacting surface 1912.

The jaw member 1920 may be formed from any optically absorbent or reflective tissue material. In some embodiments, the jaw member 1920 may include an optically absorbent or reflective coating 1920a on the tissue-contacting surface 1922. The coating 1920a and/or the jaw member 1920 block the light from passing through the jaw member 1920 concentrating the light energy at the tissue grasped between the jaw members 1910 and 1920.

Light energy is suitable for sealing tissue since it is converted into heat energy by absorption at a molecular level. In particular, certain molecules absorb light at certain wavelengths. In addition, as tissue is treated it undergoes physical and chemical changes, thus the wavelength at which light is optimally absorbed also changes. In some embodiments, light energy may be provided at two or more wavelengths to provide light energy that is optimally absorbed by two or more molecules (e.g., tissue types).

Figure 11:
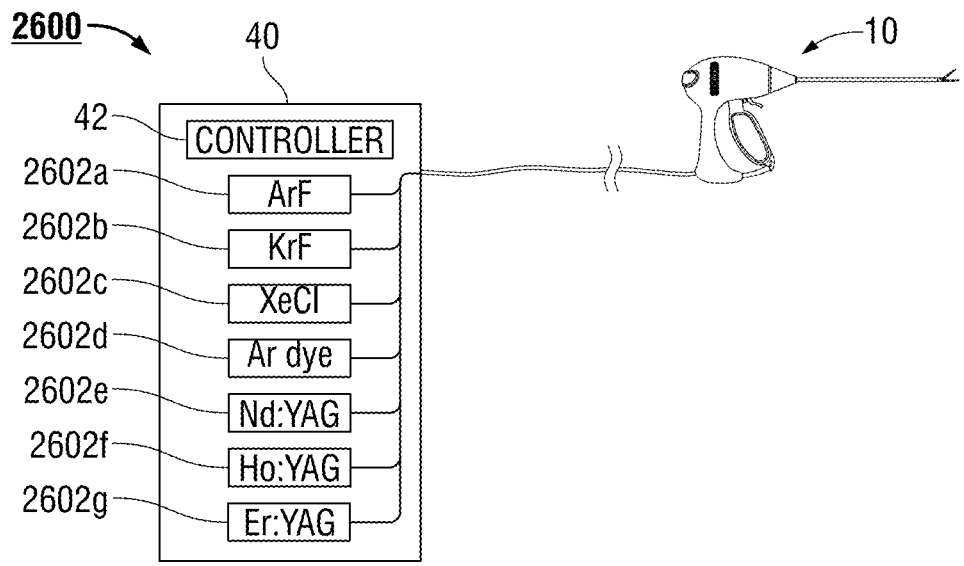
FIG. 11 is a schematic diagram of a surgical system in accordance with an embodiment of the present disclosure.

FIG. 11 shows a light energy surgical system 2600 including the energy source 40 and the forceps 10. The forceps 10 may include any of the embodiments of the jaw members described above. The generator 40 in combination with the forceps 10 may be utilized to generate light having a desired wavelength. The generator 40 may produce light energy at single or multiple wavelengths and may include a plurality of laser sources described above that are capable of producing light at multiple wavelengths. The generator 40 includes a plurality of laser light sources to generate laser light having a wavelength from about 100 nm to about 10,000 nm, which covers the majority of the tissue constituents. In particular, the generator 40 includes an ArF excimer laser 2602a, a KrF excimer laser 2602b, a XeCl excimer laser 2602c, an argon-dye laser 2602d, an Nd:YAG laser 2602e, an Ho:YAG laser 2602f, an Er:YAG laser 2602g.

Figure 12:
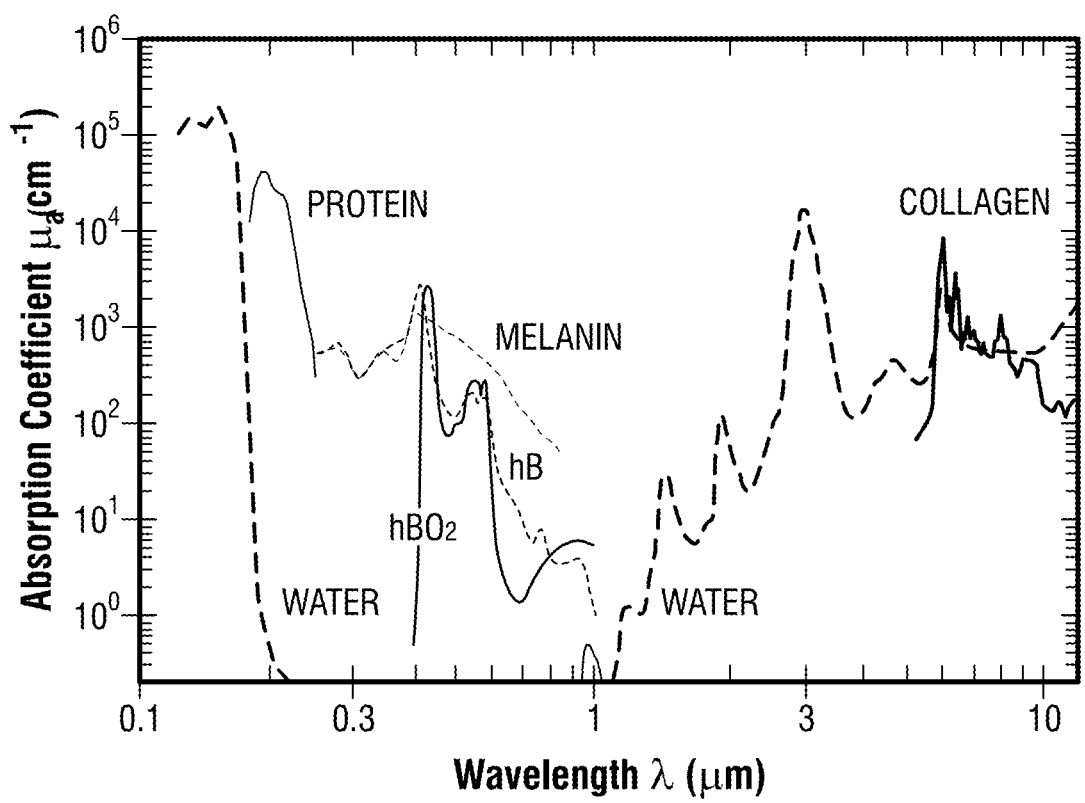
FIG. 12 is a plot of absorption coefficient versus wavelength of tissue constituents in accordance with an embodiment of the present disclosure.
Figure 13:
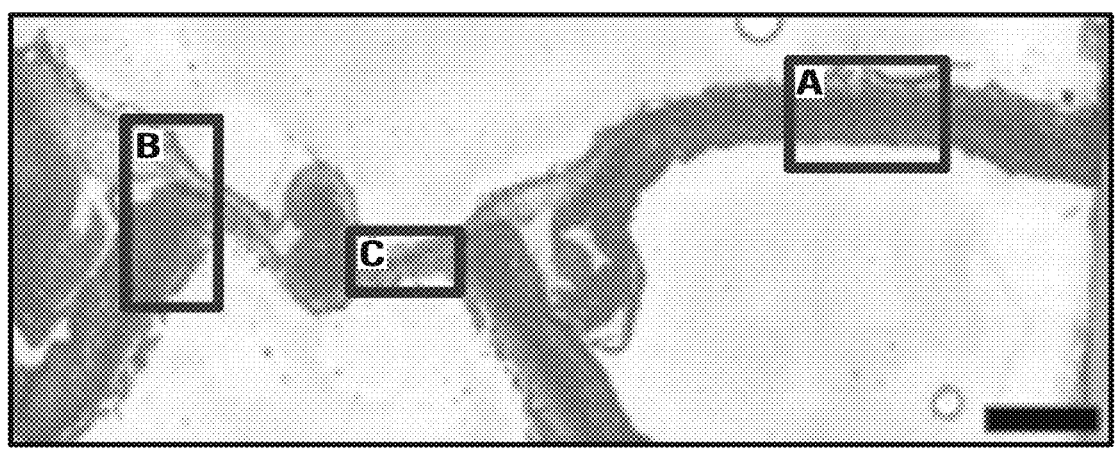
FIG. 13 is an illustrative representation of porcine blood vessel tissue in accordance with an embodiment of the present disclosure.

The forceps 10 may be used to determine condition and composition of tissue, as described in further detail above with respect to FIGS. 7A and 7B. FIG. 12 shows a graph illustrating absorption of various tissue constituents as a function of the wavelength ranging from ultraviolet (UV) spectrum to infrared (IR) spectrum. Tissue constituents that are encountered in tissue include, but are not limited to water, vasculature, epidermis and other skin layers, whole blood, melanosome, collagen, and the like.

During operation, the forceps 10 is used to analyze tissue, including measuring the absorption thereof. The absorption measurements are analyzed by the controller 42 of the generator 40 which then determines which of the one or more laser light sources 2602a-2602g to activate to obtain optimal absorption of the light energy. The controller 42 may be coupled to a multiplexer (not shown) and/or another optical output switching apparatus to control activation of the laser light sources 2602a-2602g.

The forceps 10 may sense optical tissue properties continuously during the sealing procedure and to vary light energy output including intensity and which of the laser light sources 2602a-2602g are activated. Once it is determined that the sealing procedure is complete, the controller 42 may activate specific laser light sources 2602a-2602g most suitable for cutting sealed tissue.

Raman-Spectroscopy Method for Analyzing Tissue Fusion Samples In Vitro

Past studies on possible mechanisms for heat-induced tissue fusion, particularly for blood vessel sealing, have utilized mainly either direct microscopic observation or mechanical strength testing. Changes within collagen bonds within the fused tissue are thought to be pivotal to the strength of the resulting fusion. It is widely accepted that heat denatures collagen to a gel-like amalgam, which then forms bonds between separated tissues. However, the actual changes that the collagen within the fused tissue undergoes during heat-induced RF tissue fusion and the mechanism for the formation of the resulting seal have remained unclear.

The method described herein demonstrated, for the first time, the use of Raman spectroscopy to characterize fused tissues in RF heat-induced tissue fusion. It was discovered that tissue restructuring, or more specifically tissue layer and collagen molecular restructuring in the fusion areas, is a contributing mechanism for a strong tissue fusion. Moreover, it was determined that a decrease in non-reducible collagen crosslinks and an increase in reducible collagen crosslinks occur during tissue fusion. These changes are associated with collagen undergoing heat treatment and this restructuring provides new insight into the effects of RF fusion on the biochemical changes in the native collagen. Additionally, the presence of compression pressure during fusion produced a difference in collagen restructuring. Tissues fused with compression showed an increase in collagen transformation while tissues fused without compression showed collagen changes associated with a heat treatment. Overall these insights are the first to demonstrate the previously suspected involvement of collagen in RF tissue fusion, both with and without concurrent compression, using Raman spectroscopy. These molecular insights help provide information on the transformation occurring due to RF tissue fusion as well as provide a basis for optical feedback methods.

Raman spectroscopy provides an attractive way of rapidly capturing the molecular environment of tissues without destroying or altering the samples. Raman micro-spectroscopy generates information-rich spectra that, when combined with chemometrics, provide powerful insight into the molecular diversity within heterogeneous biological samples. Proteins have been studied using Raman spectroscopy, wherein information regarding the amino acids (e.g., amide bonds between amino acids and their tertiary structure) can be extracted and analysed. Raman spectroscopy has been used to identify changes within isolated animal collagen during thermal and chemical denaturing. The method described herein provides a molecular fingerprint to identify collagen and demonstrate the powerful ability of Raman spectroscopy to expose specific molecular changes within collagen. Additionally, it is possible to deconstruct individual contributors, such as collagen, from an overall tissue sample for characterization and comparison. By scanning across an area of interest, individual Raman spectrum at each acquisition point can be combined to form a Raman map, which is similar to a microscopic image but with the ability to focus on certain chemical markers within the imaged area. The Raman map provides a direct observation of molecular distributions, such as that of collagen fibers, within a sampled area.

The method described herein demonstrates the use of Raman spectroscopy to characterize the RF tissue fusion in vitro. Tissue fusion was performed with two tissue types, namely, porcine blood vessels and small intestines, and the seal quality was accessed based on the mechanical strength of the seal given by burst pressure testing, as described later in this description. The Raman spectra was then acquired for fusion samples characterized as "strong seal" and "weak seal," and Raman mapping was conducted across fusion regions. Raman results were correlated to the mechanical strength of the seals, and the difference on the molecular level was investigated. The Raman maps were compared with conventional histopathology microscopic results, and the comparison results demonstrated the superiority in characterizing RF tissue fusion and the rich molecular information contained in fused tissue Raman spectra.

Materials and Methods of the Raman-Spectroscopy Method

Animal Tissue Preparation

Fresh porcine small bowels were obtained from a local abattoir, cut into 20-30 cm long segments, moistened with physiological saline and refrigerated at 4° C. for up to 30 hours (from the time of slaughter) until needed for tissue fusion experiments. Prior to the tissue fusion experiment, a segment of long samples was selected and immediately dissected into 5 cm long pieces for tissue fusion experiment. Prepared 5 cm samples were kept hydrated in sealed plastic sample bags with saline and used within thirty minutes. Porcine blood vessels were cleaned, cut into 6 cm long pieces, and then frozen within four hours after the animal was slaughtered. The frozen tissues were kept at −70° C. Frozen blood vessel samples were only thawed at room temperature immediately before the tissue fusion experiment.

RF Tissue Fusion

RF energy is used as the source for tissue heating. The RF generator was an energy research tool prototype developed by Covidien, Boulder, Colo., capable of delivering a programmable sinusoidal current from 0-7 A and a power from 0-350 W. An operating RF frequency of 472 kHz was chosen to avoid neuromuscular stimulation and electrocution. Two tissue sealing devices were used in the tissue fusion experiment: a commercially available LigaSure Impact™ instrument (Covidien, Boulder, Colo.) for blood vessel sealing and an anastomosis prototype for small bowel sealing. RF energy control algorithms were loaded to the fusion software written in LabVIEW (short for Laboratory Virtual Instrument Engineering Workbench) (National Instruments Corporation, Austin, Tex.) so that the entire procedure was automated. The algorithm was written to control RF energy delivery to ensure a continuous heating and a predetermined impedance varying profile.

During this tissue fusion experiment, tissue samples were clamped between the jaws of the fusion device. RF energy was supplied by the RF generator and applied to the tissue samples via electrodes in the jaws. The RF generator also continuously monitored both voltage and current delivered to the tissue. The varying tissue impedance was then obtained by using real-time voltage and current readouts. A compression spring in the handle of the LigaSure Impact™ device provided a constant pressure of ~0.3 megapascals (MPa). An air compressor connected to the energy research tool prototype supplied a variable compression pressure from 0 to 0.5 MPa. Over two-hundred tissue fusions were performed in this tissue fusion experiment.

Temperature Measurement

Tissue temperature was measured using a fine (0.005 inch) tip Teflon-insulated J-type thermocouple (5TC-TT-J-36-36, Omega Engineering, Bridgeport, N.J.). The thermocouple was inserted through slits made on the sealing device jaws and glued in place at the top of the slit so that its tip emerged 0.25 mm above the electrode surface. In this way the thermocouple can be placed in contact with the tissue surface without piercing it, and is insulated from the electrode. The communication between the thermocouple and the computer is achieved through a National Instruments (NI) PXI-6289 data acquisition (DAQ) board and an NI SCC-68 terminal block. The latter hosts four NI SCC-TC02 Thermocouple Signal Conditioning Modules. Each SCC-TC02 can drive one thermocouple and has individual signal conditioning modules with a 2 Hz low-pass filter, which filters out the RF signal and eliminates the RF interference from the thermocouple readout.

Sample Preparation and Imaging

Tissue samples were stored at −80° C., following tissue fusion. Thawed samples were trimmed and embedded in optimal cutting temperature medium (OCT, Tissue-Tek) by flash freezing in isopentane at −160° C. The OCT blocks were sectioned on a cryostat at −20° C., cutting 15 μm sections for histology and Raman spectroscopy. Sections for histology were mounted on glass, washed with water to remove the OCT, and stained with haematoxylin and eosin (H&E). Sections for Raman analysis were mounted on $MgF_2$ slides, stored at 4° C., and imaged without further processing. Visualisation of the H&E-stained sections was performed under 4× magnification on an Olympus IX51 inverted light microscope, captured digitally and spliced together to allow visualisation of the entire field.

Raman Microscopy

Tissue Raman maps were collected with a 785 nm laser, using a Renishaw InVia spectrometer (Renishaw plc, Gloucestershire, United Kingdom) connected to a Leica microscope (Leica, Wetzlar, Germany) as previously described. Raman maps were collected over selected regions of interest with a step size of 75 μm in the x and y direction. At each point a spectrum was collected using 5 accumulations of 5 second scans covering the Raman shifts range of 620-1700 $cm^{-1}$. Samples were tested for no longer than one hour at room temperature and kept hydrated using saline.

Raman spectra were pre-processed for background removal (baseline subtraction using weighted least squares) and multiplicative scattering correction. N-FINDR spectral unmixing algorithm was used to determine end-members (pure contributing components of each tissue) and every pixel of the resulting Raman map is represented as a linear combination of the end-members as previously described and results in an abundance value between 0 and 1 for all measured points.

Burst Pressure Measurement

The mechanical strength of the fused tissue was evaluated by a burst pressure (BP) testing system that included a syringe pump, a pressure gauge, a sample injection needle and a surgical clamp to close the small bowel tissue. The main arm of a Y-splitter tubing system was connected to a water-filled syringe controlled by the syringe pump. The other two split arms were connected to the pressure gauge and the sample injection needle, respectively. The surgical clamp sealed the other end of the piece of fused small bowel. The small bowel tissue was pierced by the sample injection needle to allow water to be infused into the sealed bowel without damaging the seal. High-pressure water inside the fused tissue caused seal burst at the fusion line. After the initiation of the BP test, the syringe pump drove the water filled syringe at a rate of 20 mL/min, which equally increased the pressure in the tubing system as well as in the fused tissue. When any burst or leak in the fused tissue pocket happened, the pressure gauge spotted a drop in water pressure and the peak pressure was recorded as the BP.

Results of the Raman-Spectroscopy Analysis

Burst Pressure Test Results

Approximately two-hundred porcine small bowel segments were fused for BP testing. The BP, as an indication of the fusion mechanical strength, varied significantly with the change of compression pressure during fusion. Tissue samples fused at compression pressures lower than 0.10 MPa displayed an average BP of ~10 mmHg, while samples fused at higher compression pressures (>0.10 MPa) showed an average BP of more than 20 mmHg. Increased burst pressures were observed at all compression pressure values above 0.10 MPa. The BP results serve as a guideline for the Raman experiments carried out in this study. Samples fused at three compression pressures, at 0, 0.2 and 0.3 MPa, were selected and analysed by Raman spectroscopy in order to understand the resulting differences in fusion strength.

For blood vessel samples, the LigaSure Impact™ instrument was employed, and the compression pressure was therefore at a fixed value of 0.3 MPa, which was provided by the integrated load spring in the device. The average BP for the blood vessels is above 100 mmHg. The BP difference between the blood vessel samples and small bowel samples was mainly due to tissue differences and the different devices used to perform the tissue fusions.

Raman Results

Figure 14A:
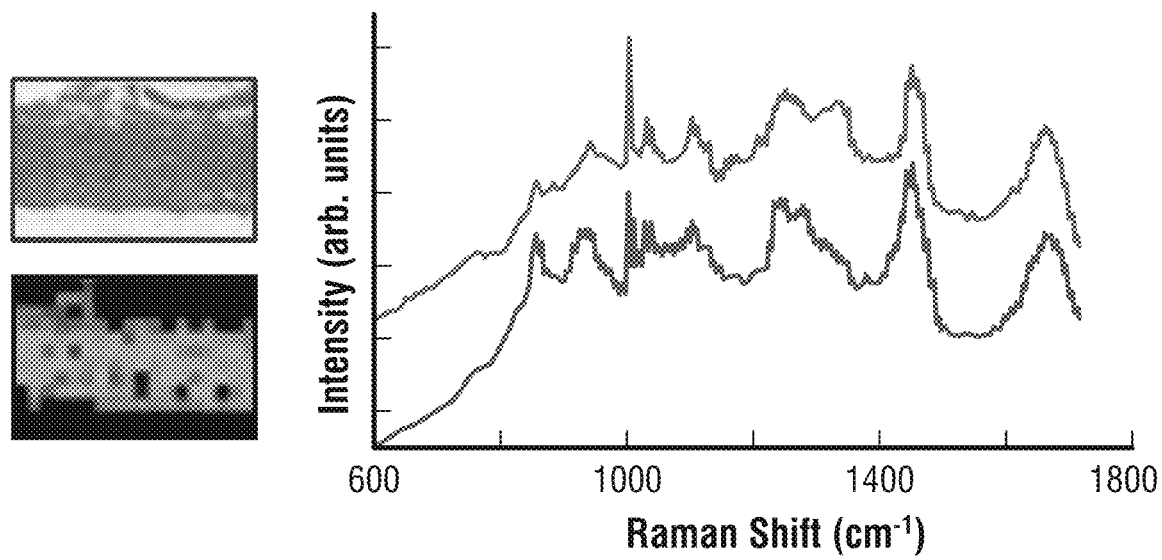
FIGS. 14A through 14C are Raman maps of the indicated regions shown in FIG. 13 according to an embodiment of the present disclosure.
Figure 14B:
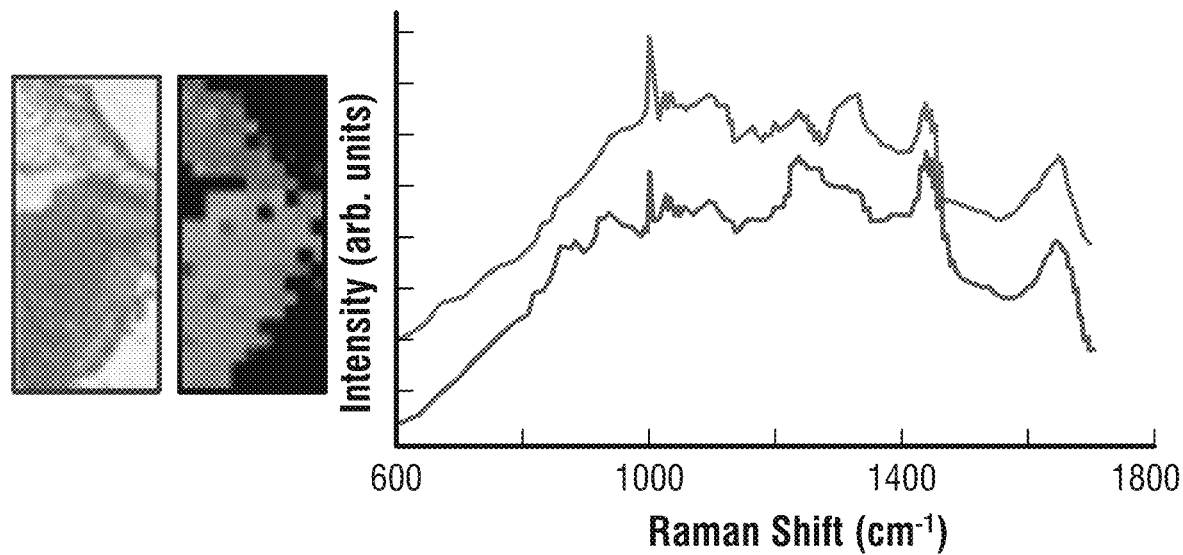
Figure 14C:
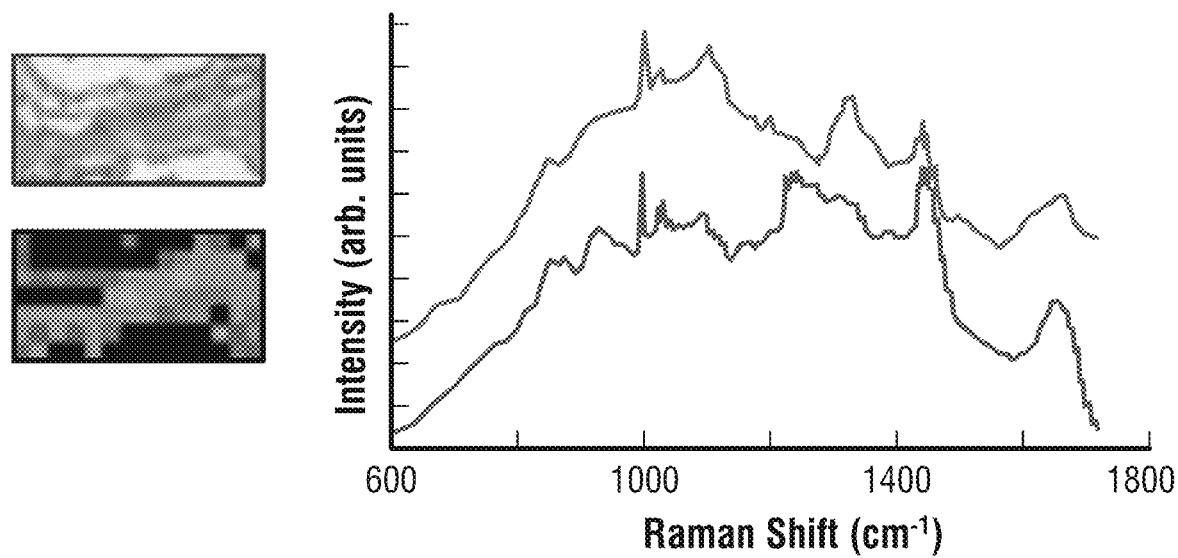

In FIGS. 14A, 14B and 14C, Raman maps collected over porcine blood vessel tissue selection are shown. Mapped regions included [A] healthy tissue, [B] interface between fused and healthy and [C] fused tissue. White light images of each selected area for Raman mapping are shown in sections [A-C] (scale=250 μm) with their corresponding Raman map shown in the red, green and black images. The spectra included in [A-C] shows the collagen end-member spectrum in red with the intensity of the red coloring in the Raman maps corresponding to the presence of collagen within that pixel. The non-collagen rich tissue end-member spectrum is shown in green and the intensity of the color green in the Raman map corresponds to the presence of non-collagen rich tissue within that pixel.

In FIGS. 15 through 20C, Raman maps collected over porcine bowel tissue selections are shown with no compression (FIGS. 15, 16A and 16C), compression at 0.2 MPa (FIGS. 17, 18A, 18B and 18C), and compression at 0.3 MPa (FIGS. 19, 20A, 20B and 20C). Mapped regions include [A] healthy, [B] interface between fused and healthy, and [C] fused tissue. White light images of each selected area for Raman mapping are shown in sections [A-C] (scale=250 µm) with their corresponding Raman map shown in the red, green and black images. The spectra include in [A-C] shows the collagen end-member spectrum in red with the intensity of the red coloring in the Raman maps corresponding to the presence of collagen within that pixel. The non-collagen rich tissue end-member spectrum is shown in green and the intensity of the color green in the Raman map corresponds to the presence of non-collagen rich tissue within that pixel.

Figure 15:
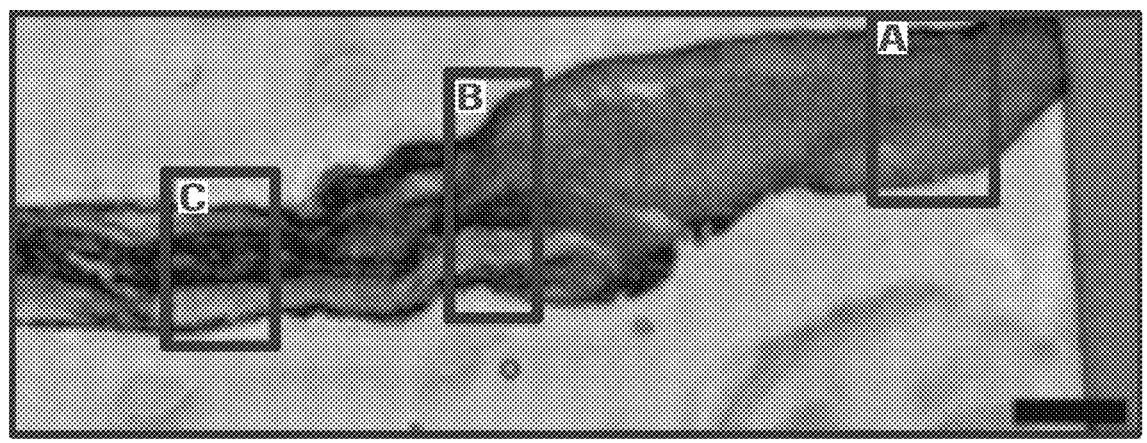
FIG. 15 is an illustrative representation of porcine bowel tissue in accordance with an embodiment of the present disclosure.
Figure 16A:
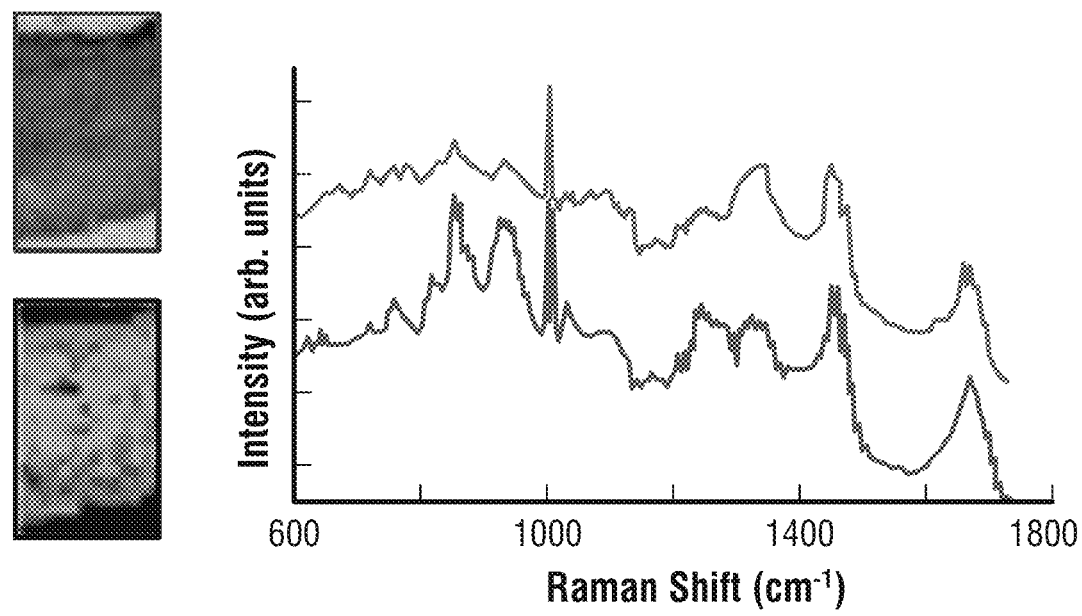
FIGS. 16A through 16C are Raman maps of the indicated regions shown in FIG. 15 in accordance with an embodiment of the present disclosure.
Figure 16B:
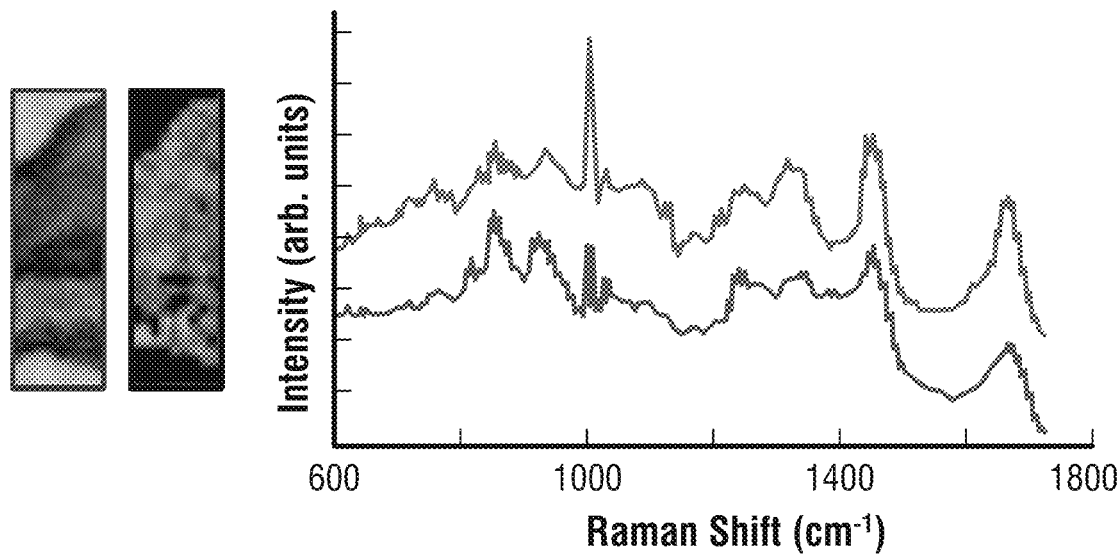
Figure 16C:
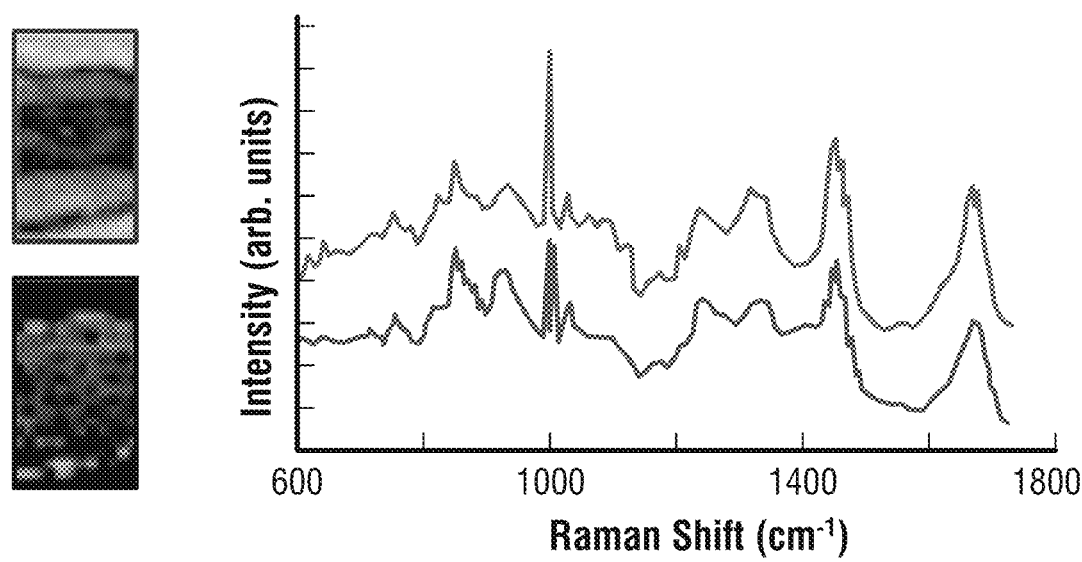
Figure 17:
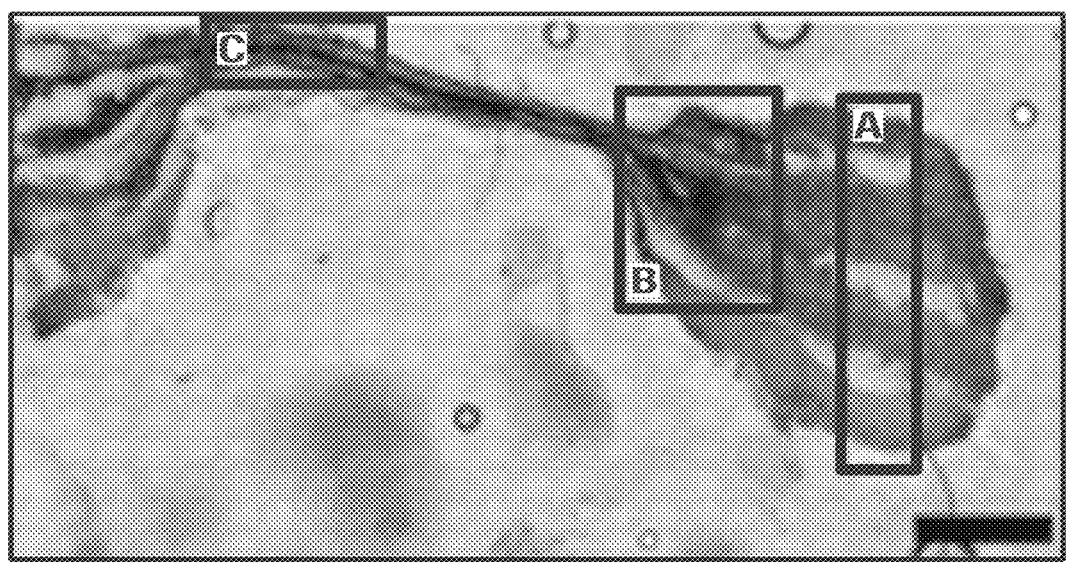
FIG. 17 is an illustrative representation of porcine bowel tissue in accordance with an embodiment of the present disclosure.
Figure 18A:
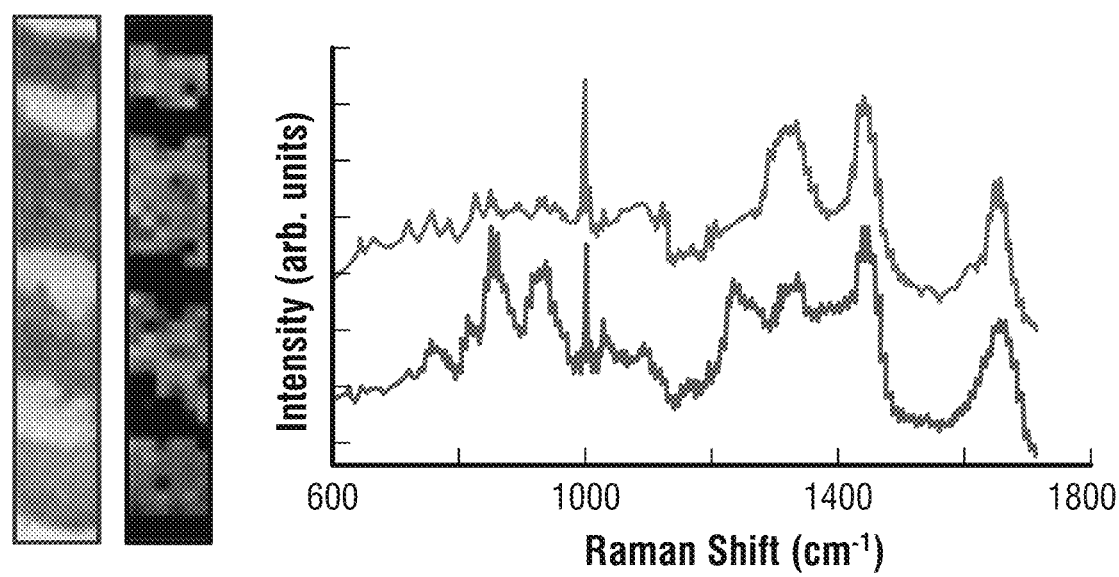
FIGS. 18A through 18C are Raman maps of the indicated regions shown in FIG. 17 in accordance with an embodiment of the present disclosure.
Figure 18B:
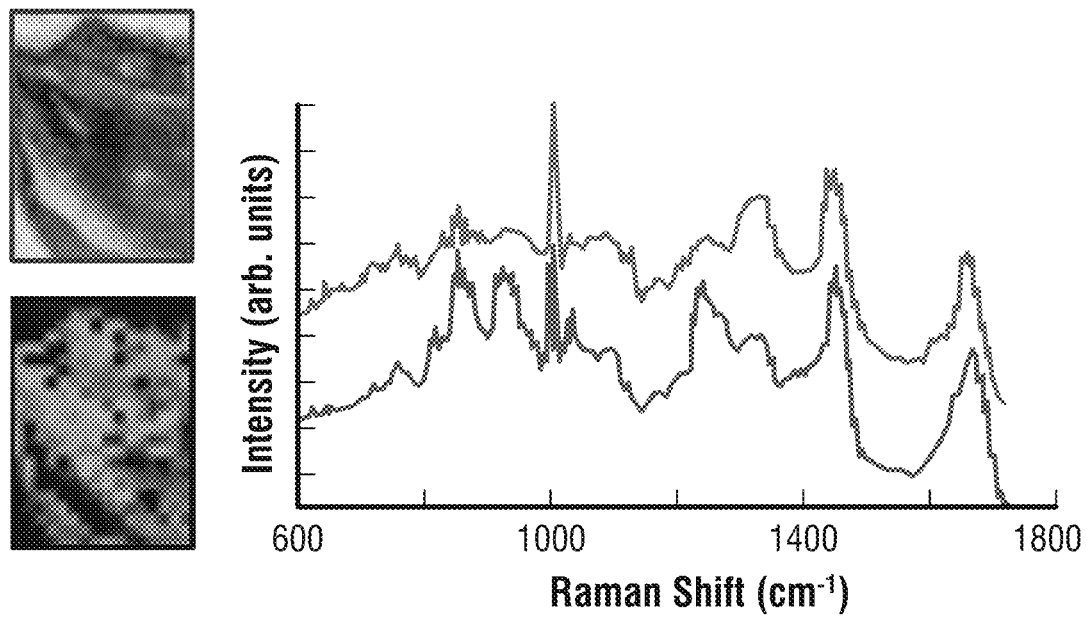
Figure 18C:
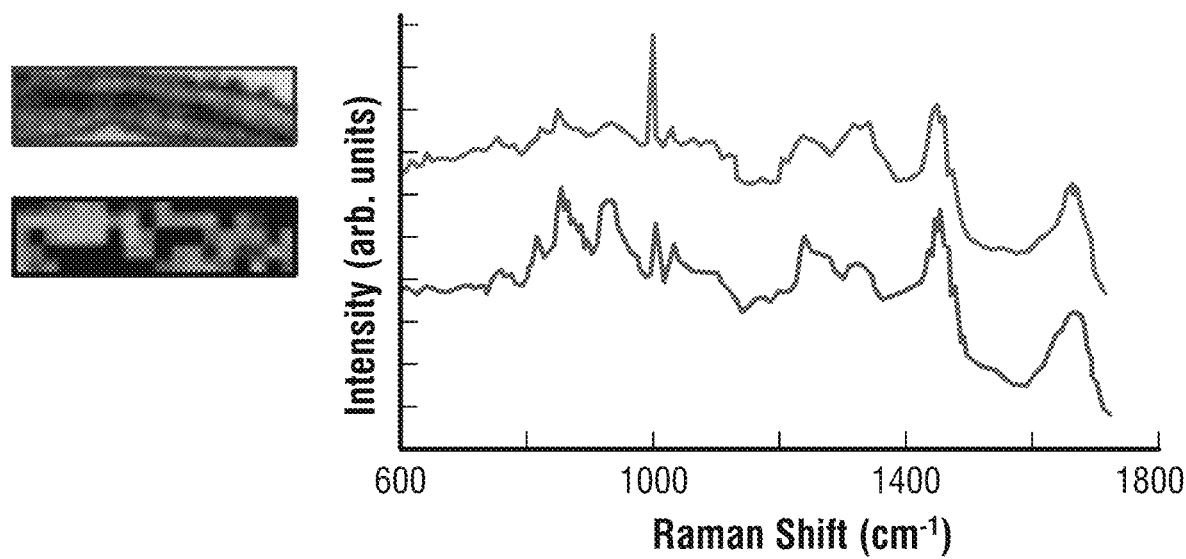
Figure 19:
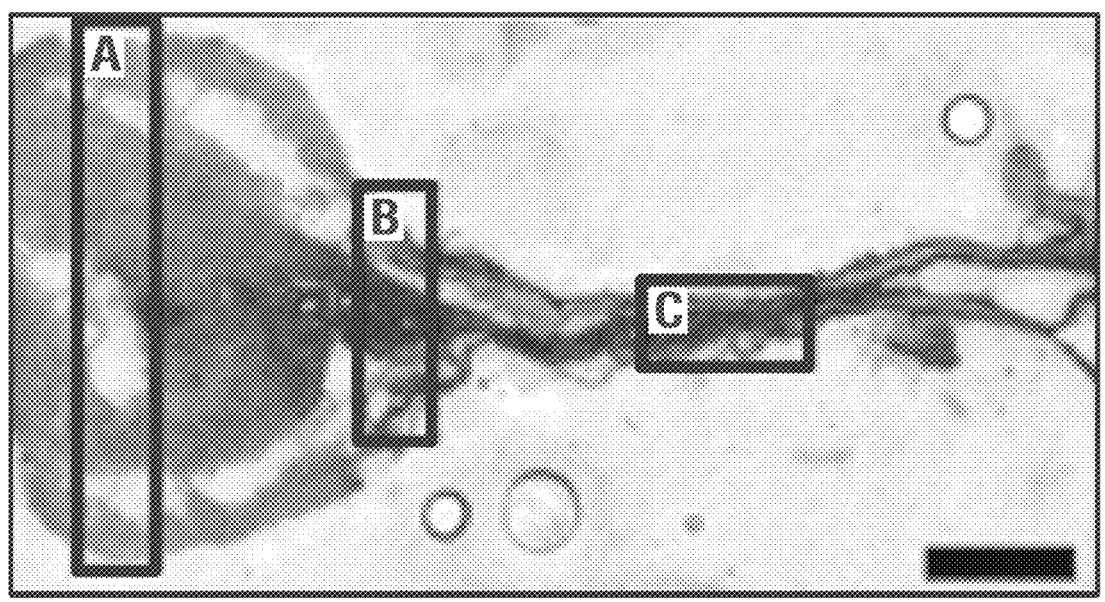
FIG. 19 is an illustrative representation of porcine bowel tissue in accordance with an embodiment of the present disclosure.
Figure 20A:
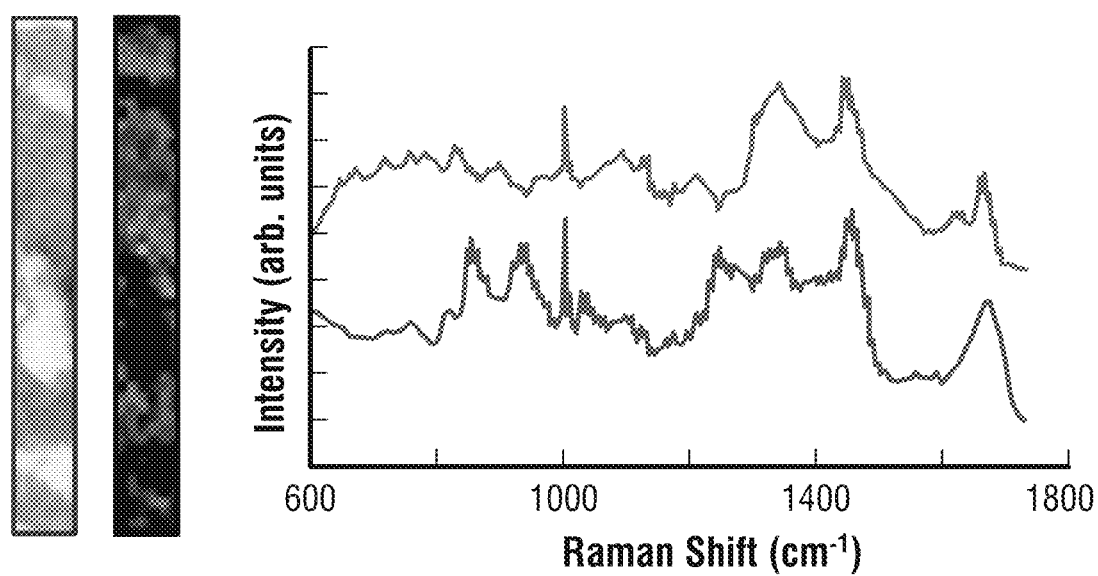
FIGS. 20A through 20C are Raman maps of the indicated regions shown in FIG. 19 in accordance with an embodiment of the present disclosure.
Figure 20B:
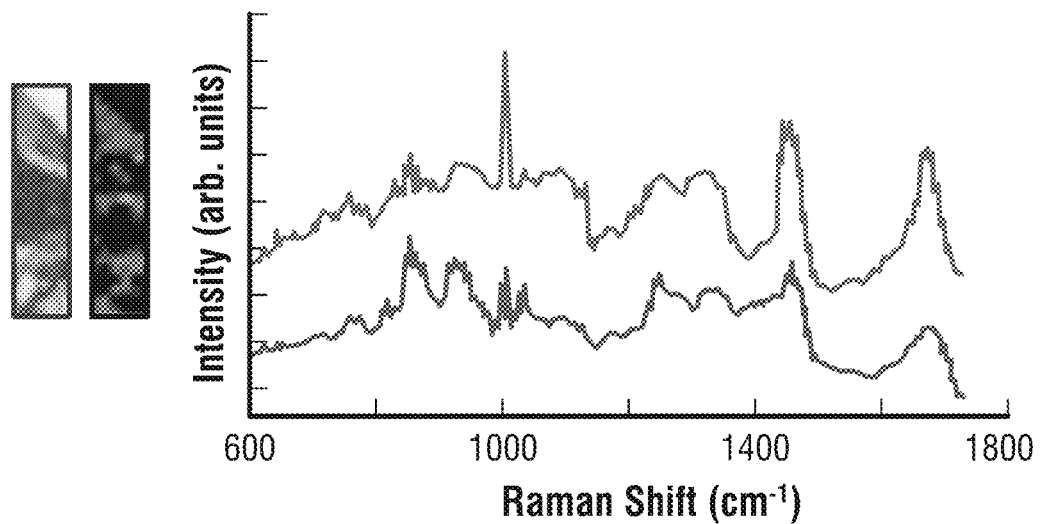
Figure 20C:
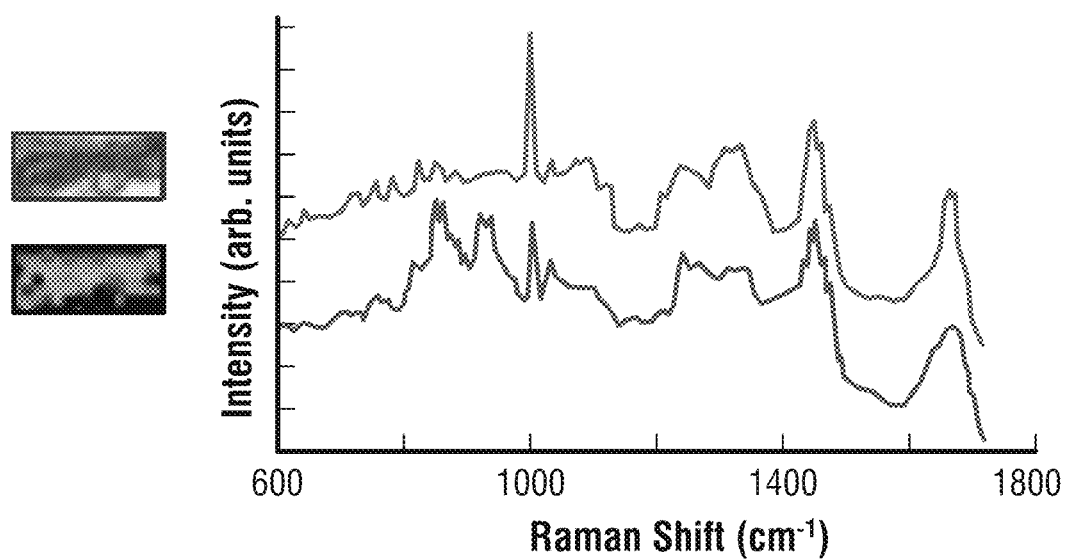

RF fused blood vessels and small bowel samples fused at different compression pressures were imaged using Raman spectroscopy. Raman maps were collected from selected regions within the tissue cross-sections including fused areas, undisturbed and thus considered 'healthy' areas, and the interface between them. Raman maps of selected regions are shown for a fused porcine blood vessel at 0.3 MPa compression (FIG. 13) and porcine blood vessels (FIGS. 15, 17 and 19). The Raman maps of selected regions of the porcine blood vessels are shown fused without compression (FIGS. 15A, 17A and 19A), with 0.2 MPa compression (FIGS. 15B, 17B and 19B), and with 0.3 MPa compression (FIGS. 15C, 17C and 19C). A white light micrograph showing the cross section of each tissue sample is shown in each figure (FIGS. 13, 15, 17 and 19) with rectangular boxes highlighting the areas that were mapped by Raman. The three areas that were selected for mapping included healthy tissue (FIGS. 13A, 15A, 17A and 19A), the interface between healthy and fused tissues (FIGS. 13B, 15B, 17B and 19B), and fused areas (FIGS. 13C, 15C, 17C and 19C). The resulting Raman map and the end-member spectra identified in the sample and used to construct the Raman map are shown in FIGS. 13 through 20C. All Raman maps shown were reconstructed from the two end-member as shown in spectra in each panel.

The bottom spectrum (in red) representing the collagen end-member spectrum within the sample and the top spectrum (in green) representing the non-collagen rich tissue are shown. The collagen end-member spectrum identified by the N-FINDR algorithm in each map includes all the characteristic features reported in past Raman studies of collagen and collagen rich tissues. Specifically, Raman bands corresponding to C—C stretch of proline (855 cm$^{-1}$), C—C stretch of hydroxyproline (874 cm$^{-1}$), C—N stretch of proline (919 cm$^{-1}$), proline (1043 cm$^{-1}$), and Amide 3 (1245-1270 cm$^{-1}$) are notable. The hydroxyproline and two proline peaks identified in these spectra are specifically Raman collagen assignments confirming a collagen presence. The end-member spectrum which was identified to be non-collagen rich tissue included spectral features indicative of biological tissue including bands corresponding to cholesterols (699 cm$^{-1}$), phenlalanine (1003 cm$^{-1}$), C—H deformation of proteins (1262 cm$^{-1}$) and carbohydrates (1342 cm$^{-1}$), amide II (1480 cm$^{-1}$), and amide I (1663 cm$^{-1}$).

Figure 21:
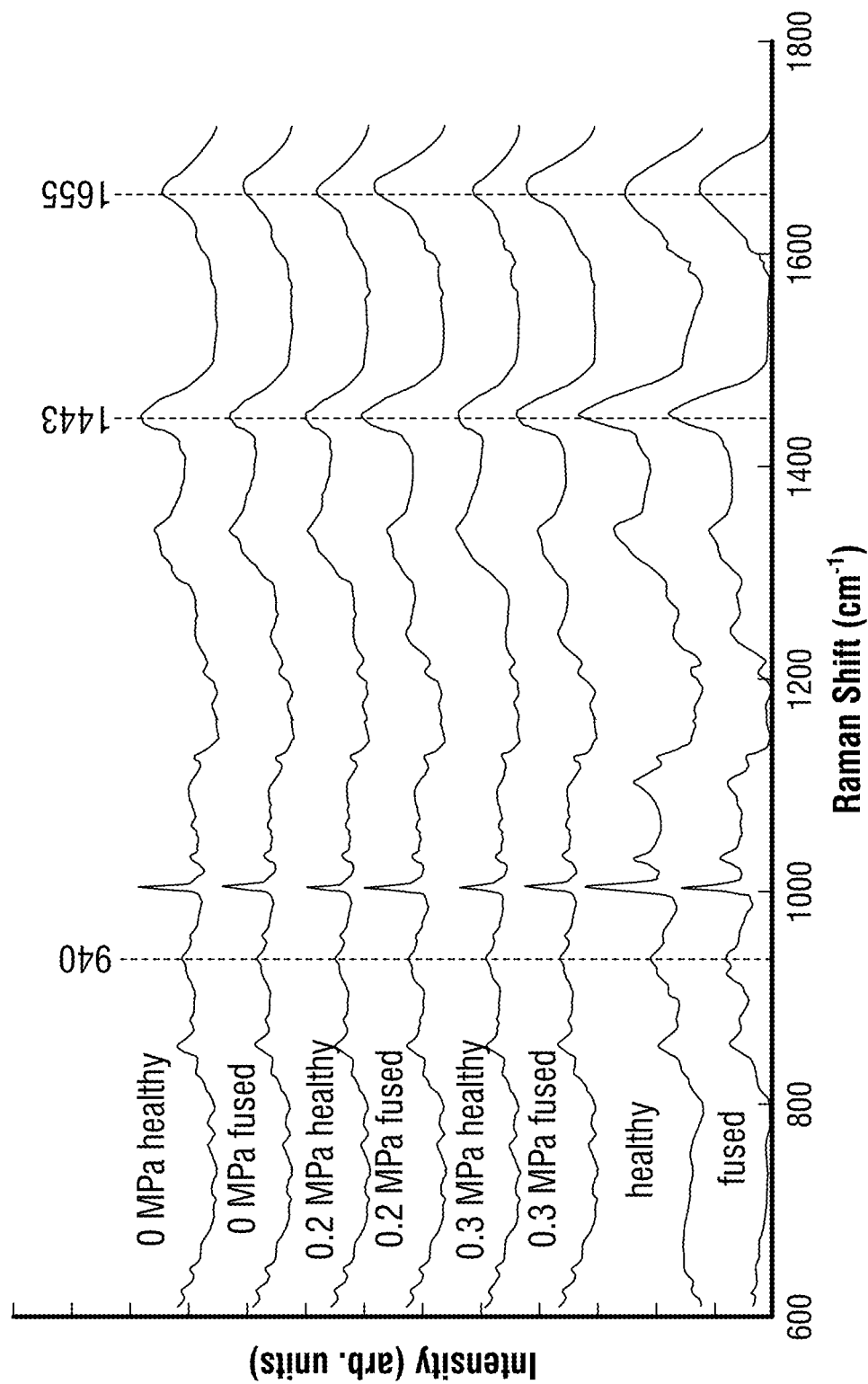
FIG. 21 is a graph illustrating mean Raman spectra of healthy and fused tissue areas mapped in porcine blood vessel and bowel tissue in accordance with an embodiment of the present disclosure.

FIG. 21 shows mean Raman spectra of healthy and fused tissue areas mapped in porcine blood vessel and bowel tissue. Each spectrum labeled "healthy" represents the mean of all collected spectra from an undisturbed cross section of the tissue. Each spectrum labeled "fused" represents the mean of all collected spectra from the fused cross section of the tissue. Grey spectra were collected from porcine blood vessel tissue with and without radio frequency fusion at 0.3 MPa compression as labeled. Spectra shown in black were collected from porcine bowel tissue with the corresponding compression pressure labeled (in healthy spectrum, the pressure of the adjacent fused tissue is indicated in the label). Raman 940 cm$^{-1}$, 1443 cm$^{-1}$ and 1655 cm$^{-1}$ peaks are highlighted corresponding to the protein alpha helix, CH2 wag, and the Amide 1 C—N—H stretch respectively.

The mean of all spectra collected from the healthy and fused areas of the blood vessel which underwent RF fusion and the bowel tissues which underwent RF tissue fusion at 0, 0.2 MPa and 0.3 MPa compression pressure are shown in FIG. 21. In both the blood vessel and the bowel tissues a shift in the peak maximum occurred in the 1663 cm$^{-1}$ Amide 1 band and a change in band shape was observed in the 1443 cm$^{-1}$ C—H bending band when comparing the fused mean spectrum from the healthy mean spectrum in each sample. Many peaks, including the 940 cm$^{-1}$ peak representing the protein alpha helix did not appear to change peak position or shape.

Figure 22A:
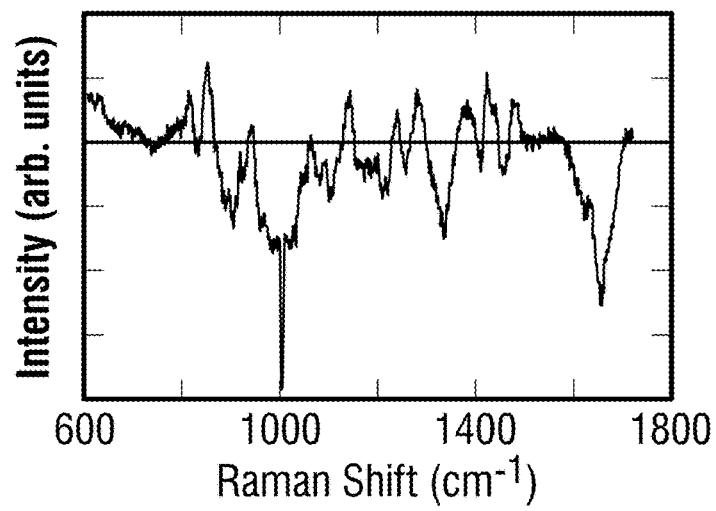
FIG. 22A is graph illustrating a fused porcine blood vessel in accordance with an embodiment of the present disclosure.
Figure 22B:
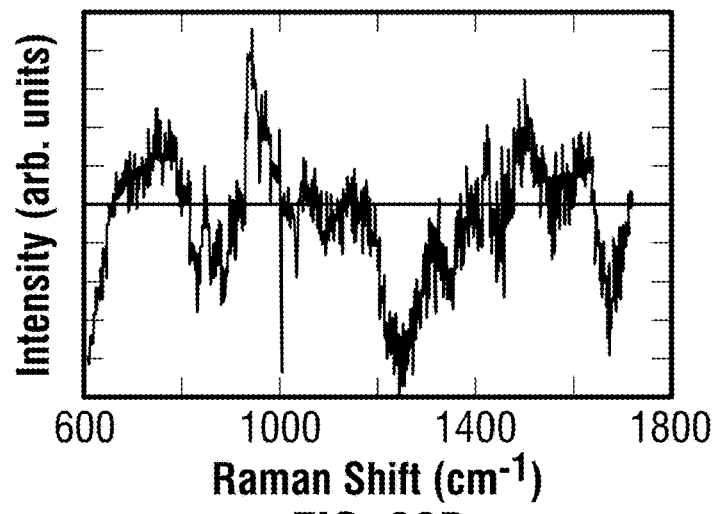
FIG. 22B is graph illustrating fused porcine bowel tissue without compression in accordance with an embodiment of the present disclosure.
Figure 22C:
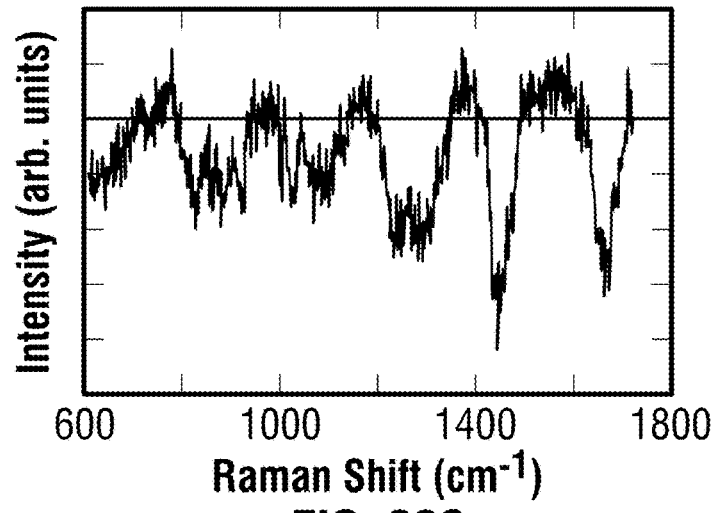
FIG. 22C is graph illustrating porcine bowel tissue fused at 0.2 MPa compression pressure in accordance with an embodiment of the present disclosure.

Changes specifically in the collagen rich environments were investigated through a threshold analysis using the end-members identified with the N-FINDR algorithm. Spectra showing an abundance value greater than 0.6 of the collagen rich end-member were selected and the mean of these spectra was then calculated for each map. These means were then compared between healthy and fused areas to identify changes in the collagen environment due to fusion via a difference spectrum (FIGS. 22A, 22B and 22C). Fused porcine blood vessel tissue showed the changes in the 1252-1261 cm$^{-1}$ peaks and a shift to lower wave-numbers in the 1447 cm$^{-1}$ peak. The 1600-1650 cm$^{-1}$ Amide 1 band showed a shift to higher wave-numbers. For the bowel tissues, different changes were noted corresponding to different fusion parameters; however, only the samples which were fused with no compression and at 0.2 MPa compression was used for comparison as these sample maps included more than 3 spectra which met the threshold requirements. The changes in the collagen rich spectra between fused and healthy areas were less pronounced in the porcine bowel tissue samples when compared to fused blood vessels. In comparison to fused blood vessels, bowel tissue fused at 0.2 MPa compression pressure demonstrated similar trends in the protein band shifts, specifically in the three broad protein bands, 1245-1270, 1445, and 1665 cm$^{-1}$, corresponding to the Amide 3, CH$_2$ bending, and Amide 1 bands, respectively, though less distinct. In bowel tissue fused without compression, band shift trends included the 1245 and 1665 cm$^{-1}$ Amide 3 and Amide 1 band, respectively; however, less dramatic shifts were seen in other protein bands (FIGS. 22A, 22B and 22C).

Referring to FIGS. 22A, 22B and 22C, Raman spectra are shown of healthy, RF-fused collagen rich tissue areas from RF fused porcine blood vessel (FIG. 22A), RF-fused porcine bowel tissue without compression (FIG. 22B), and at 0.20 MPa compression pressure (FIG. 22C). The 1313 cm$^{-1}$, 1324 cm$^{-1}$, 1252-1261 cm$^{-1}$ and 1600-1690 cm$^{-1}$ peaks are highlighted corresponding to the CH3CH2 twisting and wagging mode of collagen, respectively; Amide 3 and Amide 1 (nonreducible collagen crosslinks at lower wave-numbers and reducible collagen crosslinks at higher wave-numbers) respectively.

Histopathology Results

Figure 23A:
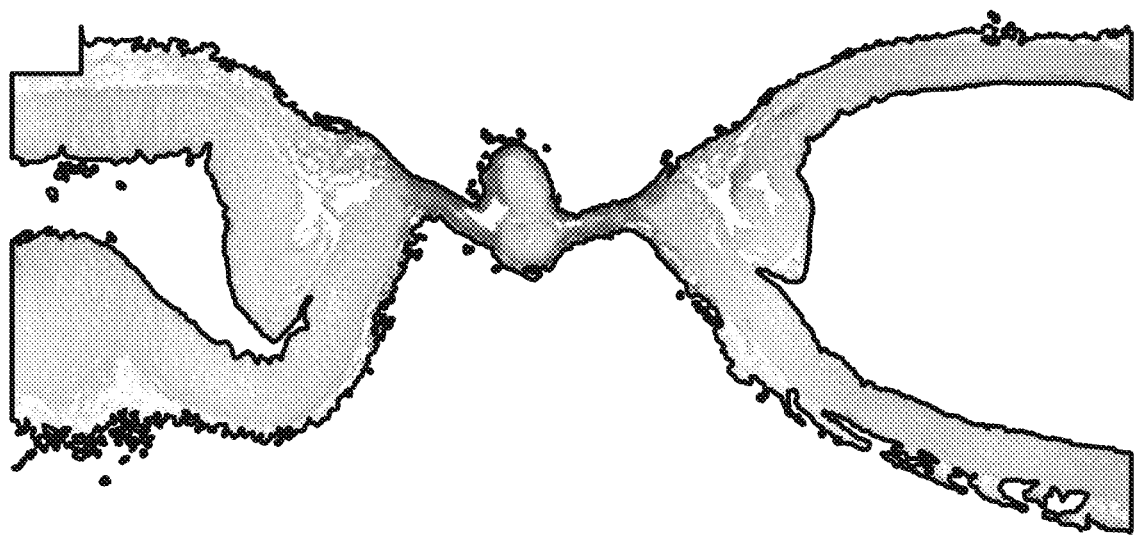
FIG. 23A is an illustrative representation of a histological section of a fused porcine blood vessel sample in accordance with an embodiment of the present disclosure.
Figure 23B:
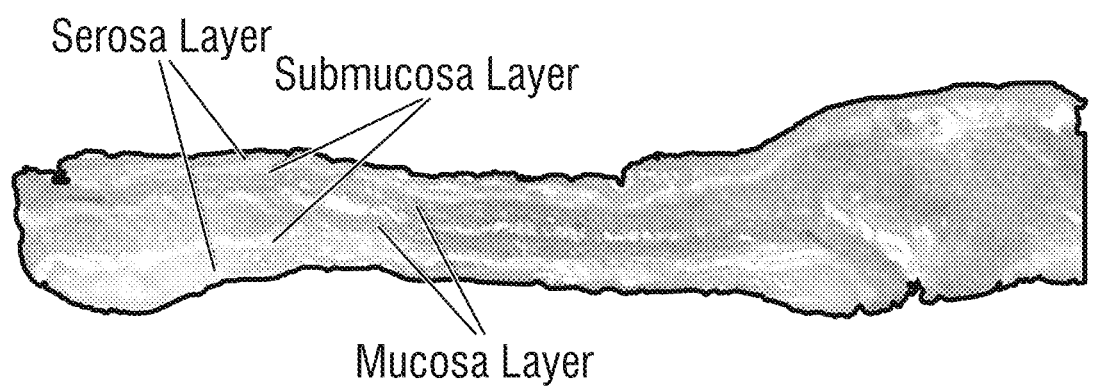
FIG. 23B is an illustrative representation of a histological section of a porcine small-bowel sample fused at 0 MPa in accordance with an embodiment of the present disclosure.
Figure 23C:
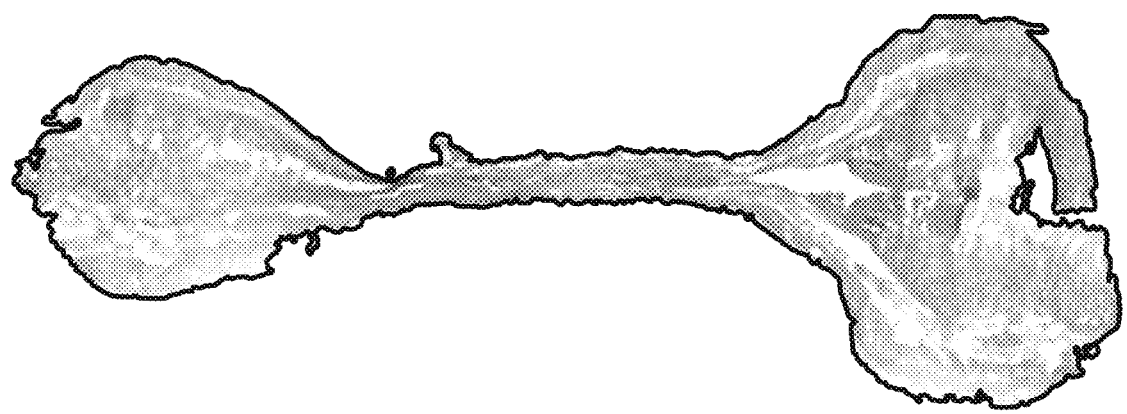
FIG. 23C is an illustrative representation of a histological section of a porcine small-bowel sample fused at 0.2 MPa in accordance with an embodiment of the present disclosure.
Figure 23D:
FIG. 23D is an illustrative representation of a histological section of a porcine small-bowel sample fused at 0.3 MPa in accordance with an embodiment of the present disclosure.

FIGS. 23A through 23D show histological sections of fusion samples for: porcine blood vessel (FIG. 23A); porcine small-bowel sample fused at 0 MPa (FIG. 23B); porcine small-bowel sample fused at 0.2 MPa (FIG. 23C); and porcine small-bowel sample fused at 0.3 MPa (FIG. 23D).

In FIGS. 23A through 23D, the histopathology results are presented for both porcine blood vessels and porcine small bowels fused at different compression pressures. The porcine small bowel tissue sample fused at no compression pressure, as shown in FIG. 23B, appears to form a seal between the upper and lower small-bowel pieces, where the boundary between these two layers can still be seen. The three layers of small bowel tissue, i.e., serosa, submucosa and mucosa layers, can be clearly identified and the delimitations between different layers are apparent. Although the tissue thickness was reduced at the mucosa layer, the tissue structure remains similar to the native tissue. FIGS. 23C and 23D show porcine small-bowel samples fused at compression pressures of 0.2 and 0.3 MPa. Relative to FIG. 23B, FIG. 23C and FIG. 23D display significant changes in the tissue structure resulting from the applied compression pressure. The delimitation between submucosa and mucosa layers is less clear and the thickness of the mucosa layer has reduced considerably. Importantly, a more homogeneous amalgam was formed by the upper and the lower mucosa layers in the centre of the fusion region, and the boundary between the upper and the lower mucosa layers has completely disappeared.

Tissue Temperature Evolution During Fusion

The embedded thermocouple shows that the tissue temperature evolution during fusion has two stages: a rapid increase in tissue temperature within a few seconds followed by a relatively stable plateau where the tissue temperature variation was within the range of ±5° C. The tissue temperature was determined by the impedance control algorithm. A steep rising slope significantly reduces the duration of the whole procedure and a higher plateau temperature in the range between 60° C. to 90° C. ensures the necessary collagen denaturation in the tissue, which is believed to be essential for a strong fusion. It was discovered that plateau temperatures below 60° C. may not lead to the denaturation of collagens, while excessive temperatures need to be avoided as these lead to permanent damage of the tissue or necrosis.

Discussion of the Raman-Spectroscopy Analysis

RF tissue fusion holds promise to reduce some of the complications in existing bowl anastomosis procedures including post-operative bleeding and leakage. One of the challenges in intestinal tissue anastomosis is effectively controlling the delivered energy to form a successful fusion without causing excessive thermal tissue damage. This requires a better understanding of the heat-induced tissue fusion mechanism and the development of effective feedback technologies.

This study investigated the use of Raman spectroscopy to provide biomolecular insights into the molecular restructuring which occurs during tissue fusion. Raman results were linked to optimal fusion parameters (compression pressure in particular) obtained by comparing to the BP testing results and histological sections. Raman spectroscopy was conducted in order to explain the observed changes in mechanical strength shown in the BP measurement of fusions when compression pressure was changed. Raman spectroscopy was applied to non-invasively image cross sections of healthy and fused tissue as shown in FIGS. 13 through 20C. Applying N-FINDR spectral unmixing allowed for visualisation of the various bowel tissue layers by identification of the end-member spectra which are defined by the most extreme spectra present within the map. The tissue layers identifiable through Raman spectroscopy correspond to those layers seen in the white light micrographs and in the histological sections by utilizing only two end-member spectra, one corresponding to a high collagen contribution and the other to non-collagen rich tissue. Raman spectroscopic maps were reconstructed from the two end-members with end-member abundance plots overlaid and converted to red green colour images based of the contribution of each end-member to each collected spectrum. The submucosal layer is clearly distinguished in each small intestinal cross section by its increased collagen content. During sectioning of the intestinal tissue, the shear force caused some separation of the healthy tissue sublayers (serosa, submucosa and mucosa). In FIG. 16A, a loss of the serosa is clearly visible in the white light micrograph and the corresponding Raman map. The collagen rich submucosa is located between the mucosa and serosa. The mucosa and serosa are shown to include many of the Raman spectral signatures of biological tissues including cells (DNA peaks included) and the extracellular matrix. Collagen Raman signature bands are found in the mucosa and serosa layers as well; however, these layers appear to be less collagen rich with a greater cellular contribution corresponding to the known constituents of these tissue layers.

Histopathology results show the fused tissue area to be thinner and lacking the tissue layers visible in healthy tissue. The merging and restructuring of the biochemical constituents of the tissue layers in the bowel tissue during RF tissue fusion with compression pressure is only significantly demonstrated in the Raman maps. At a compression pressure of 0 MPa, the fused area is visibly thicker, and the tissue layers are still distinct as shown with the white light images and histology. The Raman map shows this again with the collagen rich layers remaining very distinct and encased by non-collagen rich layers as seen in FIGS. 17 and 19. As the compression pressure was increased to 0.2 MPa the greatly reduced thickness of the fused area made it hard to visually distinguish if the native tissue layers were still preserved post RF fusion. At 0.2 MPa compression pressure the Raman map exposed a collagen rich upper and lower layer in some areas of the fused region and less distinguishable collagen layering in other areas (FIG. 17). Further, at a compression pressure of 0.3 MPa there was no distinct layering of collagen rich and non-collagen rich regions within the fused tissue and collagen rich areas are found throughout the thin fused area. The collagen within the fused region of samples which underwent compression also demonstrated collagen cross linking modification and collagen amide bond modification which were not detected in tissue fused without compression. When comparing these results to the burst pressure measurements, it is notable that both the 0.2 MPa and 0.3 MPa compression pressure fused tissues showed median burst pressures of more than 20 mmHg. The correlation of higher burst pressures in the compressed fused tissue samples with less distinct tissue layering and a more distinct change in collagen crosslinking supports the hypothesis that collagen crosslinking modification via RF fusion plays an important role in the overall quality of the tissue fusion.

H&E histological stains of the porcine small intestinal tissue showed that fusion without compression produced a decrease in the tissue cross sectional thickness however the tissue layers and band structures appeared to remain much like that of the native state and produced a median burst pressure of less than 10 mmHg. RF tissue fusion performed with accompanying compression showed a dramatic reduction in fused tissue thickness and significant changes in the tissue layers with the delimitation between the submucosa and mucosa layers becoming less distinguishable as seen in FIGS. 15 through 20C and FIGS. 23A through 23D. Additionally, the upper and lower mucosa of the fused tissue become indistinguishable from one another in the histological sections, white light micrographs and Raman maps. Fusion is therefore demonstrated by the unification of the mucosa during fusion along with the increase in burst pressure.

This method compares the collagen rich spectra from healthy and fused tissue. In order to perform this analysis the collagen rich spectra were identified by those having an abundance value greater than 0.6 for the collagen end-member spectrum found in each Raman map. The mean of all spectra which were identified to be predominantly collagen was then calculated and the healthy and fused tissue collagen was compared through the difference spectra of these collagen means as shown in FIGS. 22A through 22C. This analysis was performed on both fused porcine blood vessels as well as fused porcine bowel tissue. The difference spectrum comparing areas of fusion to healthy tissue in blood vessels showed similar band shifts and thus biomolecular bond changes in two independent samples. These trends included the denaturing of collagen shown through the shift of the 1660 $cm^{-1}$ band to higher wave-numbers in the fused tissue area, also suggesting an increase in reducible crosslinks and a decrease of non-reducible cross links within the collagen. Additionally, a shift in the 1302 $cm^{-1}$ peak to higher wave-numbers has been previously reported in collagen thermal denaturing. Changes in the 1313 $cm^{-1}$ and 1324 $cm^{-1}$ peaks signifying changes in the $CH_3CH_2$ twisting and wagging modes of collagen also demonstrated a disruption to the native collagen. Lastly, the apparent shift of the 1252-1261 $cm^{-1}$ peaks to lower frequencies also implicate crosslinks may have been reduced or broken. RF fusion of the porcine bowel tissue demonstrated less pronounced differences; however, fusion performed at 0.2 MPa compression pressure demonstrated many of the same changes, including shifts in the 1252-1261, 1313, 1324, 1443, and 1660 $cm^{-1}$ bands, seen in the fused blood vessels, again indicating a denaturing of collagen and, more specifically, a decrease in non-reducible cross links and an increase in reducible cross links as seen in FIG. 23C.

Tissue fused without compression appears to undergo some molecular restructuring as indicated in the mean plots (FIG. 21) which may be expected due to exposure to higher temperatures. This molecular restructuring appears to be less collagen dependant as shown in the Raman difference plots in FIG. 22B with collagen difference spectrum highlighting fewer distinct band shifts in compressed tissue versus non-compressed tissue. This may be attributed to more collagen bond restructuring with the additional mechanical pressure during fusion introduced with tissue compression.

Particular consideration to Raman spectral background changes was taken during the analysis of the Raman tissue maps as fiber and water content may alter the Raman background signal. A polynomial fit was used to remove the background and spectra were normalised before comparing means directly or through difference spectra. Changes within the Raman spectral backgrounds were in line with expectations with the fused regions being more dense, less hydrated and less organized into distinct tissue layers. Some of the difference spectra were not considered (i.e., 0.3 MPa compression pressure) as those tissue areas showed less than 3 spectra with an abundance value greater than 0.6 for the collagen rich end-members. When comparing difference spectrum it is also important to note collected Raman spectra are semi-quantitative thus general trends (peak shifts and shape changes) are more comparable than absolute intensity differences. It is contemplated that smaller mapping step sizes and/or a larger tissue section may be considered to improve upon these challenges.

As shown herein, the correlation between the Raman maps and the histological maps supports the utilization of Raman spectroscopy in the investigation of RF tissue fusion quality and tissue restructuring. The presently-disclosed method of Raman spectroscopy allowed for highly spatially resolved mapping that provided biochemical information without suffering from hydration and tissue density changes between the healthy and fused tissue. The information rich nature of the collected Raman spectra combined with multivariate statistical analysis allowed the selection and comparison of the collagen content between tissue sections of interest. These abilities may be utilized when investigations of RF tissue fusion and comparable techniques are compared in situ and in vivo. Raman microscopy has been demonstrated to be translatable into the clinical setting. Thus the rapid, non-destructive, hydration and dehydration-compatible technique utilized in this study holds promise to further elicit information in the translation of the technique to bowel anastomoses.

Laser-Induced Tissue Fluorescence in Monitoring RF Tissue Fusion Method

The use of heat for tissue sealing or approximation has attracted much attention in many surgical fields. For example, heat-induced vessel sealing by energy-based devices has been experimentally studied and clinically implemented for some time. Different energy sources have been used for tissue heating and fusion, including ultrasound, RF, and laser energy. Of these, ultrasonic dissectors (e.g., Cusa, Cavitron Ultrasonic Surgical Aspirator, Covidien, USA; Selector, Surgical Technical Group, Hampshire, GB; Autosonix Autosuture, Norwalk, Conn., USA; Ultracision, Ethicon Endo-Surgery, Norderstedt, Germany) and RF bipolar vessel sealers (e.g., LigaSure Impact™, Covidien, Boulder, Colo.) are commercially available and clinically used as common practice in the operating theater.

The method described herein presents a novel tissue fusion monitoring and characterization technology using laser-induced fluorescence spectroscopy, which provides further insight into tissue constituent variations at the molecular level. In particular, an increase of fluorescence intensity in 450-550 nm range for 375 and 405 nm excitation suggests that the collagen cross-linking in fused tissues increased. Experimental and statistical analyses showed that, by using fluorescence spectral data, good fusion could be differentiated from other cases with an accuracy of more than 95%. This suggests that fluorescence spectroscopy can be used as an effective feedback control method in real-time tissue fusion.

Bowel anastomosis is a routine procedure in modern surgery to restore bowel continuity after surgical resection due to intestinal malignancy, inflammation or obstruction. It has been estimated that 2.5 million bowel anastomoses are performed annually worldwide. The existing tissue anastomosis techniques of suturing and stapling may have limitations and problems such as bleeding and leakage from suturing sites. These complications may result in trauma, infection, and retained foreign materials, leading to a significant increase in morbidity, mortality and additional cost in treatment. Energy-based anastomosis devices hold the promise of replacing hand-suturing and stapling in surgery to become the next generation anastomosis technology. Such a technology exploits the heat-induced anastomosis of native tissues. High-quality tissue sealing as a result of simultaneously applied heat and compression pressure can be achieved without using any foreign materials, and thus, is expected to greatly reduce morbidity, mortality and additional treatment cost.

There are two main challenges that need to be addressed in this field. Firstly, although the mechanism for heat-induced tissue fusion, particularly for blood vessel sealing, has been studied, such a process is not fully understood on a molecular level. Secondly, existing thermotherapy procedures mainly rely on predetermined dosimetry such as heating power or applied voltage. In bowel anastomosis, however, due to the complex and variable nature of bowel tissue, instead of predetermined dosimetry, a monitoring or feedback control strategy should be implemented in real time. Parameters including temperature, thermal spread, optical transmittance and impedance have been suggested, but it has been unclear how these parameters may provide insights into molecular structural changes.

The presently-disclosed method uses laser-induced fluorescence from endogenous fluorophores to noninvasively characterize tissue. Variation in laser-induced fluorescence properties is often due to changes in fluorophore concentration, fluorophore spatial distribution, metabolic state, biochemical/biophysical microenvironment, tissue architecture, and attenuation arising from chromophores and scatterers. The endogenous fluorophores in tissues consist of collagen crosslinks (excitation: 360 nm; maximum emission: 450 nm), elastin (325 nm; 400 nm), NAD(P)H (351 nm, 460 nm), FAD (450 nm; 535 nm), bile (380 nm; 425 nm) and lipopigments (broad excitation and emission). The laser-induced fluorescence spectrum mainly arises from the superposition of the fluorescence from all of these fluorophores.

Intestinal tissues share many compositional similarities with other tissue types, including the fluorophore content such as collagen and elastin. The gastrointestinal tract consists of four distinct layers (mucosa, submucosa, muscularis, serosa) that possess different fluorescence characteristics due to variations in fluorophore composition and arrangement. The submuscosa is by far the most fluorescent layer for ultraviolet (UV) excitation due to its high collagen content, and this can be used as the basis of characterization of intestinal tissues subject to heat using laser-induced fluorescence. This method involves the fluorescence emission from collagen crosslinks, which are an important indicator for tissue fusion mechanical strength. Further, the methods of fluorescence spectroscopy may be fast, noninvasive and quantitative. Considering that only a few points need be probed and that certain discrete spectral features can be used to create a diagnostic indicator, the presently-disclosed fluorescence spectroscopy method may be a relatively inexpensive and accessible modality to implement and use.

In accordance with the method described herein, heat-induced porcine small-bowel fusion was performed by using RF energy and demonstrates the use of laser-induced fluorescence to characterize fusion in vitro. Histopathology analysis was conducted to gain direct knowledge into the fused-tissue architectural changes. Fused-tissue mechanical strength was assessed by a burst pressure (BP) testing system. The tissue fluorescence spectra was measured with two excitation lasers at 375 and 405 nm, and the difference in the fluorescence spectra in relation to the quality of fusion was investigated. Using laser-induced fluorescence to determine the fusion quality is also discussed.

Materials and Methods of the Laser-Induced Tissue Fluorescence in Monitoring RF Tissue Fusion Method Animal Tissue Preparation Fresh porcine small bowels were obtained from a local abattoir, cut into 20-30 cm long segments, moistened with physiological saline and refrigerated at 4° C. for up to 30 hours (from the time of slaughter) until needed for fusion experiments. Prior to the fusion experiment, a segment of small bowel was selected and immediately dissected into 5 cm-long pieces for tissue fusion experiment. Prepared 5 cm samples were kept hydrated in sealed plastic sample bags with saline and used within 30 minutes.

RF Tissue Fusion

RF energy is used as the source for tissue heating. The RF generator is an energy research tool prototype (developed by Covidien, Boulder, Colo.) capable of delivering a programmable sinusoidal current from 0-7 A and a power from 0-350 W. An operating RF frequency of 472 kHz was chosen to avoid neuromuscular stimulation and electrocution. A bipolar anastomosis prototype was used as the tissue sealing device in this experiment with jaws to clamp on the tissue sample, with RF energy supplied by the embedded electrodes in the jaws during the application of compression pressure provided by an air compressor connected to the jaws. Pre-written RF energy control algorithms were loaded into the tissue fusion software written in LabVIEW (National Instruments Corporation, Austin, Tex.) in the PC to control the entire procedure. The algorithm was configured to control RF energy delivery to ensure a predetermined variation in tissue impedance profile, that is, to firstly raise the tissue impedance rapidly to a starting threshold, and then to maintain a slowly rising impedance until the impedance finally reaches the pre-set end-impedance During RF fusion, a piece of porcine small-bowel sample was clamped between the fusion device jaws. The RF generator supplied the RF energy and also continuously monitored both the voltage and the current delivered to the tissue. The varying tissue impedance was then obtained by using the real-time voltage and current readouts. The air compressor was capable of supplying a variable compression pressure from 0-0.5 MPa via a pneumatic system integrated with the anastomosis prototype device.

Temperature Measurement

Tissue temperature was measured using a fine (0.005 inch) tip Teflon-insulated J-type thermocouple (5TC-TT-J-36-36, Omega Engineering, Bridgeport, N.J.). The thermocouple was inserted through slits made on the sealing device jaws and glued in place at the top of the slit so that its tip emerged 0.25 mm above the electrode surface. In this way the thermocouple was in contact with the tissue surface without piercing it, and was insulated from the electrodes. The communication between the thermocouple and the computer was achieved through a National Instruments (NI) PXI-6289 DAQ board and an NI SCC-68 terminal block. The latter hosted four NI SCC-TC02 Thermocouple Signal Conditioning Modules. Each SCC-TC02 could drive one thermocouple and had individual signal conditioning modules with a 2 Hz low-pass filter, which filtered out the RF signal and eliminated the RF interference from the thermocouple readout.

Laser-Induced Tissue Fluorescence Measurement

The UV laser fluorescence system employed two excitation laser diodes emitting at 375 nm and 405 nm. These excitation wavelengths were selected in order to determine the endogenous fluorescence properties of various tissue samples. A custom made fiber-optic probe (Romack, Inc., Williamsburg, Va.) formed a two-way laser delivery and fluorescence collection device, consisting of six hexagonally packed collection fibers surrounding an excitation fiber. The diameter and numerical aperture of the fibers were 200 µm and 0.22 respectively and the fiber material was chosen to have low autofluorescence and attenuation in the UV spectral region of interest. The probe distal tip was covered by a glass window and the fibers and window were housed in a stainless steel tube with an external diameter of 2 mm. This configuration enabled it to be inserted into small slits made on the sealing device jaws for real-time analysis. The proximal end was divided into two arms, the first arm contained the excitation fiber and was coupled to the laser optics using an SMA connector; the second arm included the six emission fibers arranged in a linear array inside another SMA connector. During laser-induced fluorescence, the proximal end was made perpendicular to the sample plane, in gentle contact with the sample without inducing any pressure.

The laser outputs were collimated by 4.6 mm focal length lenses and the beams were coupled into the excitation fiber using an 8 mm achromatic focusing lens. Two steering mirrors were used to optimize the alignment and maximize the coupling efficiency. Two program-controlled beam shutters were placed in front of laser diodes to switch laser exposure on and off as well as to control the exposure durations. The output optical power at the distal end of the probe was 3.5 mW.

The fluorescence emission from the six collection fibers was focussed onto the 80 µm wide input slit of an imaging spectrograph (Spectral Imaging Ltd., Oulu, Finland) using an achromatic lens doublet (60 mm and 30 mm). A 430 nm longpass filter was inserted between these two lenses to block the excitation laser reflections from the sample. The light dispersed by the prism-grating-prism element of the spectrograph was then acquired with a sensitive cooled CCD camera (e.g., Retiga EXI, QImaging, Surrey, Canada, 1392× 1040 pixels). All the optical components were assembled together using a cage system and a breadboard so that the system was robust and portable. A LabVIEW program controlled the exposure time and beam shutters and enabled acquisition of fluorescent signals from the laser diode with an adjustable number of measurements.

Burst Pressure Measurement

The mechanical strength of the fused tissue was evaluated by a BP testing system that included a syringe pump, a pressure gauge, a sample injection needle and a surgical clamp to close the small bowel tissue. The main arm of a Y-splitter tubing system was connected to a water-filled syringe controlled by the syringe pump. The other two split arms were connected to the pressure gauge and the sample injection needle, respectively. The surgical clamp sealed the other end of the piece of fused small bowel to make it a "tissue balloon." The sample injection needle was used to pierce the small bowel tissue to allow water to be infused into the sealed bowel without damaging the seal. As the amount of water inside the tissue was increased at a rate of 20 mL/min using the syringe pump, the pressure also increased until the fused tissue leaked or burst at the fusion line, and the highest value of water pressure recorded by the pressure gauge was the BP.

Histopathology Analysis

To assess how the structural changes influence the tissue qualitatively, histological examination of RF-fused tissue was carried out. Samples of porcine small bowel were fused and histological sections were taken before and after fusion. The samples were dissected and conserved in formaldehyde, stained with haematoxylin and eosin (HE), sliced transversal to the seal, and were prepared on microscope slides.

Results of the Laser-Induced Tissue Fluorescence Analysis

Tissue Temperature Evolution During Fusion

The tissue temperature variation was a result of the variation in RF energy supplied to the tissue as determined by the specific impedance control algorithm used. The embedded thermocouple showed that the tissue temperature evolution during fusion had two stages: firstly tissue temperature rose rapidly from the initial tissue temperature to a higher value usually within a few seconds and then the tissue temperature became relatively stable, where the tissue temperature variation was within the range of 60° C. to 90° C. Such temperatures ensure the necessary collagen denaturisation and are believed to be essential for a strong fusion. Temperatures that are too low (<60° C.) may not cause denaturisation of collagen, and temperatures that are too high should be avoided in practice because it may lead to permanent damage on the tissue or necrosis.

Tissue Fusion and Burst Pressure Tests

Figure 24:
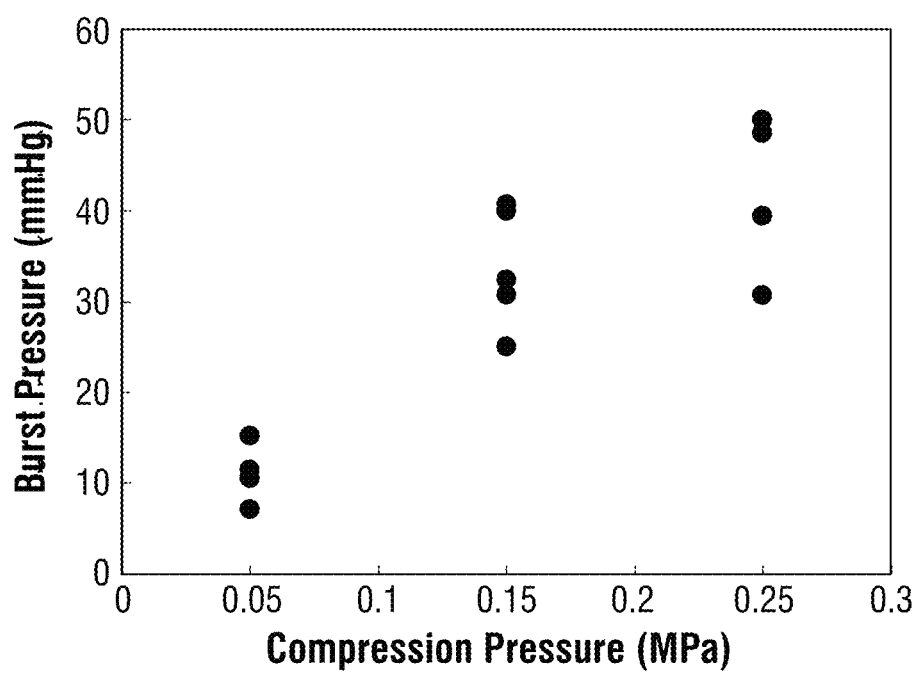
FIG. 24 is a graph of burst pressure test results versus fusion compression pressure in accordance with an embodiment of the present disclosure.

Tissue samples from the same animal were used in the fusion experiment. Fusions were carried out by controlling the RF energy in order to achieve a predetermined tissue impedance variation with a rising slope of 0.01 Ω/ms to an end impedance of 200Ω. Fifteen samples were fused with five at each of the following compression pressures: 0.05, 0.15, 0.25 MPa. Prior to fluorescence spectroscopy, the fusion strength of these samples was tested using the BP measurement device and results appear in FIG. 24. Fusions made at higher compression pressures (0.15 and 0.25 MPa) had a higher mean BP of ~40 mmHg. Samples fused at 0.05 MPa of compression pressure displayed an average BP of less than 10 mmHg. The histopathology and fluorescence spectroscopy results from these samples are given in the following sections to understand the difference in the fusion strength.

Histology

Figure 25A:
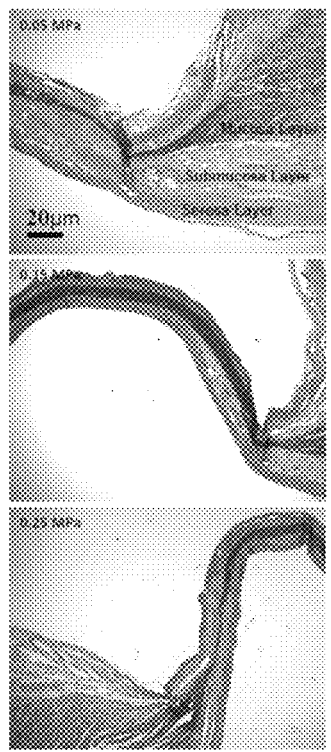
FIG. 25A is an illustrative representation of stained histology images for fused samples cut transversally across the fusion line in accordance with an embodiment of the present disclosure.
Figure 25B:
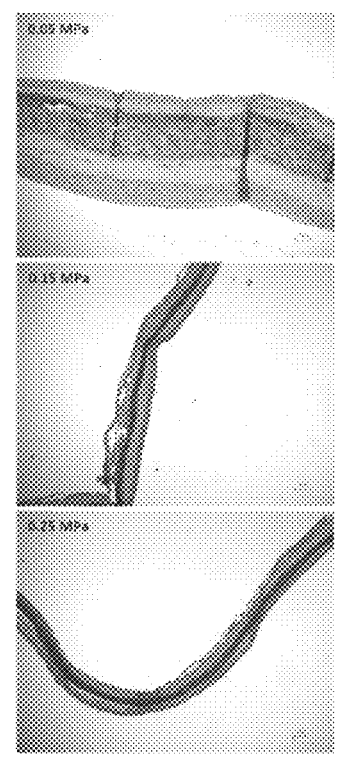
FIG. 25B is an illustrative representation of stained histology images for fused samples cut parallel to the fusion line according to in accordance with an embodiment of the present disclosure.
Figure 26A:
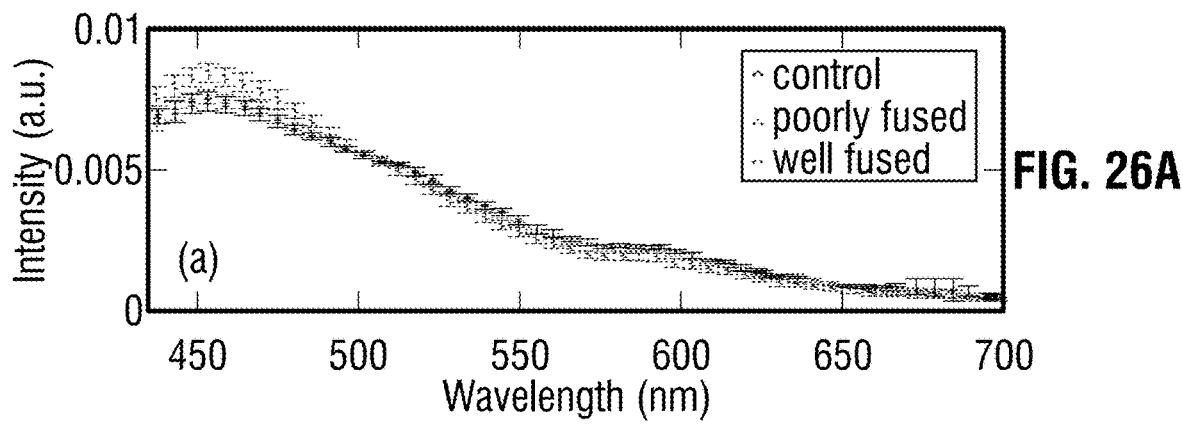
FIGS. 26A through 26D are graphs illustrating mean excitation spectra with standard deviation for "well-fused" versus "poorly fused" versus "control" samples in accordance with embodiments of the present disclosure.
Figure 26B:
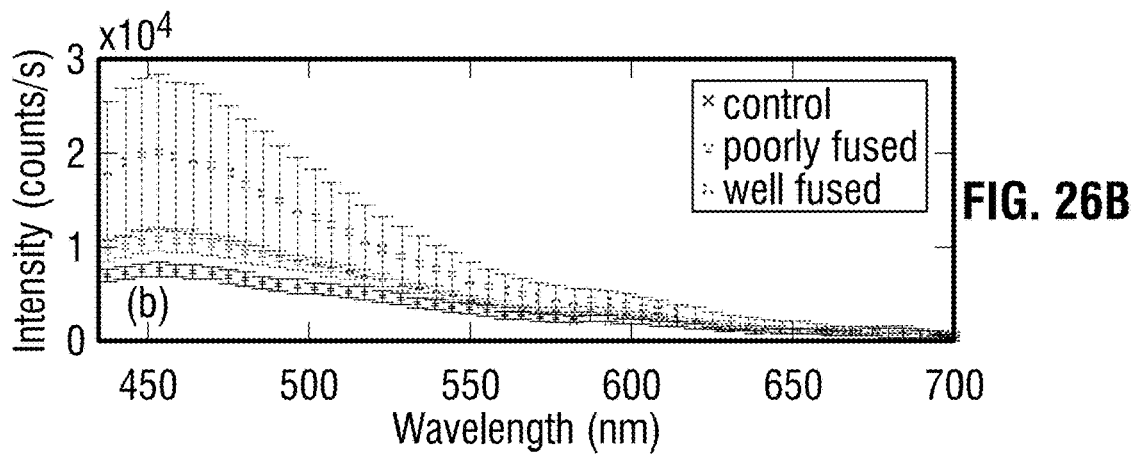
Figure 26C:
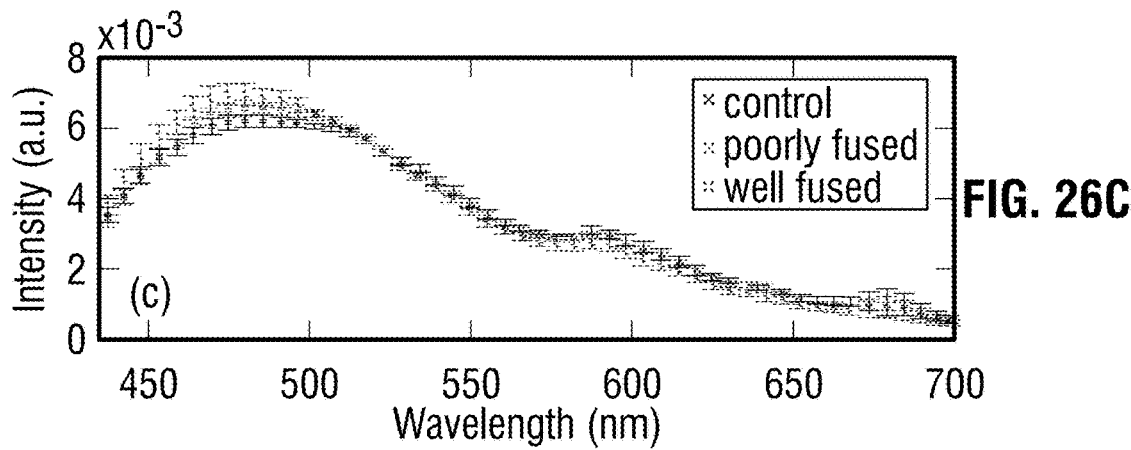
Figure 26D:
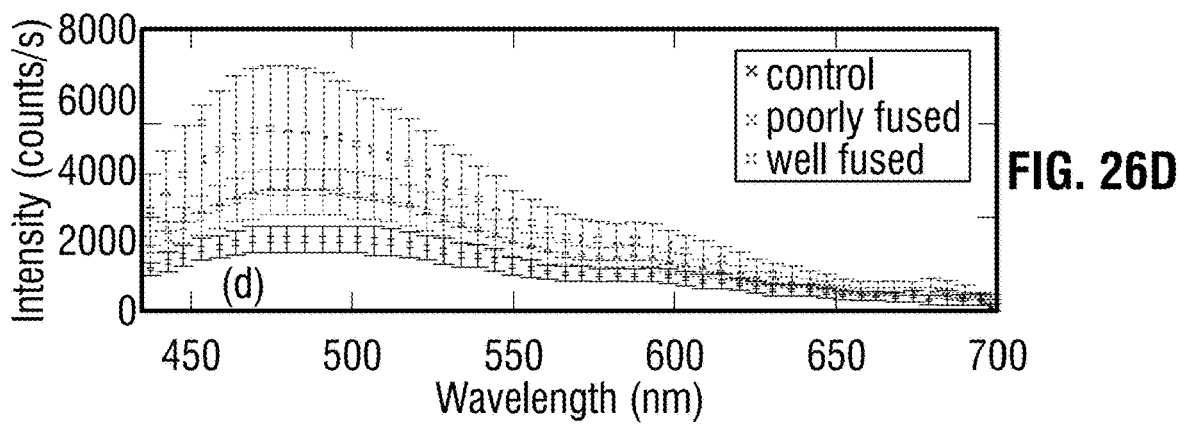
Figure 27A:
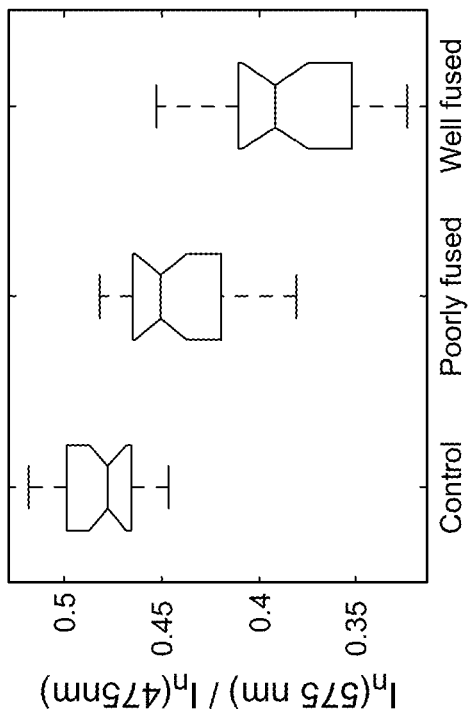
FIGS. 27A through 27D are boxplots for Kurskal-Wallis testing results in accordance with embodiments of the present disclosure.
Figure 27B:
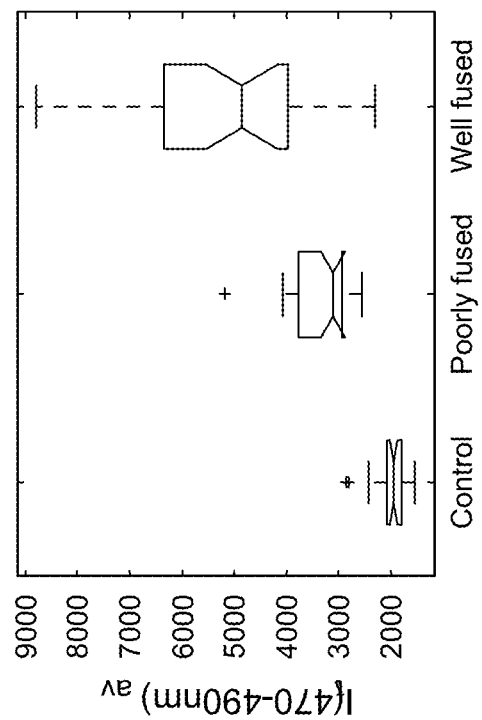
Figure 27C:
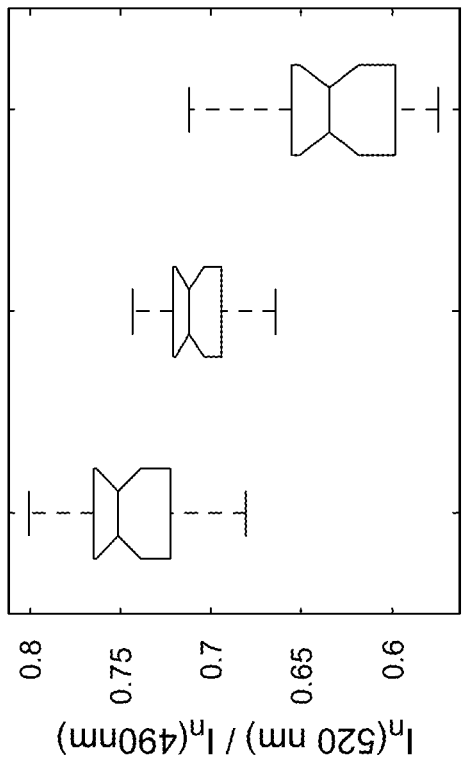
Figure 27D:
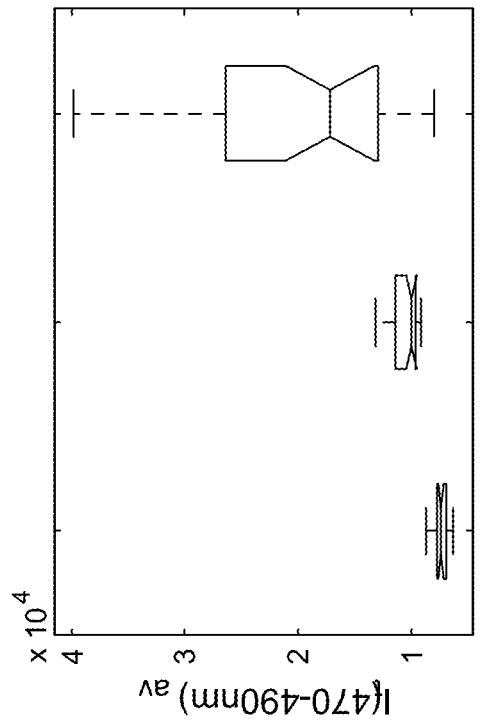

Histological images for fused samples are shown in FIGS. 25A and 25B. At 0.05 MPa, some degree of thermal damage, as well as tissue compression, can be seen. Residual muscle can still be identified, and clear demarcation among tissue layers can be observed. A higher compression pressure at 0.15 MPa resulted in a much thinner and homogeneous fused region, with the disappearance of structural features. Serosal and muscle layers were highly compressed, the submucosa and mucosa were merged into one homogenous layer, and a higher thermal damage could be seen. The observable features of fusions at 0.25 MPa compression pressure is similar to that of 0.15 MPa fusions, although some degree of cracking can also be seen, which might be due to the formation of steam vacuoles during RF fusion. Samples fused at 0.05 MPa of compression pressure were clearly under-fused. Samples fused at 0.15 and 0.25 MPa of compression pressure displayed similar architecture and features, being closer to a well-fused state. These histology results are consistent and reproducible among samples fused with equal fusion parameters.

Fluorescence Spectroscopy

In total, 804 fluorescence spectrum acquisitions were made on the fifteen fused tissue samples, with half made at each excitation wavelength (375 nm and 405 nm). Of these, 240 were "control" acquisitions on unfused tissue, 192 were "poorly fused" acquisitions at 0.05 MPa compression pressure, and 372 were "well-fused" acquisitions at 0.15 and 0.25 MPa compression pressures. FIGS. 26A through 26D show the mean fluorescence spectra and associated standard deviation error bars. For each excitation wavelength, both normalised (arbitrary units) and non-normalised (counts) spectra were displayed in order to show changes incurred to both waveform and overall intensity of the spectra.

The 375 nm laser excited mean fluorescence spectra displayed a main emission peak close to 455 nm, a slight shoulder around 500-515 nm, a secondary peak around 590 nm, and a narrow peak at 680 nm. The 405 nm laser excitation spectra showed a main peak in the 470-500 nm region, and a secondary peak around 590 nm. In the normalised spectra, the steepness of the 375 nm excitation spectra seemed to increase in the 460-550 nm region from the "control" to "poorly fused" and then to "well-fused" samples. In the control cases a shoulder was visible around 500-510 nm, which became less apparent for the increased fusion cases. For the normalized 405 nm excitation spectra, a slight blue-shifting seemed to occur around 475 nm, and this primary peak had greater intensity. In the non-normalised spectra, overall intensity appeared to increase with fusion, for both the 375 nm and 405 nm excited spectra in the 440-470 nm and 470-490 nm bands respectively. Additionally, not only did the average intensity increase with improved fusion, but there was also a greater variability in the magnitude of this intensity among the acquired spectra.

Data Analysis

Kruskal-Wallis non-parametric testing was applied to the fluorescence spectra and based on the features of the mean fluorescence spectra two spectral parameters were chosen: i) the ratio of normalized fluorescence emission intensity at two distinct wavelengths: $I_n(520 \text{ nm})/I_n(490 \text{ nm})$ for 375 nm excitation, and $I_n(575 \text{ nm})/I_n(475 \text{ nm})$ for 405 nm excitation; ii) the average normalised intensity between 440 nm to 470 nm for 375 nm excitation, and between 470 nm to 490 nm for 405 nm excitation, symbolized as $I_t(440\text{-}470 \text{ nm})_{av}$ and $I_t(470\text{-}490 \text{ nm})_{av}$, respectively. FIGS. 27A through 27D show the associated boxplots for Kurskal-Wallis testing results. With the significant level $\alpha=0.05$, P-values obtained shows the means for these two parameters are significantly different among the different classes.

Sparse Multinomial Logistic Regression (SMLR) was applied to the spectral dataset, with the purpose of, resorting to the most relevant spectral features, enabling classification of data into three classes: control, poorly fused and well fused. Over four-hundred input samples were used, where each sample consisted of a concatenation of the normalised 375 nm and 405 nm excited spectra of a given acquisition, associated to its appropriate quality of fusion label. The fluorescence emission values in the 335 nm and 650 nm range were used as features in the SMLR test. To assess SMLR classification, a K-fold cross-validation strategy was adopted, where each subset contained the six non-independent acquisitions made during each probing, yielding K=67.

The general accuracy in classifying the test data was 94.3%. For well-fused tissue (as defined by burst pressure testing), it could be differentiated from poorly fused and control tissue via SMLR with 95.2% sensitivity, 95.4% specificity, 94.7% positive predictive value (PPV) and 95.8% negative predictive value (NPV). Poorly fused tissue could be distinguished from other tissue states with 89.5% sensitivity, 97.1% specificity, 90.5% PPV and 96.7% NPV. Control tissue could be distinguished from any fused state with 100% sensitivity, 100% specificity, 100% PPV and 100% NPV.

Discussion of Laser-Induced Tissue Fluorescence Analysis

The histological results in FIGS. 25A and 25B show that higher compression pressure during fusion led to significant changes to the tissue structures, with a homogeneous amalgam formed along the fusion line and the boundary between the upper and lower mucosa layers completely removed. The BP tests also confirmed that fusions where an amalgam was formed are stronger. The formation of the amalgam can be understood as a result of the combination of compression pressure and heating. When RF energy was applied to the tissue sample, the biological impedance of the tissue converted energy into heat, which led to an increase in the local tissue temperature. At temperatures higher than 60° C., collagen fibers start to be denatured, whereby the chains of collagen became untied and formed more cross-links amongst each other. The application of compression pressure compressed the elastin and, as a result, reduced the space between collagen fibers, which may have enabled and accelerated the formation of collagen cross-links. Therefore, it seems that the amalgam along the fusion line consists of increased collagen crosslinking, which consequently leads to strong fusions. The laser-induced tissue fluorescence spectra were believed to contain the additional information on collagen crosslinking, which are unavailable with existing tissue fusion characterization modalities.

From the bowel spectroscopic measurements described herein, spectral results seem to be consistent with existing large bowel ex vivo studies at both 375 and 405 nm. The main peak can be explained as collagen type I, NADH, FAD, and by additional bile and cholesterol contributions. Specifically, the 375 nm excited shoulder in the 500 nm region can be attributed to FAD and the 590 nm secondary peak might be related to lipopigments, or to increased haemoglobin absorption in the 540-580 nm region. The variable appearance of a peak at 680 nm for some of the acquisitions is thought to be correlated to the fluid bowel contents still existent in the luminal area of some samples. Bowel contents are rich in lipids, lipopigments (e.g., lipofuscin) and bile acids, all of which emit fluorescence above 600 nm for our excitation wavelengths. This would also explain why the 680 nm peak appears more often for control (FIGS. 26A through 26D), since in fused samples the fluid contents would have been expelled sideways.

Some previous studies coupling thermo-transformations to tissue fluorescence noticed decreases in intensity, whereas results in accordance with the presently-disclosed method show increases in intensity in the 440-500 nm range. This contradiction is understandable because the previous works studied the sole effect of laser damage on the tissue, or tissue necrosis, which is different than the process in RF fusion that aims to seal the tissue as opposed to causing damage. Changes in NADH and FAD fluorescence probably arise due to the fact that thermal damage leads to the destruction of cellular organelles, namely mitochondria, which might, in turn, alter NADH and FAD metabolic states or even destroy the molecules as a whole.

Increase in fluorescence emission intensity, especially in the 440-500 nm range, may arise from both collagen crosslinking and tissue architectural changes. On one hand, the RF energy-induced heating of tissue leads to the breaking of existing collagen bonds, and then new collagen crosslinks form as a result of applied RF energy and compression. On the other hand, the significant increases in fluorescence intensity are considered to be related to the general tissue architectural changes due to the joint action of RF energy and pressure. Firstly, as seen in the H&E sections, the thickness of well-fused bowel ranges from 25 micrometers ($\mu$m) to 50 $\mu$m, as opposed to native bowel that might have a two-walled thickness on the order of millimeters. Since the laser light penetration depth is only a few hundred micrometers, for fused samples excitation and fluorescence collection is possible throughout the entire sample depth. Secondly, the fact that bowel layers are compressed means that there is a higher concentration of fluorophores per unit volume in fused samples compared to normal tissues. A third factor is the compaction, which means that the probe is in closer contact with the most fluorescent layer, the submucosa.

The method described herein demonstrated for the first time the use of laser-induced fluorescence to characterize the fused tissues in heat-induced tissue fusion. The fluorescence results were correlated to both BP and histological results to provide further insights into the mechanism for heat-induced tissue fusion. The fluorescence spectra and statistical analysis show clearly that different tissue fusion classes have distinct fluorescence spectral features. This paves the way for using laser-induced fluorescence as an advanced feedback control method to understand as well as to control the tissue fusion. The existing parameters in tissue-fusion feedback control are mainly tissue temperature and tissue impedance. Unfortunately, these two parameters do not provide the most reliable indication of the quality of the tissue seal. Methods and systems for monitoring of tissue during a surgical procedure in accordance with the present disclosure utilize fluorescence as a parameter, wherein the formation of the collagen cross-link based amalgam can be directly monitored, which further reveals the fusion strength.

Figure 28:
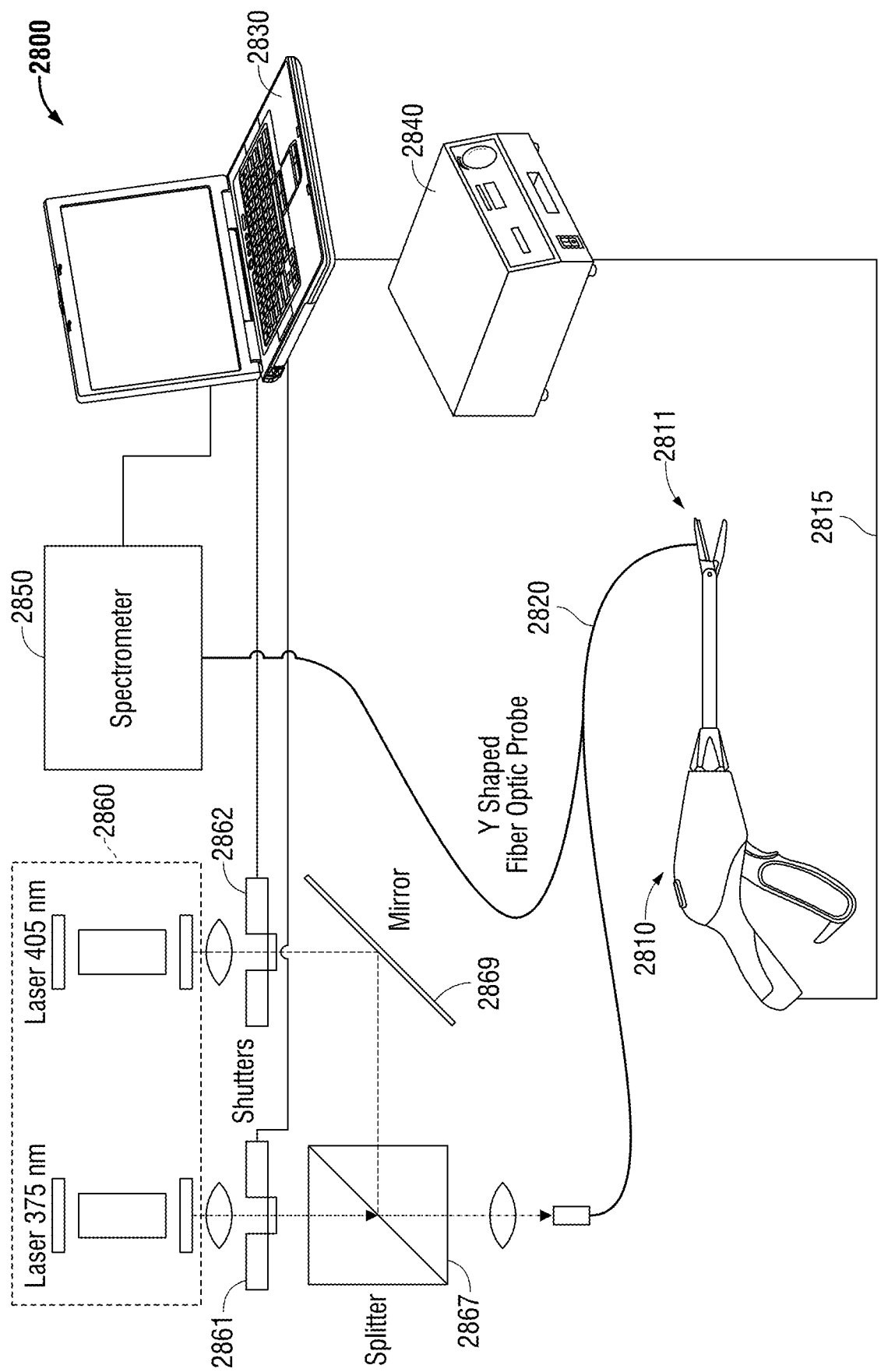
FIG. 28 is a schematic illustration of a system in accordance with an embodiment of the present disclosure.

Real-Time RF Energy-Induced Tissue Seal Fluorescence Monitoring System and Method In FIG. 28, a system for treating tissue (generally referred to herein as system 2800) is shown and generally includes a RF generator 2840 and a surgical instrument 2810 with an end-effector assembly 2811. Surgical instrument 2810 may be any device or instrument suitable for tissue fusion, e.g., a LigaSure Impact™ instrument (Covidien, Boulder, Colo.). Surgical instrument 2810 is connected through a transmission line 2815 (e.g., a bipolar cable) to the RF generator 2840. Surgical instrument 2810 may be configured to be connectable to one or more energy sources, e.g., laser sources, RF generators, and/or self-contained power sources. Surgical instrument 2810 and the end-effector assembly 2811 are similar to the surgical instrument 10 and the end-effector assembly 100 shown in FIG. 1A, and further description of the like elements is omitted in the interests of brevity.

System 2800 is configured for fluorescence real-time monitoring and includes a computer 2830, a spectrometer 2850, a generally Y-shaped two way fiber-optic probe 2820 having one end coupled to the end-effector assembly 2811 of the instrument 2810, a laser source 2860 (also referred to herein as excitation source 2860), and a beam splitter 2867 with mirror 2869, which channels the light from different light sources into a single optical fiber. In some embodiments, as shown for example in FIG. 28, the Y-shaped fiber-optic probe is a custom-made fiber-optic probe (LEONI Fiber Optics GmbH, Muehldamm, Germany). This set-up results in the formation of a two-way laser delivery and fluorescence collection device. System 2800 may include additional, fewer, or different components than shown in FIG. 28, depending upon a particular purpose or to achieve a desired result.

Fiber-optic probe 2820 is configured be inserted into an aperture formed in one of the jaw members of the end-effector assembly 2811. The aperture (not explicitly shown) is configured to be small enough to avoid interference with mechanical strength and electrical parameters of the surgical instrument 2810. The proximal end of the fiber-optic probe 2820 is divided into two arms. The first arm is configured to contain one or more excitation fibers (e.g., excitation fiber 3172 shown in FIG. 31) coupled to the optical output of the laser source 2860. The second arm of the fiber-optic probe 2820 includes one or more emission fibers (e.g., emission fiber 3172 shown in FIG. 31) connected to a registration device, e.g., spectrometer, photodiode, CCD/CMOS camera, etc. The excitation source may include any number of light sources, e.g., laser, LEDs or lamps with bandpass filters, with an appropriate wavelength and power. In some embodiments, as shown for example in FIG. 28, the excitation source 2860 includes two diode lasers with emission wavelengths of 375 nm (L375P020MLD, Thorlabs Inc., Newton, N.J.) and 405 nm (Thorlabs' DL5146-101S), respectively. To choose an appropriate excitation wavelength the mechanical beam shutters (e.g., two shutters 2861 and 2862), optical switchers or light source power commutation may be used.

In some embodiments, the spectrometer 2850 may be a high-sensitivity compact spectrometer, e.g., an Ocean Optics USB4000-FL (Ocean Optics Inc., Dunedin, Fla.), used for fluorescence spectra registration. Spectrometer 2850 may have a longpass filter (e.g., Thorlabs' FEL0450) with a cut-off wavelength of 450 nm for rejection of excitation laser light in the optical entrance.

Shutters 2861 and 2862 may be any suitable optical beam shutters. For example, shutters 2861 and 2862 may be optical beam shutters that utilize a rotary, electro-mechanical actuator to provide millisecond shutter operation (e.g., Thorlabs' SH05 Beam Shutter), and may be configured to open when a pulse control signal is applied.

Computer 2830 may include one or more central processing units (CPUs), which may be coupled to a memory (not explicitly shown). CPUs may include any type of computing device, computational circuit, or any type of processor or processing circuit capable of executing a series of instructions that are stored in a memory. CPUs may be adapted to run an operating system platform and application programs. In some embodiments, the computer 2830 may include a plurality of computer nodes interconnected by a network, e.g., the Ethernet or other computer networking technologies. In some embodiments, the computer 2830 is configured to run LabVIEW software (National Instruments Corporation, Austin, Tex.) used for managing the spectrometer 2850 and the excitation source 2860, synchronization with the RF generator 2840, spectra visualization, preliminary data treatment and/or storing.

During operation of the system 2800, the temporal profile of tissue fluorescence features provide real-time information about the biochemical and structural state of tissue fusion, which cannot be determined using other modalities such as histology or infrared thermography. Tissue fluorescence can be monitored, using the system 2800, during RF tissue fusion and after RF application, when monitoring of electrical parameters and temperature is not possible or is no longer informative to the surgeon. During operation of the system 2800, it is possible to register fluorescence spectra exactly at the moment at which RF application begins and is switched off. During operation of the system 2800, fluorescence data can be used for optimization of the RF delivery protocol, thereby avoiding excessive tissue thermal damage or incomplete fusions, both states which would be incompatible for in vivo tissue healing and survival.

When the operator pushes the "Start" button on sealing device 2810, the RF energy generator 2840 commences electrical energy delivery. From the data output point of the RF generator a "HIGH" signal is seen. This output is connected to an analog-to-digital converter (ADC), e.g., NI DAQ USB-6009 (National Instruments Corporation, Austin, Tex.) which is compatible with LabVIEW. Although not explicitly shown in FIG. 28, the ADC is represented by an electronic connection between the RF generator 2840 and the computer 2830. The signal from the ADC is interpreted by a LABVIEW program and fluorescence acquisition begins immediately. Excitation light with wavelength 375 nm or 405 nm, embodied in light source 2860, is chosen by appropriate opening/closing of the beam shutters 2861 and 2862. When shutter 2861 is open, shutter 2862 is closed and only the 375 nm excitation light is delivered to the tissue, while the spectrometer 2850 acquires the fluorescence spectrum of the tissue excited at 375 nm wavelength in range 450-1000 nm. Following spectral acquisition, shutter 2861 is closed and shutter 2862 opens. The spectrometer 2850 acquires the fluorescence spectrum of tissue excited at 405 nm in the same range. In some embodiments, this cycle is repeated every 300 ms. When RF energy delivery is switched off, the signal from the RF generator servicing output is switched to "LOW." The signal from the ADC is interpreted by the LABVIEW program as being the terminating point of RF fusion. Fluorescence spectra acquisition can then be terminated or continued for as long as necessary according to the set protocol (e.g., 6 seconds). In some embodiments, at the end of acquisition, the fluorescence spectra are saved in separate files for each excitation wavelength. For each spectral acquisition, information is collected about time from the beginning of fusion and when RF energy was applied in relation to commencing spectral acquisition.

Figure 31:
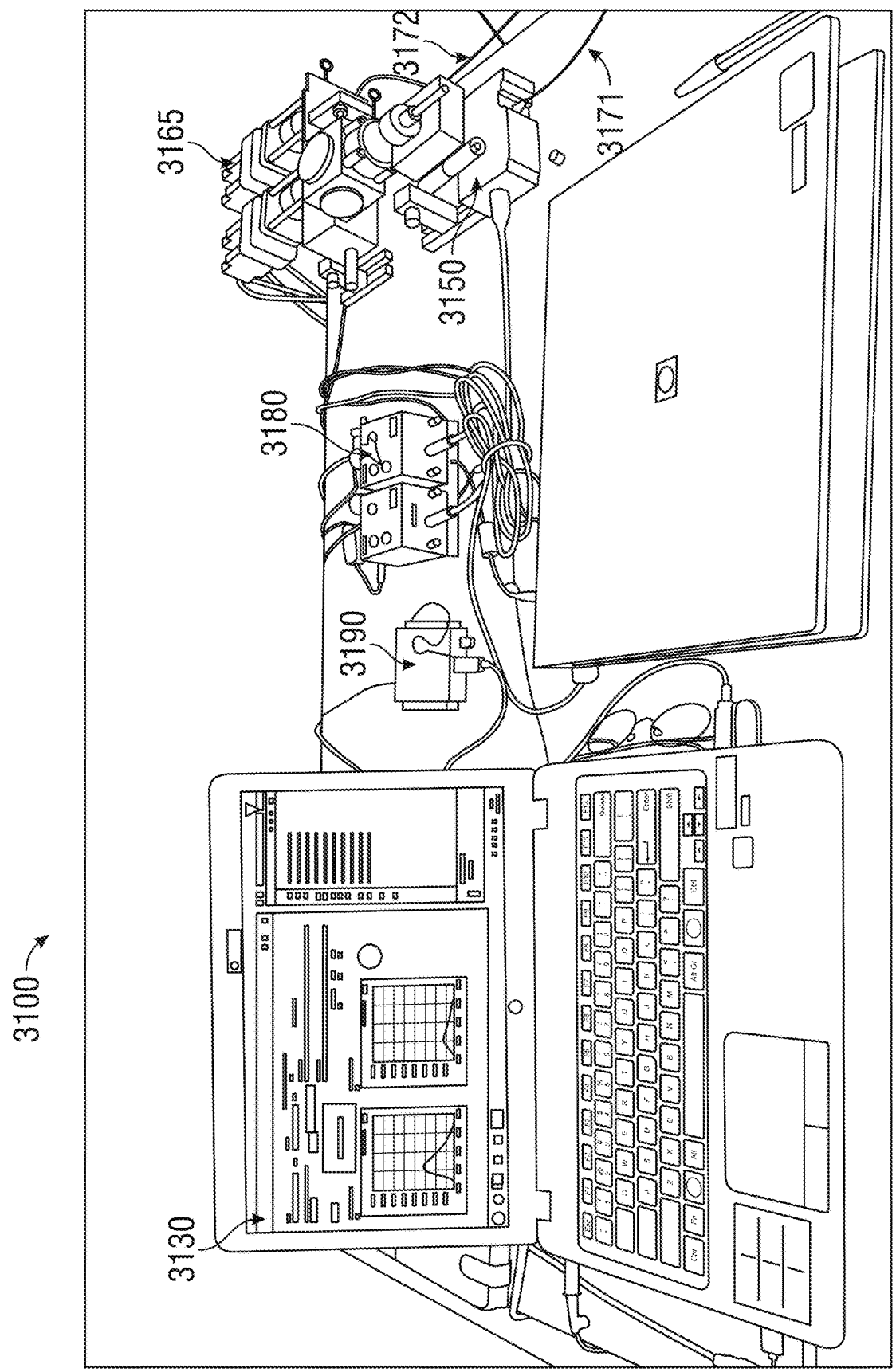
FIG. 31 is an illustration of a real-time multi-wavelength laser-induced fluorescence spectroscopy system in accordance with an embodiment of the present disclosure.

In FIG. 31, an embodiment of the system 2800 in accordance with the present disclosure (referred to herein as the "real-time multi-wavelength laser-induced fluorescence spectroscopy system 3100") is shown and includes a laptop computer 3130 configured to run LabVIEW software, a RF synchronization module 3190 (e.g., the National Instruments USB-6009 data acquisition (DAQ) device), shutter drivers 3180, excitation source 3165 (e.g., laser diodes 375 nm and 405 nm, shutters, collimation optics), spectrometer 3150 (e.g., Ocean Optics' USB4000-FL) for emission registration, excitation fiber 3172, and emission fiber 3171. System 3100 may include additional, fewer, or different components than shown in FIG. 31, depending upon a particular purpose or to achieve a desired result. For example, system 3100 may also include laser power supplies and TEC drivers, which are not shown in FIG. 31.

In an experiment conducted using the real-time multi-wavelength laser-induced fluorescence spectroscopy system 3100, when bowel was fixed into the surgical instrument (e.g., surgical instrument 2810 shown in FIG. 28), before the beginning of fusion, the reference laser-induced fluorescence spectra at excitation wavelengths 375 nm and 405 nm were manually registered. When RF current (e.g., generated by the RF generator 2840 shown in FIG. 28) was applied to tissue, fluorescence spectra at different excitation wavelength were alternately registered with a temporal resolution of approximately 300 ms. Following the end of RF delivery to the tissue, the spectral data acquisition was continued for a further six seconds. The aim of this post-RF acquisition was to permit estimation of the fluorescence signal recovery as a possible diagnostic parameter of the completeness of bowel fusion.

Examples of registered in vivo time profiles of fluorescence intensity at 405 nm for both excitation wavelengths and for different RF fusion protocols are shown in FIGS. 29A through 30C. Data shown in FIGS. 29A through 30C are obtained at the same tissue point during the same RF sealing cycle.

Figure 29A:
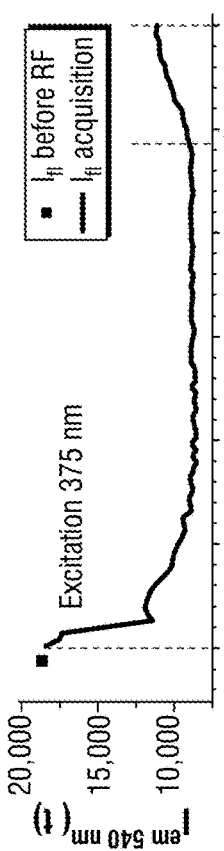
FIGS. 29A through 29C are plots for fusion testing results in accordance with an embodiment of the present disclosure.
Figure 29B:
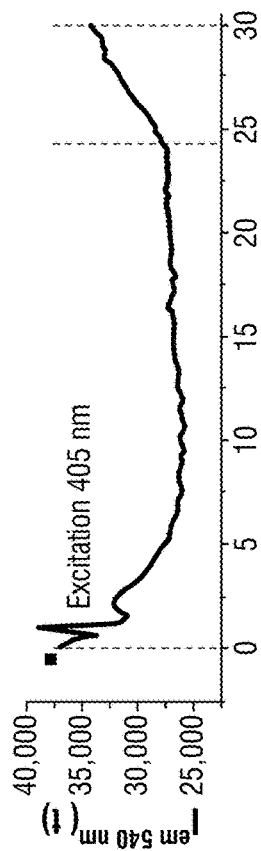
Figure 29C:
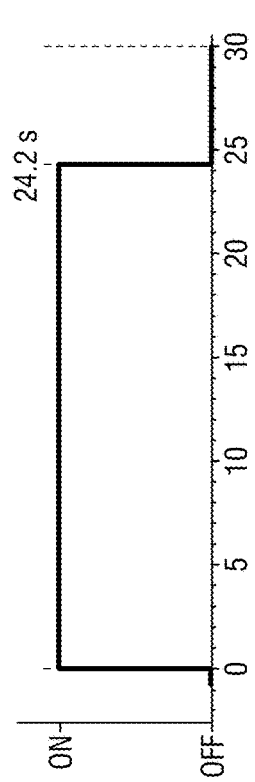
Figure 30A:
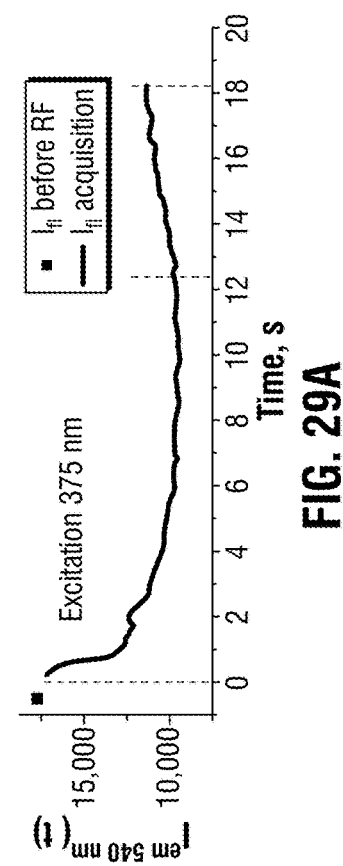
FIGS. 30A through 30C are plots for fusion testing results in accordance with an embodiment of the present disclosure.
Figure 30B:
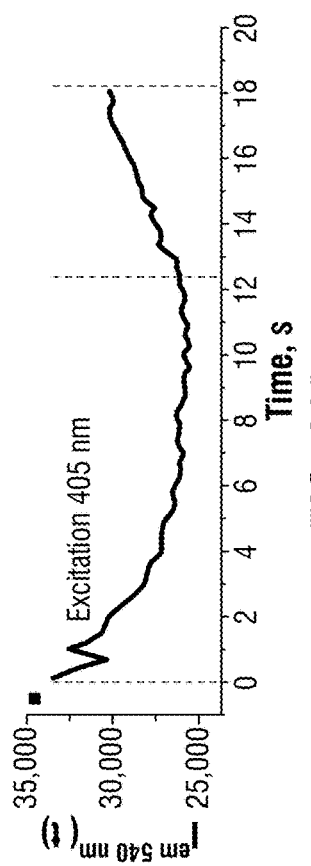
Figure 30C:
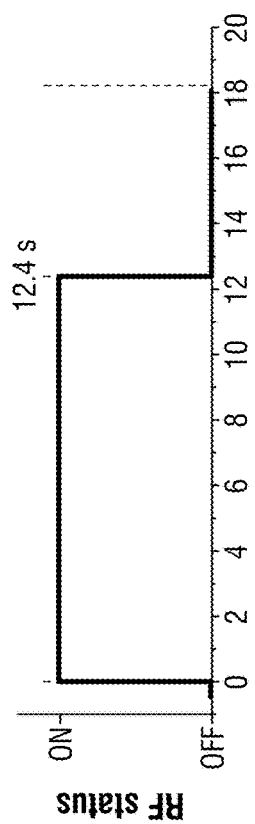

FIGS. 29A through 30C illustrative the fluorescence intensity versus time obtained for excitation wavelength 375 nm (FIGS. 29A, 30A) and 405 nm (FIGS. 29B, 30B), as well as the signal from the RF generator output 2840 (FIGS. 29C, 30C). FIGS. 29A-C present data registered for RF with parameters dz/dt ramp 0.01 ohms/ms, end impedance 100 ohms. For the example shown in FIGS. 29A-C, the duration of RF energy delivery for tissue sealing is approximately 10-12½ seconds.

FIGS. 30A-C show data registered for RF delivery with parameters dz/dt ramp 0.005 ohms/ms, end impedance 100 ohms. For the example shown in FIGS. 30A-C, the seal cycle is approximately 20-25 seconds.

Every point on the graphs depicted in FIGS. 29A-B and FIGS. 30A-B presents the fluorescence intensity, registered at 540 nm. The black box at time <0 presents fluorescence intensity registered manually just before RF energy was applied. At the time point "0" RF energy is applied and the signal on the servicing output of RF generator is changes from 1.3 V "OFF" to 4.5 V "ON" (FIG. 29C, FIG. 30C). Acquisition commences and fluorescence intensity is registered synchronously to shutters 2861 and 2862 (FIG. 28), opening approximately every 300 ms. When RF fusion is finished, RF energy delivery is switched off and the synchronisation signal is changed to 1.4 V (OFF). Fluorescence acquisition is continued for a fixed time period after RF energy delivery is terminated (6 seconds in the examples shown). After RF energy is switched off, some fluorescence intensity recovery was observed. Fluorescence intensity is noted to decrease by approximately 30% at the end of tissue fusion.

A method of treating tissue in accordance with an embodiment of the present disclosure includes positioning an end-effector assembly 100 (FIG. 1) including first and second jaw members 110 and 120 at a first position within tissue. The first and second jaw members 110 and 120 include tissue-contacting surfaces 112 and 122, respectively. At least one of the first and second jaw members 110 and 120 is movable from a spaced relation relative to the other jaw member to at least one subsequent position wherein the tissue-contacting surfaces 112 and 122 cooperate to grasp tissue therebetween. The method also includes activating a light-emitting element associated with one or both of the first and second jaw members 110 and 120 to emit light into tissue and evaluating one or more characteristics of the tissue based on a response to light entering the tissue. In some embodiments, evaluating the one or more characteristics of the tissue includes evaluating laser-induced tissue fluorescence spectra, e.g., using the real-time multi-wavelength laser-induced fluorescence spectroscopy system 3100 (FIG. 31).

Although embodiments have been described in detail with reference to the accompanying drawings for the purpose of illustration and description, it is to be understood that the disclosed processes and apparatus are not to be construed as limited thereby. It will be apparent to those of ordinary skill in the art that various modifications to the foregoing embodiments may be made without departing from the scope of the disclosure.

What is claimed is:

1. A medical instrument, comprising:
   a housing;
   a shaft coupled to the housing, the shaft having a proximal end and a distal end;

an end-effector assembly disposed at the distal end of the shaft, the end-effector assembly including a first jaw member and a second jaw member pivotably coupled to each other defining an angle therebetween, at least one of the first jaw member or the second jaw member movable from a first position wherein the first and second jaw members are disposed in spaced relation relative to one another to at least a second position closer to one another wherein the first and second jaw members cooperate to grasp tissue therebetween, the end effector including an angle sensor disposed in at least one of the first jaw member or the second jaw member, the angle sensor configured to measure the angle between the first jaw member and the second jaw member;

at least one light-emitting element coupled to at least one of the first jaw member or the second jaw member, the at least one light-emitting element adapted to deliver light energy at a plurality of wavelengths to the tissue grasped between the first and second jaw members;

at least one light-detecting element configured to generate a plurality of fluorescence spectra indicative of tissue fluorescence at the plurality of wavelengths; and a controller configured to receive the plurality of fluorescence spectra and determine properties of a tissue seal based on a difference between the plurality of fluorescence spectra, the controller being coupled to the at least one light-emitting element and the angle sensor, the controller further configured to adjust the intensity of light energy emitted based on the angle.

2. The medical instrument of claim 1, wherein at least one of the first jaw member or the second jaw member includes a groove defined therein having a reflective surface.

3. The medical instrument of claim 2, wherein the at least one light-emitting element is disposed within the groove.

4. The medical instrument of claim 1, further comprising an optical assembly coupled to the at least one light-emitting element, the optical assembly configured to convey light energy emitted from the at least one light-emitting element to the tissue and to illuminate the tissue with a desired illumination pattern.

5. The medical instrument of claim 4, wherein the optical assembly includes at least one of an optical fiber, a refractive element, a reflective element, a diffracting element, and combinations thereof.

6. The medical instrument of claim 1, further comprising a first electrically-conductive tissue-contacting surface associated with the first jaw member and a second electrically-conductive tissue-contacting surface associated with the second jaw member, wherein one of the first electrically-conductive tissue-contacting surface or the second electrically-conductive tissue-contacting surface functions as an active electrode and the other one of the first or the second electrically-conductive tissue-contacting surfaces functions as a return electrode during activation such that electrical energy flows from the active electrode through tissue positioned between the first electrically-conductive tissue-contacting surface or the second electrically-conductive tissue-contacting surface to the return electrode.

7. The medical instrument of claim 6, wherein at least one of the electrically-conductive tissue-contacting surfaces includes a reflective element configured to reflect light energy passing through the tissue.

8. A medical instrument, comprising:
a housing;
a shaft coupled to the housing, the shaft having a proximal end and a distal end;
an end-effector assembly disposed at the distal end of the shaft, the end-effector assembly including a first jaw member and a second jaw member pivotably coupled to each other defining an angle therebetween, at least one of the first jaw member or the second jaw member movable from a first position wherein the first and second jaw members are disposed in spaced relation relative to one another to at least a second position closer to one another wherein the first and second jaw members cooperate to grasp tissue therebetween, the end effector including an angle sensor disposed in at least one of the first jaw member or the second jaw member, the angle sensor configured to measure the angle between the first jaw member and the second jaw;

at least one light-emitting element coupled to at least one of the first jaw member or the second jaw member, the at least one light-emitting element adapted to deliver light energy at a plurality of wavelengths to the tissue grasped between the first and second jaw members; and a controller configured to control electrical energy delivered to the tissue disposed between the first and second jaw members and configured to determine properties of a tissue seal based on a difference between a plurality of fluorescence spectra obtained in response to the light energy delivered at the plurality of wavelengths, the controller being coupled to the at least one light-emitting element and the angle sensor, the controller further configured to adjust the intensity of light energy emitted based on the angle.

9. The medical instrument of claim 8, further comprising at least one light-detecting element configured to generate one or more signals indicative of tissue fluorescence at the plurality of wavelengths of collagen.

10. The medical instrument of claim 9, wherein the controller is coupled to the at least one light-detecting element.

11. A system for treating tissue, comprising:
a medical instrument including:
a housing;
a shaft coupled to the housing, the shaft having a proximal end and a distal end;
an end-effector assembly disposed at the distal end of the shaft, the end-effector assembly including a first and a second jaw member pivotably coupled to each other defining an angle therebetween, at least one of the first jaw member or the second jaw member movable from a first position wherein the first or the second jaw members are disposed in spaced relation relative to one another to at least a second position closer to one another wherein the first and second jaw members cooperate to grasp tissue therebetween, the end effector including;
a first tissue-contacting surface associated with the first jaw member;
a second tissue-contacting surface associated with the second jaw member;
an angle sensor disposed in at least one of the first jaw member or the second jaw member, the angle sensor configured to measure the angle between the first jaw member and the second jaw member;
at least one light-emitting element coupled to at least one of the first jaw member or the second jaw member, the at least one light-emitting element adapted to deliver light energy at a plurality of wavelengths to the tissue grasped between the first and second jaw members; and
at least one light-detecting element configured to sense at least one property of the light energy passing through the tissue and to generate a plurality of fluorescence spectra indicative of tissue fluorescence at the plurality of wavelengths in response to the sensed at least one property of the light energy; and a controller coupled to the at least one light-detecting element and the at least one light-emitting element, the controller configured to receive the plurality of fluorescence spectra and control electrical energy delivered to the tissue disposed between the first and second tissue-contacting surfaces during activation based on a difference between the plurality of fluorescence spectra, wherein the controller is coupled to the at least one light-emitting element and the angle sensor, the controller further configured to adjust the intensity of light energy emitted based on the angle.

12. The system according to claim 11, wherein either one or both of the first and second tissue-contacting surfaces includes an absorbent coating disposed thereon, the absorbent coating configured to absorb light energy emitted from the at least one light-emitting element to heat at least a portion of at least one of the first and second jaw members.

13. The system of claim 11, wherein either one or both of the first and second tissue-contacting surfaces includes a reflective coating disposed thereon, the reflective coating configured to reflect light energy emitted from the at least one light-emitting element.

14. The system of claim 11, further comprising an energy source configured to provide light energy to the at least one light-emitting element.

15. The system of claim 14, wherein the controller is disposed within the energy source.

16. The system of claim 11, wherein the controller is integrally formed with the medical instrument.

17. The system of claim 11, wherein the controller is coupled to the medical instrument.

* * * * *